US010172911B2

(12) United States Patent
Mezey et al.

(10) Patent No.: US 10,172,911 B2
(45) Date of Patent: Jan. 8, 2019

(54) METHODS OF MODULATING ERYTHROPOIESIS WITH ARGININE VASOPRESSIN RECEPTOR 1B MOLECULES

(71) Applicant: The United States of America, as represented by the Secretary, Department of Health and Human Services, Washington, DC (US)

(72) Inventors: Eva M. Mezey, Rockville, MD (US); Balazs Mayer, Budakeszi (HU); Krisztian Nemeth, Budapest (HU); Miklos Krepuska, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 27 days.

(21) Appl. No.: 15/022,531

(22) PCT Filed: Oct. 1, 2014

(86) PCT No.: PCT/US2014/058613
§ 371 (c)(1),
(2) Date: Mar. 16, 2016

(87) PCT Pub. No.: WO2015/050983
PCT Pub. Date: Apr. 9, 2015

(65) Prior Publication Data
US 2016/0220631 A1  Aug. 4, 2016

Related U.S. Application Data
(60) Provisional application No. 61/885,258, filed on Oct. 1, 2013.

(51) Int. Cl.
*A61K 38/00* (2006.01)
*A61K 38/11* (2006.01)
*A61K 38/18* (2006.01)
*A61K 45/06* (2006.01)
*A61K 31/465* (2006.01)
*A61K 31/404* (2006.01)

(52) U.S. Cl.
CPC ............ *A61K 38/11* (2013.01); *A61K 31/404* (2013.01); *A61K 31/465* (2013.01); *A61K 38/1816* (2013.01); *A61K 45/06* (2013.01)

(58) Field of Classification Search
None
See application file for complete search history.

(56) References Cited

U.S. PATENT DOCUMENTS

| 2006/0123503 | A1 | 6/2006 | Brennan et al. |
| 2007/0065415 | A1 | 3/2007 | Kleinsek et al. |
| 2009/0088387 | A1* | 4/2009 | Castillo ............ A61K 47/48038 514/1.1 |
| 2009/0298711 | A1 | 12/2009 | Russell et al. |

FOREIGN PATENT DOCUMENTS

| EP | 0 381 345 B1 | 8/1990 |
| EP | 1 365 247 A1 | 11/2003 |
| WO | WO 01/08683 A1 | 2/2001 |
| WO | WO 01/08684 A1 | 2/2001 |
| WO | WO 02/067980 A1 | 9/2002 |
| WO | WO 03/100433 A2 | 12/2003 |
| WO | WO 2004/000993 A2 | 12/2003 |
| WO | WO 2006/063168 A2 | 6/2006 |
| WO | WO 2008/144269 A2 | 11/2008 |
| WO | WO 2009/045309 A2 | 4/2009 |

OTHER PUBLICATIONS

Jepson et al. Erythropoietin excretion in a hypopituitary patient. Effects of testosterone and vasopressin. Archives of internal medicine, Abstract, vol. 122, No. 3, pp. 265-270 (1968).*
Lohr et al. Minimizing Hemorrhagic Complications in Dialysis Patients. Journal of the American Society of Nephrology. vol. 2:961-975 (1991).*
Seki et al. Osteoporosis and spondylolisthesis after compresive treatment for brain tumor: A case report. Clinical Pediatric Endocrinology vol. 10/1:41-45 (2001).*
Pena et al. Pharmacological and physiological characterizatrion of d[Leu4,Lys8]Vasopressin, the first V1b selective agonist for rat vassopressin/oxytocin receptors. Endocrinology, vol. 148(9):4136-4146 (2007).*
Moresi et al. (Modulation of Caspase Activity Regulates Skeletal Muscle Regeneration and Function in Response to Vassopressin and Tumor Necroses Factor. PLos One, vol. 4, Issue 5, e5570, pp. 1-18; May 2009). (Year: 2009).*
Christine et al. Stimulation of the pituitary-adrenal axis with a lose dose of [Arg8]-vasopressin in depressed patients and healthy subjects. European Neuropsychopharmacology vol. 2:411-419 (1992) (Year: 1992).*

(Continued)

*Primary Examiner* — Elizabeth C. Kemmerer
*Assistant Examiner* — Regina M DeBerry
(74) *Attorney, Agent, or Firm* — Klarquist Sparkman, LLP

(57) ABSTRACT

Disclosed are methods of modulating erythropoiesis with arginine vasopressin receptor 1B (AVPR1B) molecules, such as AVPR1B agonists or antagonists. In one example, a method of stimulating erythropoiesis is disclosed including administering an effective amount of an AVPR1B stimulatory molecule to a subject in need thereof, thereby stimulating erythropoiesis. Also disclosed is a method of stimulating hematopoetic stem cell (HSC) proliferation which includes administering an effective amount of an AVPR1B stimulatory molecule to a subject in need thereof, thereby stimulating HSC proliferation. A method of inhibiting HSC proliferation including administering an effective amount of an AVPR1B inhibitory molecule to a subject in need thereof, thereby inhibiting HSC proliferation is provided.

22 Claims, 32 Drawing Sheets
Specification includes a Sequence Listing.

(56) References Cited

OTHER PUBLICATIONS

Aubert et al., "Nicotine-Induced Release of Vasopressin in the Conscious Rat: Role of Opioid Peptides and Hemodynamic Effects," *J Pharmacol Exp Ther. 243*:681-685, 1987.
Bussolati and Cassoni "Editorial: The Oxytocin/Oxytocin Receptor System—Expect the Unexpected," *Endocrinology 142*:1377-1379, 2001.
Calabrese "Estrogen and Related Compounds: Biphasic Dose Responses," *Crit Rev Toxicol. 31*:503-515, 2001.
Cassoni et al. "Oxytocin Induces Proliferation and Migration in Immortalized Human Dermal Microvascular Endothelial Cells and Human Breast Tumor-Derived Endothelial Cells," *Mol Cancer Res. 4*:351-359, 2006.
Chini and Manning "Agonist Selectivity in the Oxytocin/Vasopressin Receptor Family: New Insights and Challenges," *Biochem Soc Trans. 35*:737-741, 2007.
Fisher and Scott "Role of PU.1 in Hematopoiesis." *Stem Cells 16*:25-37, 1998.
Galea and Davidson, "Haematological and Haemorheological Changes Associated with Cigarette Smoking," *J Clin Pathol. 38*:978-984, 1985.
Hunt et al., "Role of Vasopressin in the Mitotic Response of Rat Bone Marrow Cells to Haemorrhage," *J. Endocr. 72*:5-16, 1977.
Khaldoyanidi et al. "Correlation between Nicotine-induced Inhibition of Hematopoiesis and Decreased CD44 Expression on Bone Marrow Stromal Cells." *Blood 98*:303-312, 2001.
Kokaze et al., "Interaction Between Longevity-Associated Mitochondrial DNA 5178 C/A Polymorphism and Cigarette Smoking on Hematological Parameters in Japanese Men," *Arch Gerontol Geriat. 40*:113-122, 2005.
Krebsbach et al. "Bone Marrow Stromal Cells: Characterization and Clinical Application." *Crit Rev Oral Biol Med. 10*:165-181, 1999.
Manning et al., "Oxytocin and Vasopressin Agonists and Antagonists as Research Tools and Potential Therapeutics," *J Neuroendocrinol. 24*:609-628, 2012.
Mason, "Staining of the Magnocellular Nuclei of the Rat Hypothalamus by a Monoclonal Antibody Directed Against the α-Subunit of the Nicotinic Cholinergic Receptor," *Neurosci Lett. 59*:89-95, 1985.
Mayer et al., "Vasopressin and Oxytocin Regulate Hematopoiesis Through the Wnt and Akt Pathways," Poster Board No. 2385, ISSCR 9$^{th}$ Annual Meeting, 2011.
Miszta et al. "Effect of Vasopressin, Oxytocin and LHRH on the Proliferation and Metabolism of Rat Bone Marrow Stromal Cells in Culture." Endocr Regul. 25:177-180, 1991. (Abstract Only).
Novak et al. "A Plasmin-derived Hexapeptide from the Carboxyl End of Osteocalcin Counteracts Oxytocin-Mediated Growth of Inhibition of Osteosarcoma Cells." *Cancer Res. 60*:3470-3476, 2000.
Oberhoff et al. "Recombinant Human Erythropoietin in the Treatment of Chemotherapy-induced Anemia and Prevention of Transfusion Requirement Associated with Solid Tumors: A Randomized, Controlled Study." *Annals Oncol. 9*:255-260, 1998.
Paquin et al. "Oxytocin Induced Differentiation of P19 Embryonic Stem Cells to Cardiomyocytes." *Proc Natl Acad Sci USA. 99*:9550-9555, 2002.
Pena et al., "Pharmacological and Physiological Characterization of d[Leu4, Lys8] Vasopressin, the First V1b-Selective Agonist for Rat Vasopressin/Oxytocin Receptors," *Endocrinol. 148*:4136-4146, 2007.
Perris and Hunt "Stimulation of Mitosis in Rat Bone Marrow Cells by Antidiuretic Hormone after Haemorrhage." *Proc. Soc. Endo.* p. 5-6, 1974.
Roper et al., "The Vasopressin Avpr1b Receptor: Molecular and Pharmacological Studies," *Stress 14*:98-115, 2011.
Saito et al., "1-Desamino-8-D-Arginine Vasopressin (DDAVP) as an Agonist on V-1b Vasopressin Receptor," *Biochem Pharmacol. 53*:1711-1717, 1997.
Shipp and Look "Hematopoietic Differentiation Antigens That Are Membrane-Associated Enzymes: Cutting Is the Key!" *Blood 82*:1052-1070, 1993.
PCT International Search Report for PCT/US2014/058613 dated Mar. 10, 2015 (5 pages).
PCT International Written Opinion for PCT/US2014/058613 dated Mar. 10, 2015 (8 pages).

\* cited by examiner

|       | AVPR1A | AVPR1B | AVPR2 | OXTR |
|-------|--------|--------|-------|------|
| HSC   | +      | +      | -     | ++   |
| MPP1  | +      | +      | -     | ++   |
| MPP2  | -      | +++    | -     | +    |
| MPP3/4| ++     | +      | +     | +    |

|              | AVPR1B | AVPR2 | OXTR |
|--------------|--------|-------|------|
| CD34+CD38-   | ++     | +     | +    |
| CD34+CD38+   | ++     | +     | ++   |
| B cells      | ++     | +     | ++   |
| CD4 cells    | +      | +     | +    |
| CD8 cells    | +      | ++    | +    |
| NK cells     | -      | +     | ++   |
| Dendritic Cells | +   | +     | ++   |
| Monocytes    | +      | +     | +    |
| Macrophages  | -      | -     | +    |

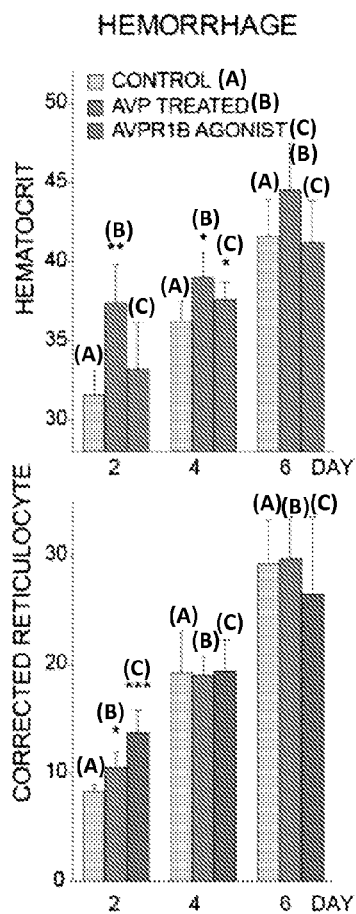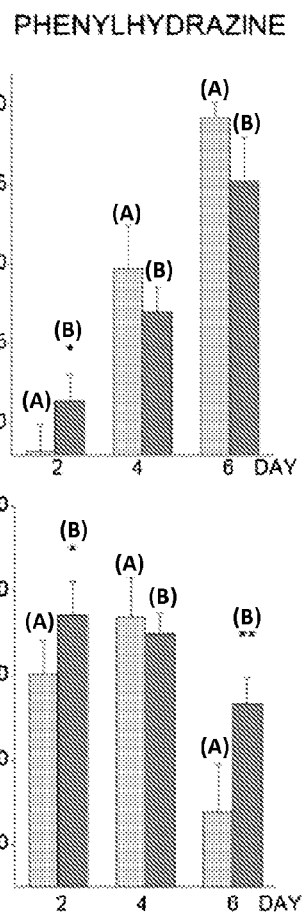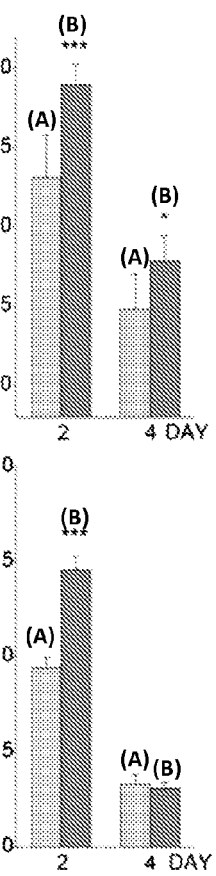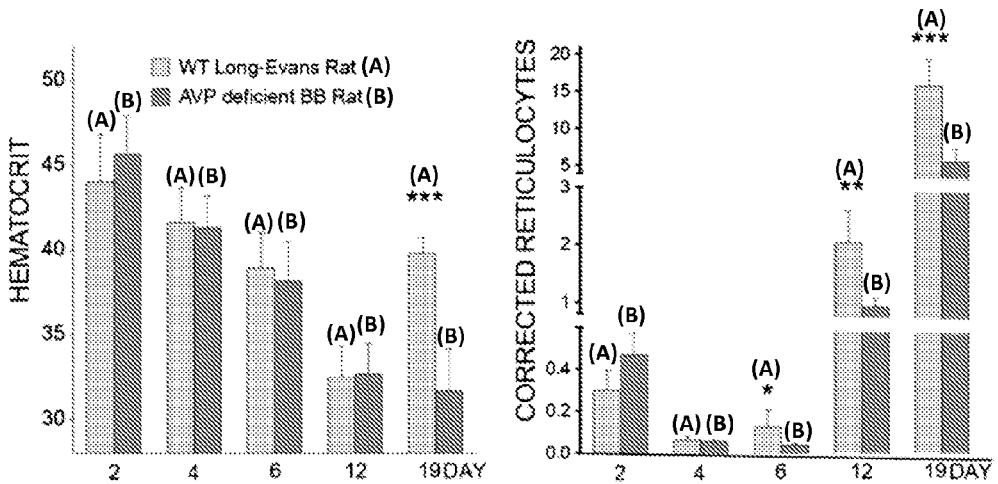
FIG. 4A HEMORRHAGE
FIG. 4B PHENYLHYDRAZINE
FIG. 4C IRRADIATION
FIG. 4D RECOVERY OF BRATTLEBORO RATS AFTER IRRADIATION

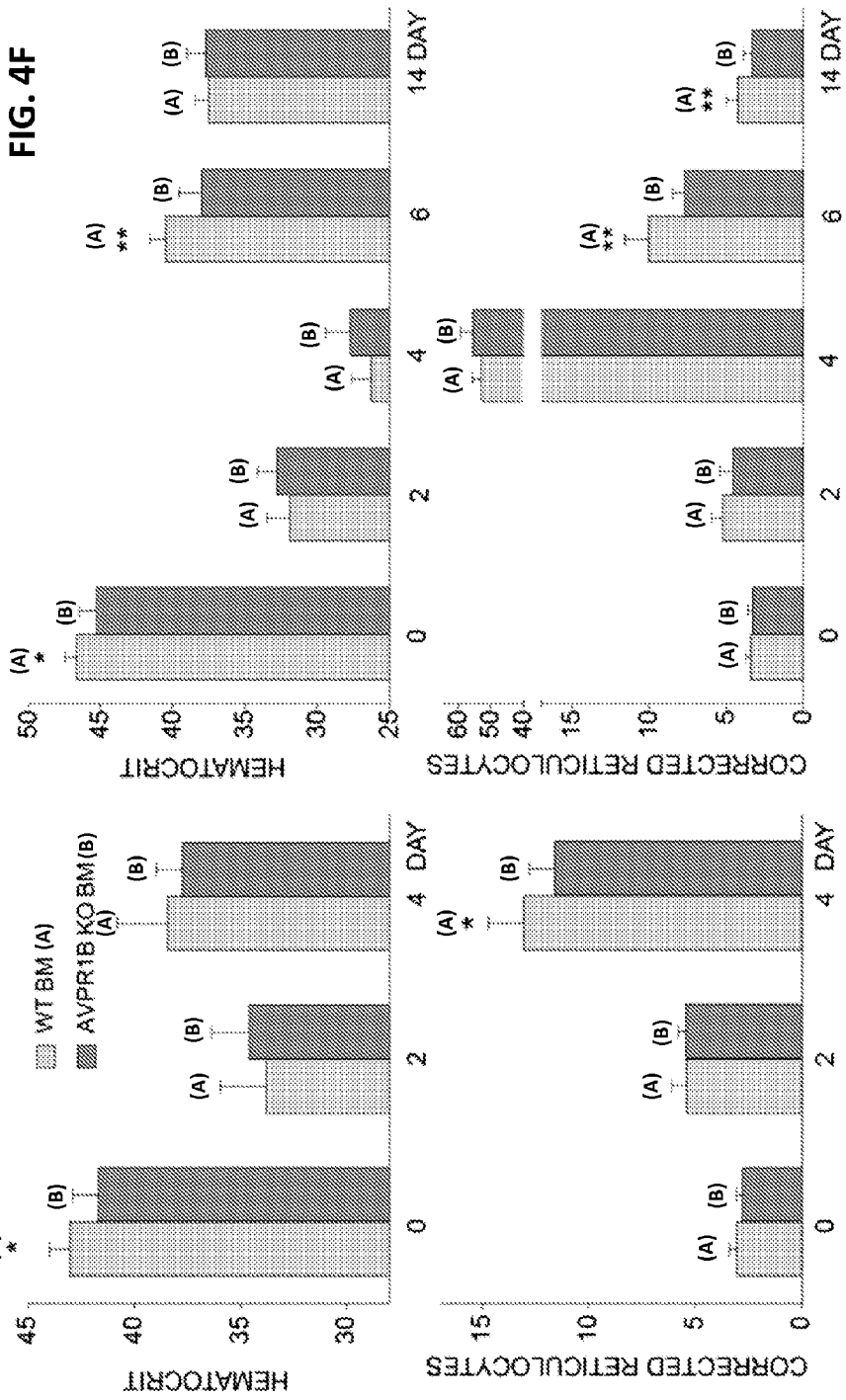

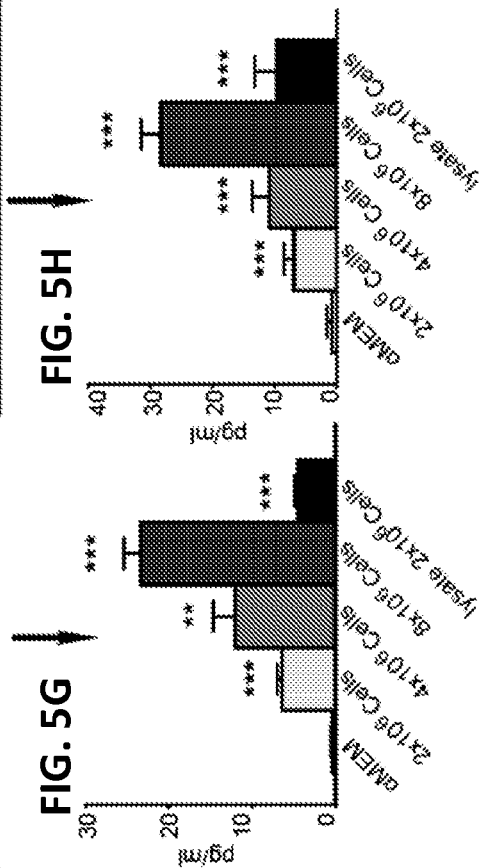
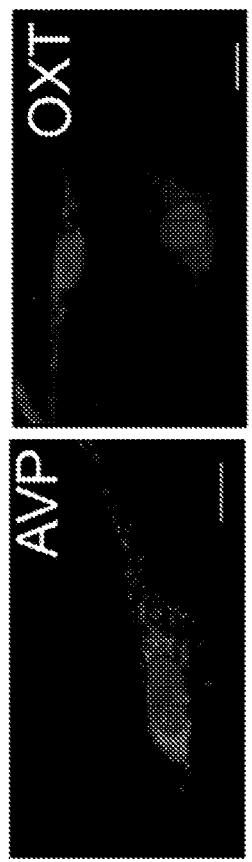
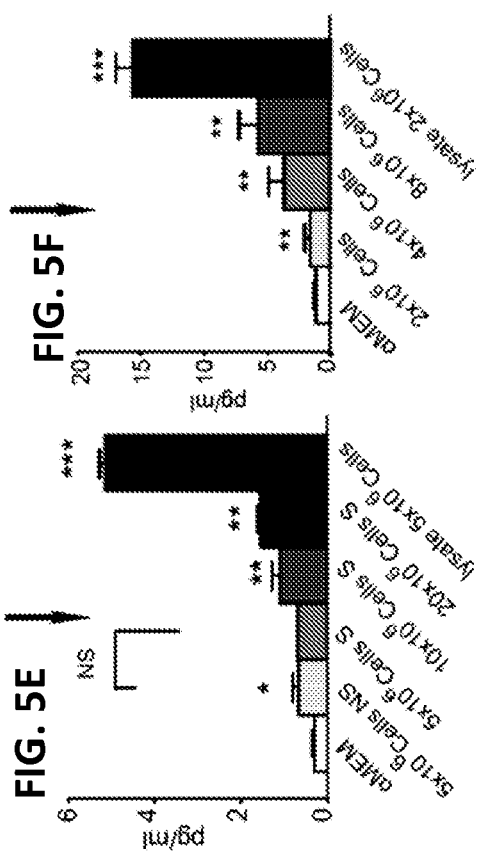
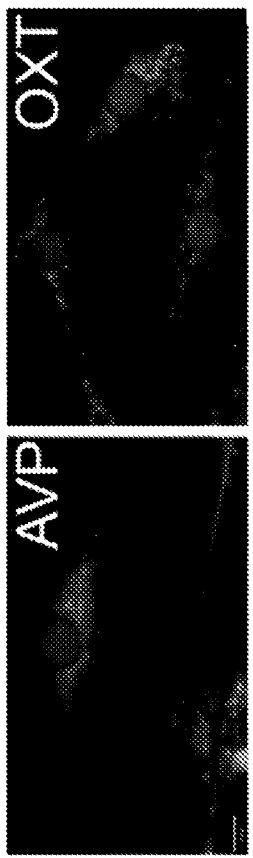

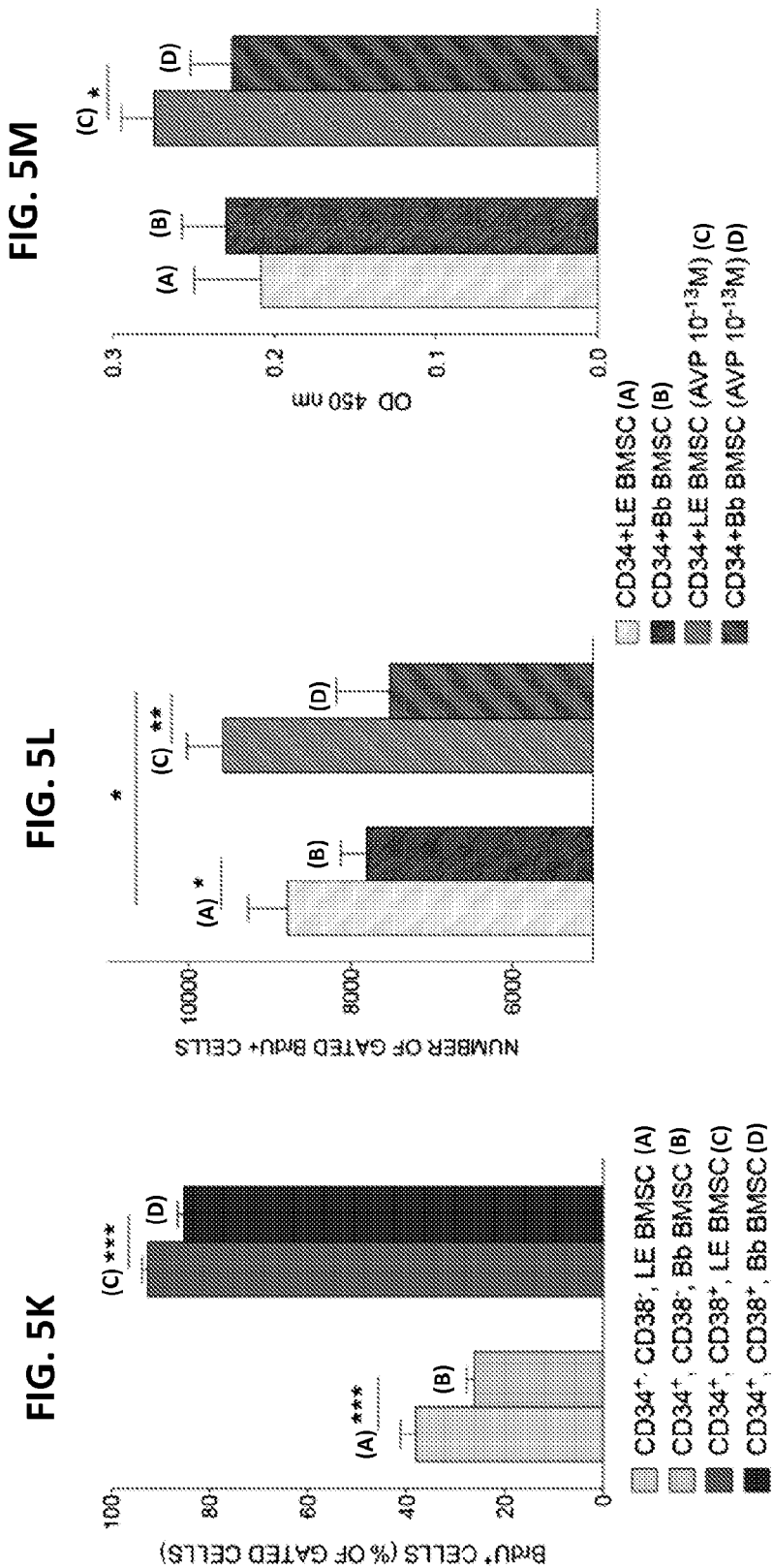

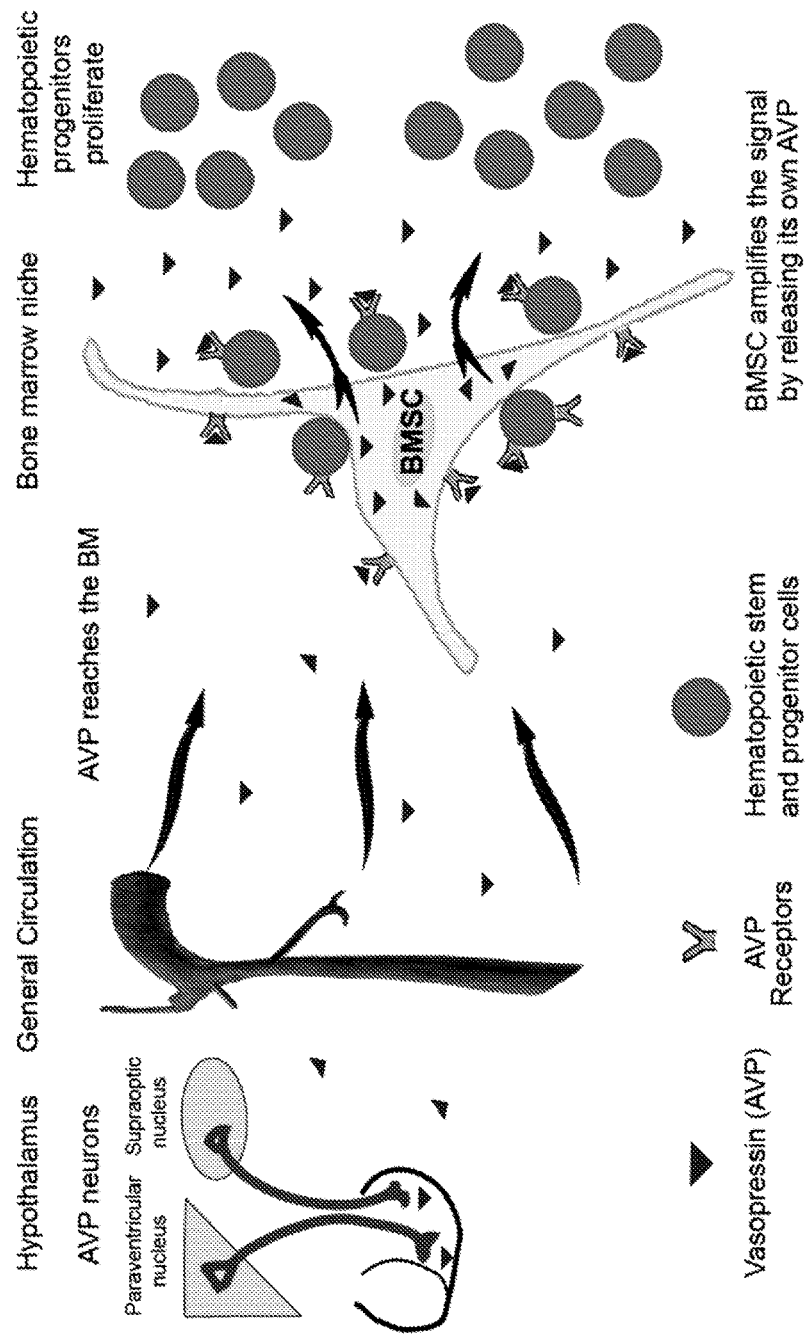

MPP1 AVPR1B

Mouse LSK cell proliferation rate

Human CD34+ cell proliferation rate

FIG. 7G
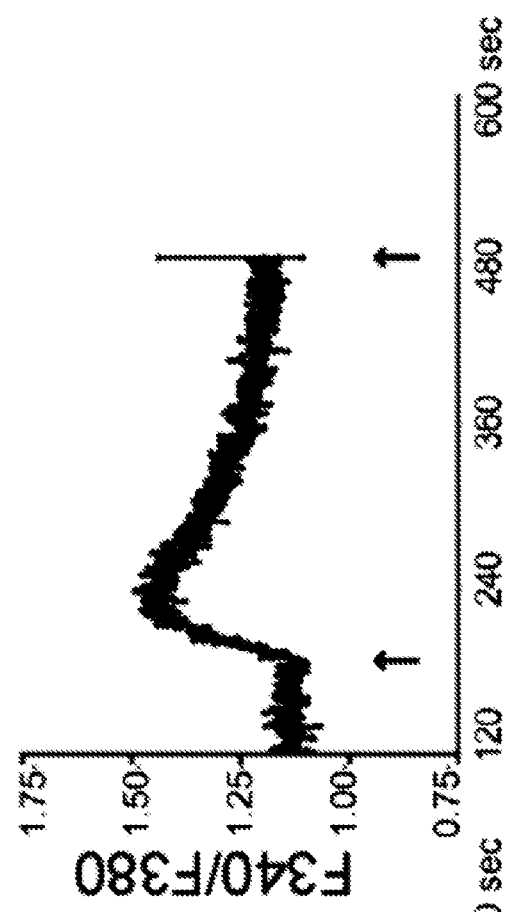
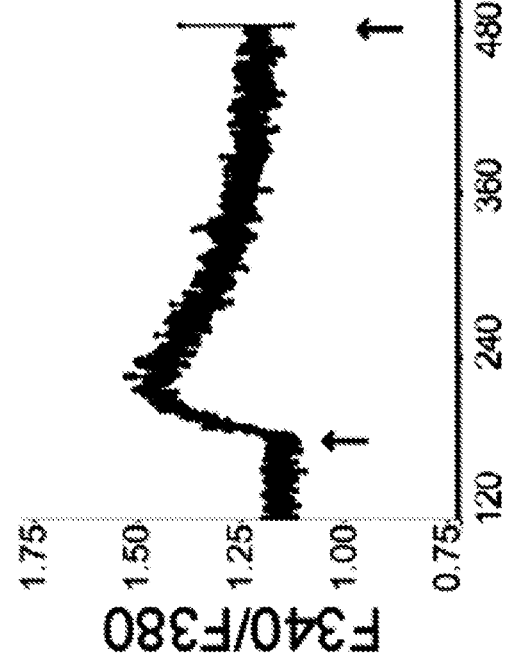

FIG. 8A Nuclear translocation of β-catenin in response to AVP stimulation
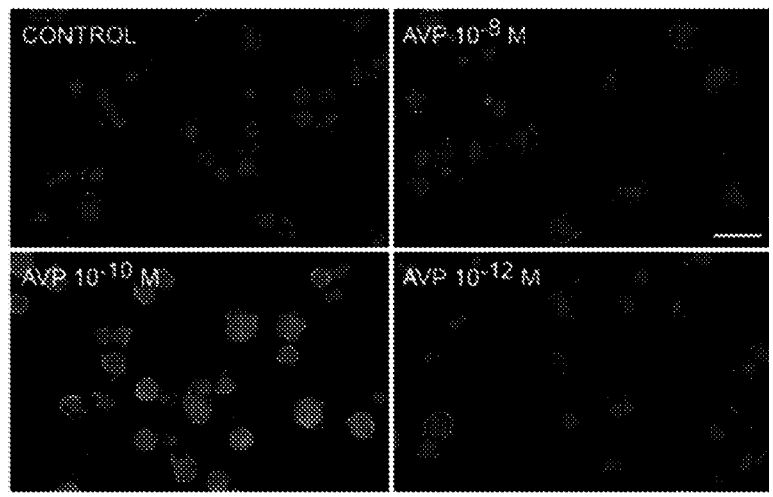
FIG. 8B
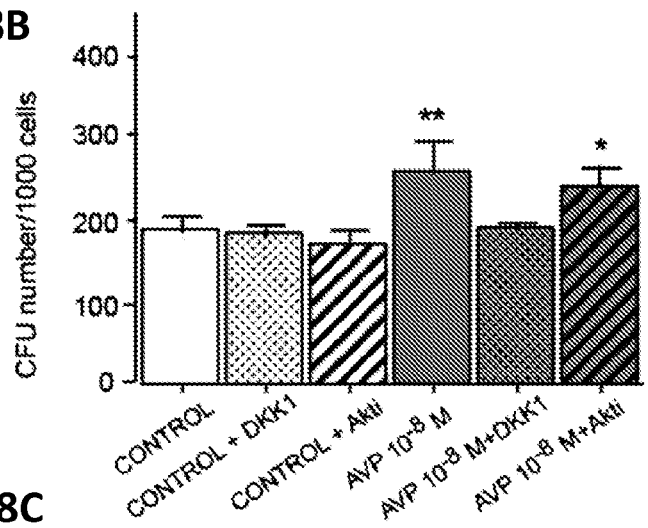
FIG. 8C
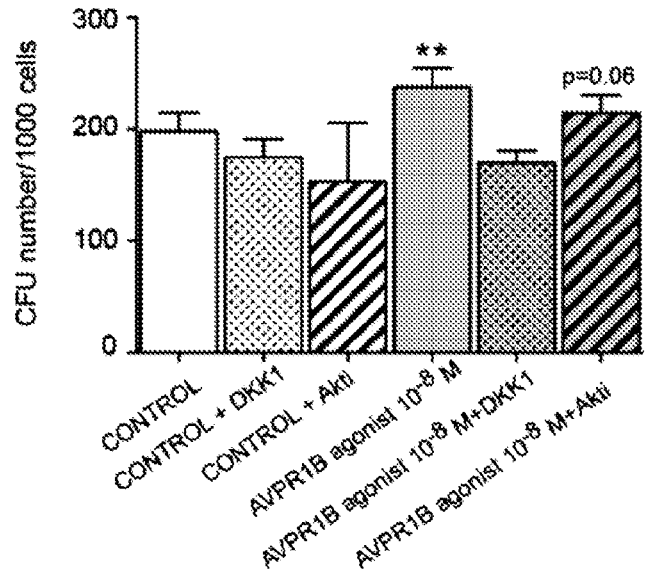

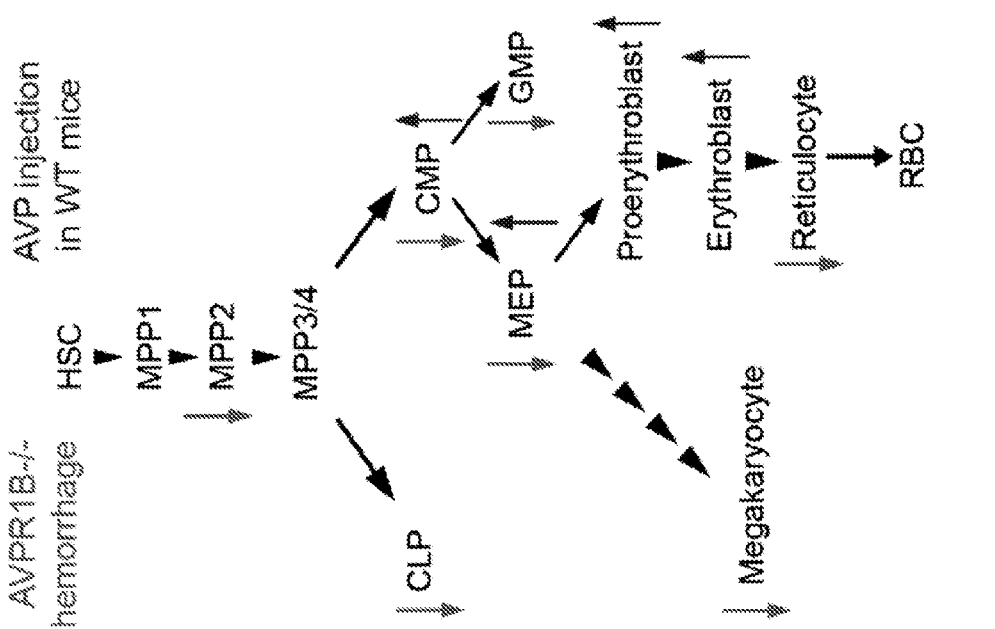
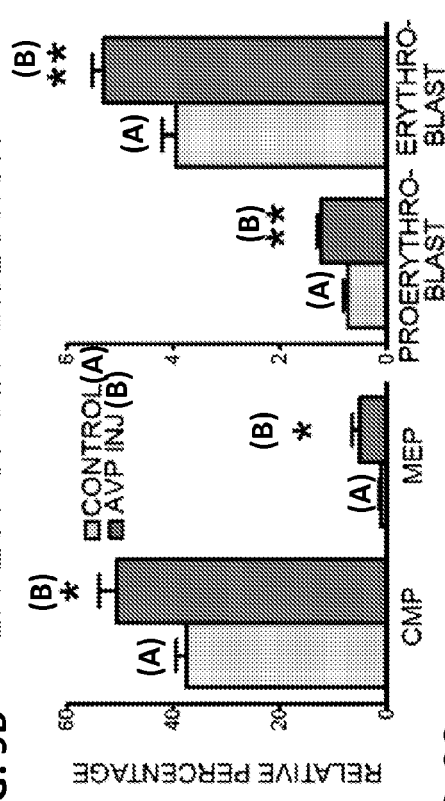
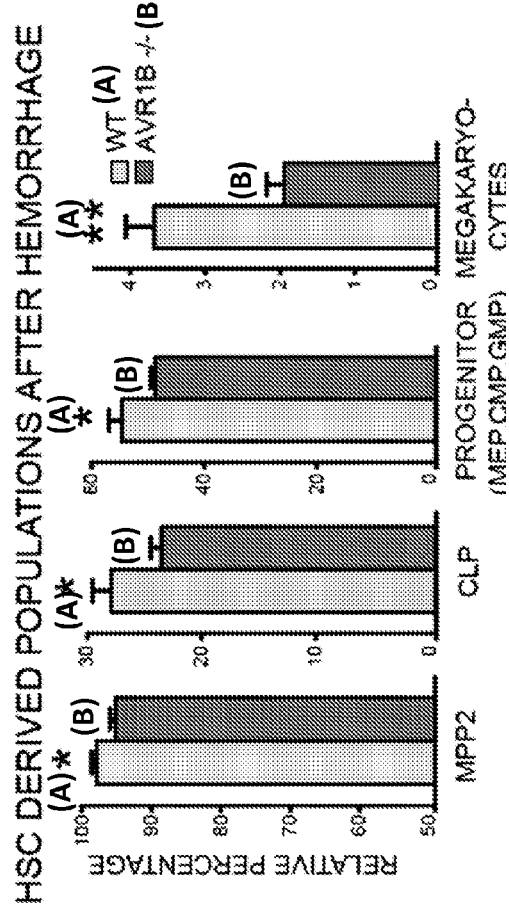
FIG. 9B
FIG. 9C

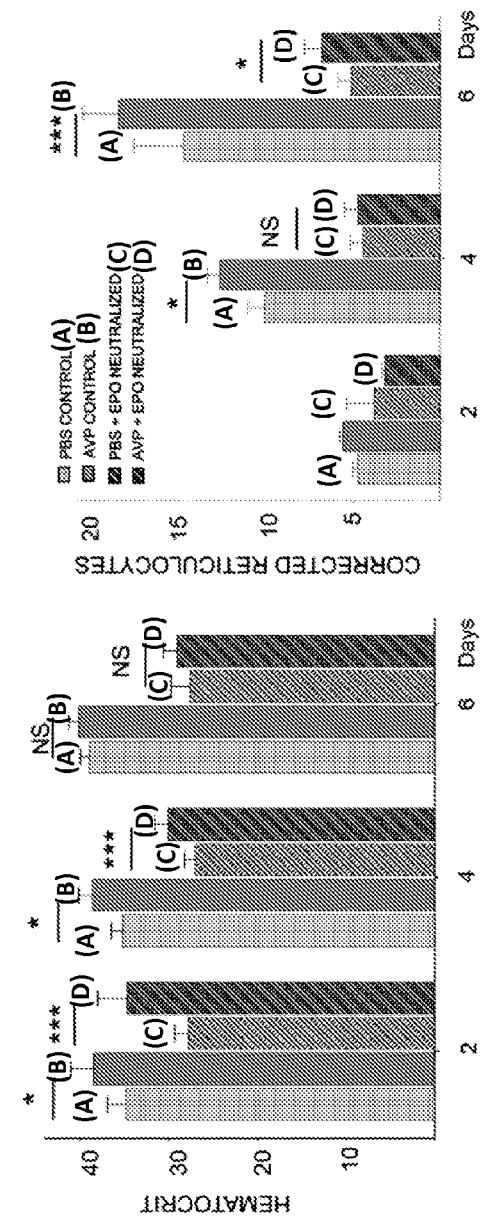
FIG. 10A
FIG. 10B

FIG. 14A Peripheral blood GFP-, CD45.2+ cells
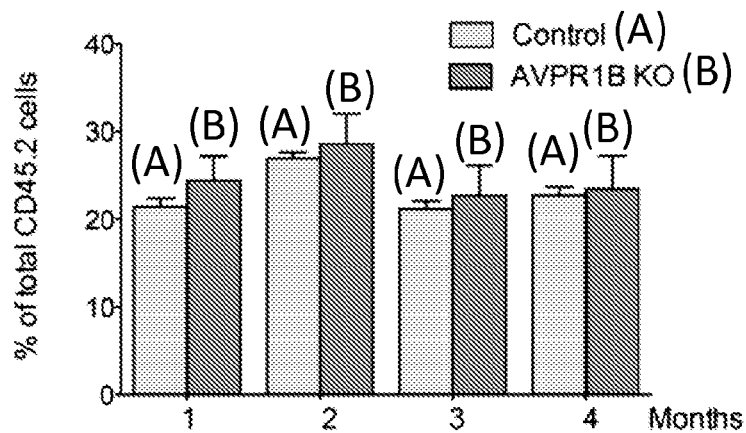
FIG. 14B Bone marrow, GFP-, CD45.2+ multi-lineage cells 4 months after transplant
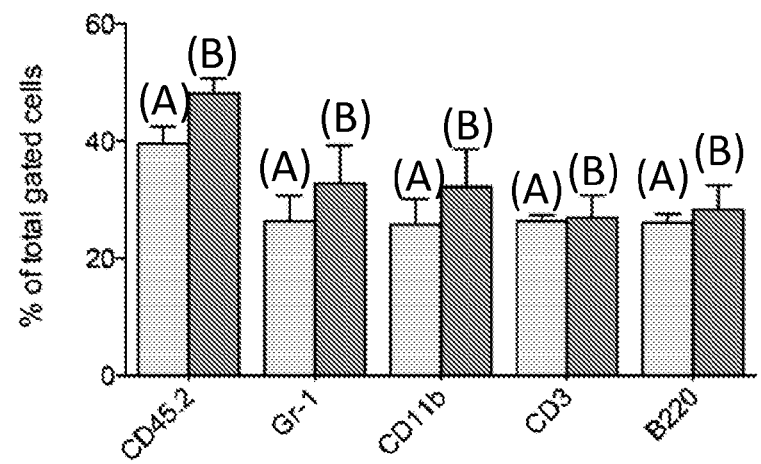
FIG. 14C Spleen, GFP-, CD45.2+, multi-lineage cells, 4 months after transplant
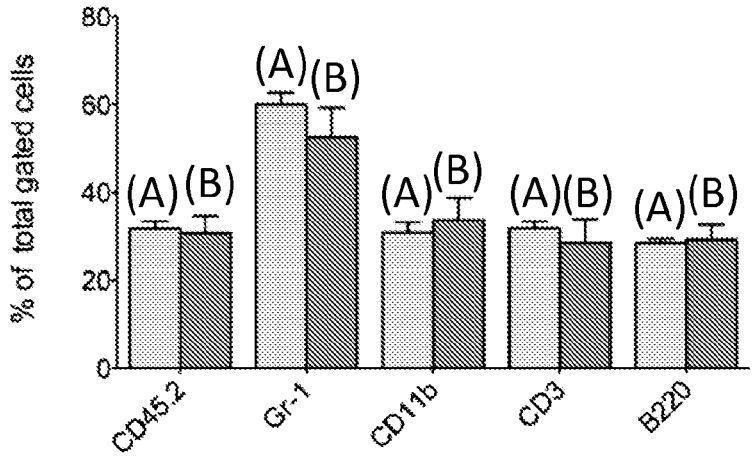

FIG. 15
AVP INDUCED RECOVERY AFTER HEMORRHAGE IS NOT AFFECTED BY SPLENECTOMY
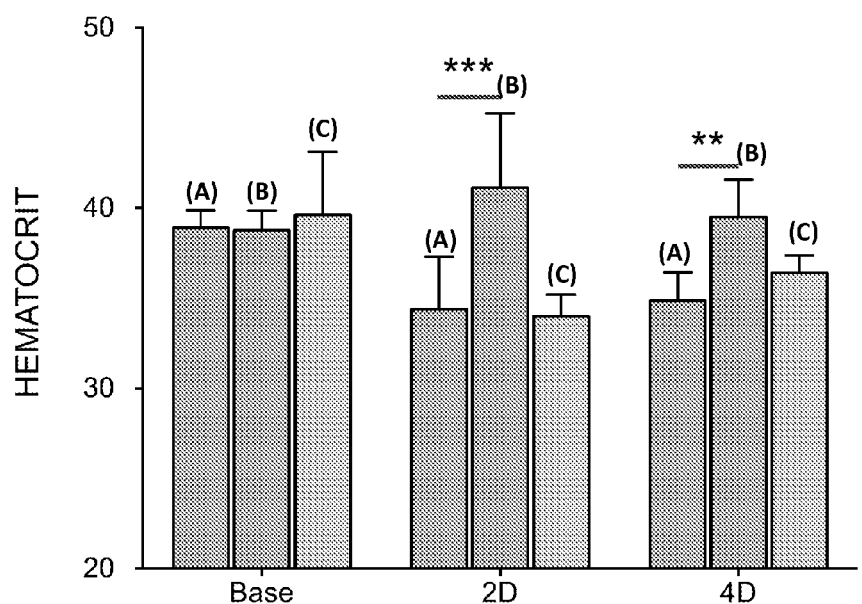
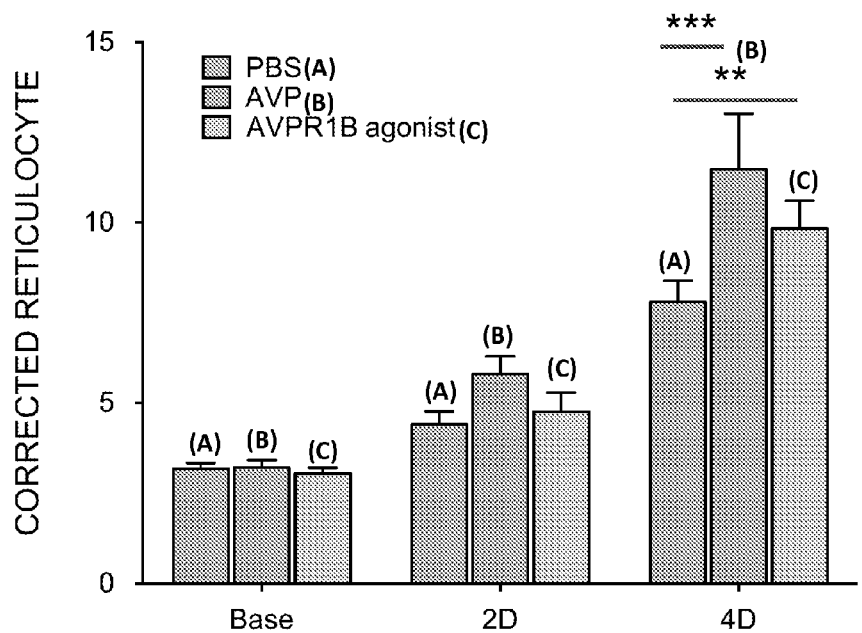

METHODS OF MODULATING ERYTHROPOIESIS WITH ARGININE VASOPRESSIN RECEPTOR 1B MOLECULES

CROSS REFERENCE TO RELATED APPLICATION

This is the U.S. National Stage of International Application No. PCT/US2014/058613, filed Oct. 1, 2014, which was published in English under PCT Article 21(2), which in turn claims the benefit of U.S. Provisional Patent Application No. 61/885,258, filed on Oct. 1, 2013, which is hereby incorporated by reference in its entirety.

FIELD

This relates to the field of erythropoiesis and in particular, to methods of modulating erythropoiesis in subjects with anemia or polycythemia with arginine vasopressin receptor 1B (AVPR1B) molecules.

BACKGROUND

Anemia is a condition in which the blood is either low in total volume or is deficient in red blood cells or hemoglobin. Anemia can occur for several reasons including hemorrhage and following chemotherapy. Erythropoietin stimulating agents are commonly administered to stimulate red blood cell production and thus, treat anemia. However, these agents often are ineffective at treating anemia because they are slow to act, are ineffective in iron deficient subjects, and can cause high blood pressure thereby increasing risk of death, heart failure, heart attack and stroke. Therefore, a need exists for methods of modulating erythropoiesis in anemic subjects, which are quicker to act, and not associated with the aforementioned side effects. Furthermore, there are cases when there are too many red blood cells made (polycythemia vera); a potentially fatal condition that has no specific treatment. A drug that could reduce the production of red cells in the bone marrow is needed.

SUMMARY

Disclosed herein are methods of modulating erythropoiesis in subjects with anemia or polycythemia with AVPR1B modulator molecules. In some embodiments, methods of inducing erythropoiesis are disclosed. For example, the method includes administering effective amounts of an AVPR1B agonist, which activates an AVPR1B receptor and induces erythropoiesis in patients suffering from anemia are disclosed. In some examples, the subject is receiving or has received chemotherapy. In some examples, the subject has or is at risk of hemorrhage. In some examples, the subject was non-responsive or had or at risk of having an adverse reaction to erythropoietin (EPO).

Also disclosed are methods of stimulating hematopoetic stem cell (HSC) proliferation. In some embodiments, the method includes administering an effective amount of an AVPR1B stimulatory molecule, such as an AVPR1B agonist, to a subject in need thereof, thereby stimulating HSC proliferation. In some examples, the subject has or is at risk of developing a condition associated anemia, such as a subject receiving chemotherapy. In some examples, the subject has or is at risk of hemorrhage.

Methods of inhibiting HSC proliferation are also disclosed. In some embodiments, the method includes administering an effective amount of an AVPR1B inhibitory molecule to a subject in need thereof, thereby inhibiting HSC proliferation. In some examples, the subject has or is at risk of developing a condition associated with excessive HSC proliferation, such as polycythemia.

The foregoing and other features and advantages of the disclosure will become more apparent from the following detailed description, which proceeds with reference to the accompanying figures.

BRIEF DESCRIPTION OF THE DRAWINGS

FIG. 1A illustrates fluorescent sorting of bone marrow cells from C57BL/6 mice using a variety of hematopoietic cell surface markers. Cells from the sorted HSPC populations described below were fixed onto microscope slides and stained with antibodies to detect members of the vasopressin and oxytocin receptor family. The methods, controls and antibodies used are given in Table 3. After immunostaining, Z series (0.2 µm) images were collected and iterative restoration was performed. Cells stained with an AVPR1B antibody are shown as an example of the results obtained. FIG. 1B provides a summary of the immunostaining using antibodies against all four receptors is given. AVPR1B was present in all populations, the most intense staining was observed in the MPP1 ($CD34^+$, $CD48^-$ and $CD150^+$) progenitor cells. FIG. 1C provides human G protein coupled receptor (GPCR) array results obtained from $CD34^+CD38^-$, $CD34^+CD38^+$, B, $CD4^+$, $CD8^+$, NK, dendritic cells and monocytes and macrophages derived from healthy donors. + indicates that the receptor was detected in a 100 ng RNA sample; ++ indicates that the receptor was detected in 40 ng and 100 ng RNA samples (n=3 donors, 40 ng and 100 ng samples from each donor). The primers for the AVPR1A were uninformative. FIGS. 1D and 1E provide histograms of fluorescent analysis showing AVPR1B and OXTR staining of $CD34^+$ cells, respectively. Isotype controls (rabbit serum and anti-rabbit Alexa647 antibody) are and unstained cells are indicated. Error bars represent means±SD ** $p<0.01$, (n=4-7) unpaired t-test. FIG. 1F provides column graphs of AVPR1B or OXTR expressing $CD34^+CD38^-$ and $CD34^+CD38^+$ cells isolated from healthy donors after 5 days of GCSF treatment and leukopheresis. Relative MFI: mean fluorescence intensity normalized to that of $CD34^+CD38^-$ population.

FIG. 2A provides hematoxylin and eosin stained histological sections from the spleens of wild-type (WT) and AVPR1B KO animals. Arrows indicate megakaryocytes. Scale bar: 50 µm. Flow cytometric analysis of megakaryocytes ($CD41^+CD61^+$ cells) in the spleens of WT and AVPR1B−/− mice (n=5 per group). Error bars represent means±SD ** $p<0.01$, unpaired t-test. FIG. 2B shows AVP and OXT increase the proliferation rate of sorted $lin^-$, $c-kit^+$ $Sca-1^+$ (LSK) mouse cells and human $CD34^+$ cells. BrdU cell proliferation assay was done using pooled bone marrow samples from 20 mice (gender and age matched), and the study was performed with three wells per condition, and 10,000 sorted cells/well. Des-GlyAVP, an inactive peptide analogue was used as a control. (The same control wells were used for AVP or OXT.). The above cell proliferation assay was repeated 3 times. Human $CD34^+$ cells were treated with AVP (in Stemspan medium and GCSF, TPO, SCF, and FLT3L at 100 ng/ml each) or OXT (in Stempsan medium with TPO, SCF, and FLT3L at 100 ng/ml each). The BrdU cell proliferation assay was done using 3 wells per condition, 5000 cells/well. The graph shows results of 1 (OXT) or 2 pooled studies (AVP). FIGS. 2C and 2D provide colony forming unit (CFU) assays of human cells from healthy donors treated with noradrenaline ($10^{-8}$ M, positive control), AVP ($10^{-6}$M, $10^{-8}$M), OXT ($10^{-6}$M, $10^{-8}$M) or a human AVPR1B specific agonist ($10^{-6}$M, $10^{-8}$M). CFU assays were done in quadruplicates, using CD34$^+$ cells from 5 different donors. CFU colony numbers/1000 plated cells were counted after 7 days and 14 days. E-CFU, erythroid colony forming unit; GM-CFU, granulocyte-macrophage colony forming unit. Error bars represent means±SD * $p<0.05$,  $p<0.01$, * $p<0.001$, unpaired t-test FIG. 3A provides results from CFU assays showing E-CFU and GM-CFU numbers/1000 plated cells. Human CD34$^+$ cells were stimulated with AVP ($10^{-8}$M), OXT ($10^{-8}$M) or as shown in FIG. 3B with a specific human AVPR1B agonist ($10^{-8}$M) with or without a Wnt pathway inhibitor dickkopf-related protein 1 (DKK1, 200 ng/ml) or an Akt inhibitor, HIMO (Akti, $10^{-8}$M) CFU assays were done in quadruplicates, studies were repeated 2 or 3 times using different donors. Error bars represent means±SD * $p<0.05$, ** $p<0.01$, unpaired t-test. FIG. 3C shows the results of Human CD34+ cells placed in multiwell chamber slides and stimulated with AVP at concentrations of $10^{-8}$, $10^{-10}$ and $10^{-12}$ (three wells per concentration) for 24 hours. The cells were then fixed with 4% paraformaldehyde and washed before immunostaining. Following permeabilization with Triton-X 100 a primary antibody to β-catenin was applied followed by a fluorescent secondary antibody. The β-catenin translocated to the nucleus at the $10^{-10}$ AVP concentration confirming the activation of the Wnt pathway. Scale: 10 μm. FIG. 3D shows the Q-PCR results showing the elevation of three key elements of the Wnt pathway in CD34$^+$ cells after being stimulated with different AVP concentrations. Using Q-PCR to detect changes in genes that reflect Wnt pathway activation, increases in CCND1, MYC and LEF1 in response to AVP stimulation were observed.

FIGS. 4A-4G show the effect of AVP administration on anemic animals. Hematocrit and corrected reticulocyte values are shown in three different models of anemia: FIG. 4A) hemorrhage, FIG. 4B) phenylhydrazine treatment (hemolytic anemia), and FIG. 4C) sublethal irradiation (suppression of the bone marrow). Peripheral blood was analyzed 2, 4 and (in the first two models) 6 days after initiation of the studies. Alzet minipumps were implanted to deliver vehicle, AVP, or (following hemorrhage) an AVPR1B agonist. Both AVP and AVPR1B agonist significantly improved recovery times in all three models. Five mice/groups were used. In FIG. 4D, sublethal irradiation model was used to determine how AVP-deficient Brattleboro (BB) rats compensate for anemia (6 BB versus 9 LE controls). In Brattleboro rats there was a significantly slower recovery. FIGS. 4E and 4F provide anemia models: FIG. 4E hemorrhage and FIG. 4F provide phenylhydrazine treatment were performed in mice that were transplanted with bone marrow from AVPR1B−/− or WT mice. In both models, the recovery of blood counts in mice that received receptor deficient marrow was slower than in controls. FIG. 4G is a flowchart summarizing the results of in vivo studies including hemorrhage or intraperitoneal (ip) injection of AVP. The decrease in the combined progenitors (MEP, CMP, GMP) is shown with open arrows. Sixteen hours following ip injection of AVP changes in BM progenitors were observed. There was a significant increase in the numbers of common myeloid progenitors (CMP), the megakaryocyte/erythrocyte progenitors (MEP), erythroblasts, and proerythroblasts. FIG. 4D are bar graphs illustrating changes in the BM progenitor populations following short-term (24 h) hemorrhage of AVPR1B deficient versus WT mice. Note the increase in the difference as the cells mature. In the studies shown in FIGS. 4D-4G, 7 to 10 mice per group were used.

FIGS. 5A-5M illustrate AVP and OXT are expressed in bone marrow stromal cells (BMSCs). BMSC derived AVP is released in response to external AVP stimulus to induce HSPC proliferation. Immunostaining of AVP and OXT in mouse (FIGS. 5A and 5B, respectively) and human (FIGS. 5C and 5D, respectively) BMSCs are provided. Scale bars: 16 μm for all panels. FIGS. 5A-5D show mouse and human BMSCs are immunopositive for AVP (FIGS. 5A and 5C) and OXT (FIGS. 5B and 5D). BMSCs from both species spontaneously release AVP (FIGS. 5E and 5G) and OXT (FIGS. 5F and 5H) in a cell-number dependent manner. AVP release from 5×10$^6$ cells mouse BMSCs into the medium was measured using a highly sensitive radioimmunoassay (RIA). Due to low levels of AVP we tried to stimulate its release using $10^{-6}$ M Calcimycin (S). Cell lysates were prepared using MPER cell lysis buffer with proteinase inhibitors. FIG. 5F shows OXT released from mouse BMSCs measured using competitive ELISA FIG. 5G shows Spontaneously released AVP from human BMSCs measured after 4 hrs of incubation in αMEM with 2% FBS by RIA assay. In FIG. 5H, bars show OXT release from hBMSCs. Cell lysates were prepared as described above. After solid phase extraction of the supernatants, RIA samples were assayed in duplicates and ELISA samples were assayed in quadruplicates. The results of 3 or more independent studies were pooled. αMEM: negative control αMEM medium with 2% FBS.  $p<0.01$, * $p<0.001$.

FIG. 5I shows ten micron thick decalcified human toe section immunostained for alkaline phosphatase and AVP; arrows point at cells that contain both markers, while arrowhead points at a cell that is AP positive but does not make AVP. The Z series was captured with an inverted Leica fluorescent microscope at 0.5 μm optical thickness and the image was analyzed after iterative restoration was performed at a 95% confidence level. FIG. 5J shows change in AVP mRNA in vivo in BMSCs isolated from mice 30-120 minutes after hemorrhage.

FIGS. 5K-5M provide BMSC derived AVP increases the proliferation of human CD34$^+$ progenitor cells (HSPCs) both with and without external AVP stimulus in vitro. FIG. 5K provides Brattleboro/LE rat BMSC and human CD34$^+$ progenitor cell co-cultures. Rat BMSCs from Brattleboro (animals that lack the ability to produce vasopressin—BB) and Long-Evans rats (LE) were co-cultured with human CD34$^+$ progenitor cells. AVP producing BMSCs induced HSPCs to proliferate better than those from BB rats (FIG. 5L) alone or stimulated with external AVP addition (FIG. 5M) BMSCs and CD34$^+$ progenitors were co-cultured but physically separated using a transwell system. BMSC derived AVP did not increase the proliferation of HSPCs in this setting indicating the need for cell-to-cell contact as in the BM in vivo.

FIG. 6 shows BMSCs release their AVP in response to increased circulating AVP to amplify the signal to induce hematopoiesis. AVP made by the hypothalamic magnocellular neurons and released into the general circulation to reach the bone marrow (BM) where bone marrow stromal cells (BMSCs), hematopoietic stem and progenitor (HSPC) cells are located. The hormones then act on their specific receptors on BMSCs to release AVP produced by these cells resulting in a significantly higher local concentration of the hormones at the surface of HSPCs. The HSPCs respond by proliferating and differentiating (possibly depending on the circulating concentrations of the two hormones) into erythroid and myeloid lineage cells. Signaling molecules in addition to AVP that are released into the blood stream in response to anemia (e.g., angiotensin II) might also stimulate BMSCs, and BMSCs might release factors in addition to AVP (e.g., OXT) that affect the proliferation and differentiation of HSPCs.

FIGS. 7A-7I illustrate AVP receptors are expressed by human and mouse HSPCs and induce their proliferation. FIG. 7A illustrate that AVPR1A, AVPR1B, and AVPR2 were amplified from human CD34$^+$ cells using RT-PCR. Lane 1: 100 bp marker, lane 2: PCR product, lane 3: negative control. FIG. 7B illustrate mRNA fragments of the AVPR1A, AVPR1B and AVPR2 were amplified from mouse bone marrow lin$^-$ c-kit$^+$ Sca-1$^+$, FACS-purified mouse cells using RT-PCR. Lane 1: 100 bp marker, lane 2: PCR product, lane 3: negative control. FIG. 7C provides histogram of fluorescent analysis show AVPR1B staining of CD34$^+$ cells (labeled C). Isotype controls (rabbit serum and anti-rabbit Alexa647 antibody, A) and unstained cells (B) are indicated. Error bars represent means±SD ** $p<0.01$, (n=4-7) unpaired t-test. Column graphs show AVPR1B expressing CD34$^+$ CD38$^-$ and CD34$^+$CD38$^+$ cells isolated from healthy donors after 5 days of GCSF treatment and leukopheresis. Relative MFI: mean fluorescence intensity normalized to that of CD34$^+$CD38$^-$ population. FIG. 7D provides immunostaining of mouse MPP cell using an antibody to AVPR1B. Z series (0.2 μm) images were collected and iterative restoration was performed using a Leica DMI6000 inverted microscope.

FIG. 7E shows AVP induces proliferation of mouse LSK cells and FIG. 7F shows that of human CD34$^+$HSPCs. FIG. 7G illustrate AVP and AVPR1B agonist stimulation induce increases in intracellular Ca$^{2+}$ concentrations in human HSPCs. FIG. 7H shows that both AVP and AVPR1B agonist induce the proliferation of HSPCs in vitro that can be blocked by a specific AVPR1B antagonist. FIG. 7I shows CFU assays of human CD34$^+$ cells from a single donor indicating that AVP induces E-CFU and GM-CFU 7 and 14 days following culture in Methocult medium. Similar results were obtained with cells from two other donors.

FIGS. 8A-8C show AVP stimulation results in the nuclear translocation of β-catenin affecting the Wnt pathway. FIG. 8A shows that human CD34$^+$ cells were placed in multiwell chamber slides and stimulated with AVP at concentrations of $10^{-8}$, $10^{-10}$ and $10^{-12}$ M (three wells per concentration) for 24 hours. The cells were then fixed with 4% paraformaldehyde and washed before immunostaining. Following permeabilization with Triton-X 100, a primary antibody to β-catenin was applied followed by a fluorescent secondary antibody. The β-catenin translocated to the nucleus at the $10^{-10}$ M AVP concentration confirming the activation of the Wnt pathway. Scale: 10 μm. FIG. 8B CFU assays showing E-CFU and GM-CFU numbers/1000 plated cells. Human CD34$^+$ cells were stimulated with AVP ($10^{-8}$M) or FIG. 8C is a specific human AVPR1B agonist (dCha$^4$AVP, $10^{-8}$M) with or without a Wnt pathway inhibitor Dickkopf-related protein 1 (DKK1, 200 ng/ml) or an Akt inhibitor, HIMO (Akti, $10^{-8}$M) CFU assays were done in quadruplicates, experiments were repeated 2 or 3 times using different donors. Error bars represent means±SD * $p<0.05$, ** $p<0.01$, unpaired t-test.

FIGS. 9A-9G provide in vivo studies demonstrating the effect of administered AVP or specific AVPR1B agonist in anemia models in mice. Hematocrit and corrected reticulocyte values are shown in three different models of anemia: FIG. 9A) hemorrhage, FIG. 9B) phenylhydrazine treatment (hemolytic anemia), and FIG. 9C) sub-lethal irradiation (suppression of the bone marrow). Peripheral blood was analyzed 2, 4 and (in the first two models) 6 days after initiation of the studies. Alzet minipumps were implanted to deliver vehicle, AVP, or (following hemorrhage) dLeu$^4$Lys$^8$-VP, an AVPR1B agonist. In FIG. 9A, the sublethal irradiation model to determine how AVP-deficient Brattleboro (BB) rats compensate for anemia (6 BB vs. 9 LE controls). In Brattleboro rats, there was a significantly slower recovery than in their WT controls (Long-Evans rats). Even 19 days after the insult, the BB rats were still very anemic, while the LE rats were in the normal range. Sixteen hours following ip injection of AVP changes in BM progenitors were observed. There was a significant increase in the numbers of common myeloid progenitors (CMP), the megakaryocyte/erythroid progenitors (MEP), erythroblasts, and proerythroblasts (FIG. 9B). FIG. 9C illustrates changes in the BM progenitor populations shown in bar graphs following short-term (24 h) hemorrhage of AVPR1B deficient vs. WT mice. Note the increase in the difference as the cells mature. In these studies, 7 to 10 mice per group were used.

The flowchart summarizes the results of in vivo studies including hemorrhage or i.p. injection of AVP. The grey arrows show the effect of hemorrhage in the AVPR1B deficient mice (compared to WT mice) and the black arrows demonstrate the changes following AVP injection. The decrease in the combined progenitors (MEP, CMP, GMP) is shown with open arrows. FIG. 9D, in hemorrhage, both AVP and dLeu$^4$Lys$^8$-VP significantly improved recovery times and FIG. 9E following irradiation of the BM, AVP administration resulted in a significantly higher hematocrit and reticulocyte value already at day 2. FIG. 9F shows a comparison between the recovery of mice with WT BM to mice with AVPR1B KO BM following hemorrhage and FIG. 9G phenylhydrazine induced anemia. In both models the WT BM showed a faster recovery than the AVPR1B KO BM.

FIGS. 10A-10C show a comparison between in vivo effects of erythropoietin (EPO) and AVP on peripheral blood recovery values and their effect on erythroid populations in the bone marrow. FIG. 10A shows the results from mice being exposed to hemorrhage and peripheral blood samples were taken at several time points. One group received 50 U/kg bodyweight EPO, and the second group received AVP. While there was no significant difference, the AVP treated group already had an increased hematocrit value at 6 hours which difference became statistically significant by 12 hours and then slowly disappeared; at day 5 there was no difference among the groups anymore. FIG. 10B shows the results from groups of mice used to test the effect of EPO neutralization on AVP induced increase in hematocrit and reticulocyte values. Interestingly, it was found that while the increase in hematocrit values due to AVP treatment did not change following EPO neutralization, the change in reticulocyte numbers seemed to be diminished. FIG. 10C illustrates the use of FACS to separate CD71 and Ter119 stained BM cells after hemorrhage and treatment with AVP or EPO to compare the ratios among the erythroid populations. EPO was found to be superior to AVP in stimulating the proliferation of the basophilic erythroblast population, but as the cells matured, AVP had a much more robust effect than EPO. FIG. 10C shows following separation of the erythroid populations, RNA was isolated and mRNA encoding the EPO and the AVP receptors was measured. Both receptor mRNAs were present in all populations—the AVPR1B increasing towards the matured cells, while the EPOR was more abundant in the earlier populations.

FIGS. 14A-14C provide bar graphs of the competitive repopulation assays. FIG. 14A, after 1,2,3,4 months peripheral blood were obtained from the retro-orbital plexus of the mice and ACK lysed blood cells were stained for CD45.1, CD45.2, Gr-1, CD11b, CD3, B220 markers and analyzed with LSRII flow cytometer. FIG. 14B, bone marrow and FIG. 14C, spleen cells were isolated 4 months after transplant and analyzed the same way.

FIG. 15 is a set of bar graphs illustrating splenectomy does not change the effect of AVP administration following hemorrhage. Three to four month old mice were splenectomized and recovered for a month. AVP was administered at the time of bleeding and blood was sampled 2 and 4 days later for hematocrit and reticulocyte measurements.

DETAILED DESCRIPTION

Figure 1A:
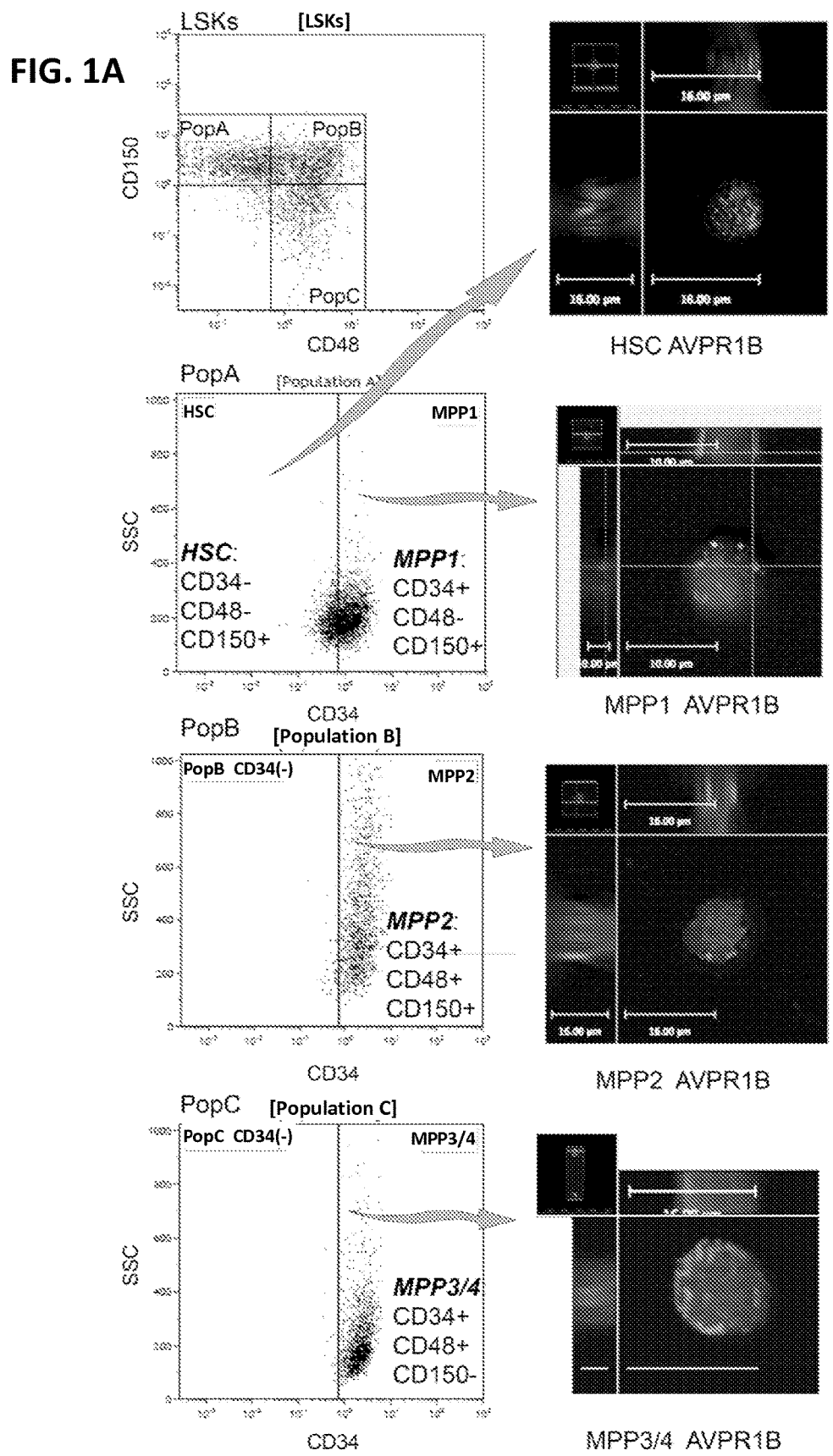
FIGS. 1A-1F illustrate vasopressin (AVPR1A, AVPR1B, AVPR2) and oxytocin (OXTR) receptors are made by hematopoietic stem and progenitor cell (HSPC) populations.

Unless otherwise explained, all technical and scientific terms used herein have the same meaning as commonly understood by one of ordinary skill in the art to which this disclosure belongs.

The singular terms "a," "an," and "the" include plural referents unless context clearly indicates otherwise. Similarly, the word "or" is intended to include "and" unless the context clearly indicates otherwise. The term "comprises" means "includes." The abbreviation, "e.g." is derived from the Latin exempli gratia, and is used herein to indicate a non-limiting example. Thus, the abbreviation "e.g." is synonymous with the term "for example."

Suitable methods and materials for the practice or testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification.

i. Introduction

Hemorrhage results in the loss of body fluid, proteins, electrolytes, and blood cells. Following hemorrhage in humans, the hypothalamic hormone arginine vasopressin (AVP) is released into the systemic circulation, AVP, also known as the antidiuretic hormone, stimulates water reabsorption by the kidneys to help restore water balance. Disclosed herein is the discovery that hematopoietic stem and progenitor cells (HSPCs) have receptors for AVP and that the peptide stimulates hematopoiesis and helps replenish not just the volume but also lost blood cells. The inventors made this discovery by inducing anemia by removing blood from animals and found that AVP administration significantly increased red blood cell (RBC) production in wild-type (WT) mice. In two additional models of anemia—one based on lysing circulating RBCs and the other based on killing bone marrow cells by irradiation—AVP administration also accelerated the restoration of RBC numbers in the blood. Following sublethal irradiation it was observed that Long-Evans rats increased RBC numbers considerably more quickly than AVP-deficient Brattleboro rats did, indicating a physiological role for endogenous AVP in hematopoiesis. Using in vitro studies with mice and human HSPCs and genetically modified mice, the AVPR1B receptor was discovered to be responsible for these effects. It was also discovered that in addition to circulating AVP there is a local source of the hormone in the bone marrow. Marrow stromal cells (MSCs) make AVP and release it onto receptors on the HSPCs that they cradle. Based on the above observations and the finding that human CD34⁺ cells proliferate in response to AVP and a specific AVPR1B agonist, methods of using a peripherally active AVPR1B agonist to induce erythropoiesis in patients suffering from anemia are disclosed.

ii. Terms

In order to facilitate review of the various embodiments of this disclosure, the following explanations of specific terms are provided:

Administer: To provide or give a subject an agent, such as an AVPR1B modulator, such as an AVPR1B agonist or antagonist, by any effective route. Administration can be systemic or local. Exemplary routes of administration include, but are not limited to, topical (e.g., transdermal), buccal, vaginal, intranasal, rectal, inhalation, ocular, otic, enteral (e.g., oral, sublingual, buccal, rectal) and parenteral (e.g., injections (such as subcutaneous, intramuscular, intradermal, intraperitoneal and intravenous) routes.

Anemia: A disorder of the blood associated with a decrease in number of red blood cells (RBCs) or less than the normal quantity of hemoglobin in the blood. Anemia can include decreased oxygen-binding ability of each hemoglobin molecule due to deformity or lack in numerical development as in some other types of hemoglobin deficiency. Because hemoglobin (found inside RBCs) normally carries oxygen from the lungs to the capillaries, anemia leads to hypoxia (lack of oxygen) in organs. Since all human cells depend on oxygen for survival, varying degrees of anemia can have a wide range of clinical consequences.

Anemia is the most common disorder of the blood. The several kinds of anemia are produced by a variety of underlying causes. It can be classified in a variety of ways, based on the morphology of RBCs, underlying etiologic mechanisms, and discernible clinical spectra, to mention a few. The three main classes include excessive blood loss (acutely such as a hemorrhage or chronically through low-volume loss), excessive blood cell destruction (hemolysis) or deficient red blood cell production (ineffective hematopoiesis).

Anemia is typically diagnosed on a complete blood count. Apart from reporting the number of red blood cells and the hemoglobin level, the automatic counters also measure the size of the red blood cells by flow cytometry, which is a tool in distinguishing between the causes of anemia. Examination of a stained blood smear using a microscope can also be helpful, and it is sometimes a necessity in regions of the world where automated analysis is less accessible. In modern counters, four parameters (RBC count, hemoglobin concentration, MCV and RDW) are measured, allowing others (hematocrit, MCH and MCHC) to be calculated, and compared to values adjusted for age and sex. Some counters estimate hematocrit from direct measurements.

WHO's Hemoglobin thresholds used to define anemia (1 g/dL=0.6206 mmol/L)

| Age or gender group | Hb threshold (g/dl) | Hb threshold (mmol/l) |
| --- | --- | --- |
| Children (0.5-5.0 yrs) | 11.0 | 6.8 |
| Children (5-12 yrs) | 11.5 | 7.1 |
| Teens (12-15 yrs) | 12.0 | 7.4 |
| Women, non-pregnant (>15 yrs) | 12.0 | 7.4 |
| Women, pregnant | 11.0 | 6.8 |
| Men (>15 yrs) | 13.0 | 8.1 |

Reticulocyte counts, and the "kinetic" approach to anemia, have become more common than in the past in the large medical centers of the United States and some other wealthy nations, in part because some automatic counters now have the capacity to include reticulocyte counts. A reticulocyte count is a quantitative measure of the bone marrow's production of new red blood cells. The reticulocyte production index is a calculation of the ratio between the level of anemia and the extent to which the reticulocyte count has risen in response. If the degree of anemia is significant, even a "normal" reticulocyte count actually may reflect an inadequate response. When the cause is not obvious, clinicians use other tests, such as: ESR, ferritin, serum iron, transferrin, RBC folate level, serum vitamin B12, hemoglobin electrophoresis, renal function tests (e.g. serum creatinine) although the tests will depend on the clinical hypothesis that is being investigated. When the diagnosis remains difficult, a bone marrow examination allows direct examination of the precursors to red cells, although is rarely used as is painful, invasive and is hence reserved for cases where severe pathology needs to be determined or excluded.

Arginine Vasopressin (AVP): A nine amino acid long peptide that is released from the brain. Most of the AVP found in blood are made by magnocellular neurons in the hypothalamic supraoptic (SON) and paraventricular (PVN) nuclei. The peptide is synthesized as a part of a precursor preprohormone that is cleaved as it is transported in axons that terminate in the posterior pituitary. The precursor yields AVP, a carrier protein, AVP-neurophysin and an N-terminal glycopeptide known as copeptin. Once it is released from nerve endings in the posterior pituitary into the bloodstream, AVP regulates salt and water homeostasis. AVP also acts within the CNS as neurotransmitters to drive a variety of social and affinitive behaviors.

Hypovolemia or hyperosmolality are strong stimuli for both synthesis and release of AVP from the posterior pituitary. Blood loss resulting in hypovolemia and hypotension is immediately followed by AVP release into the circulation. In dogs, AVP concentrations in plasma rise to a level 40 times greater than normal shortly after the onset of experimental hemorrhagic shock and gradually decline thereafter. In humans, hemorrhage may cause a 50- to a 100-fold increase in circulating AVP levels paralleled by increases in plasma concentrations of erythropoietin, catecholamines, cortisol, aldosterone, and renin/angiotensin.

AVP is disclosed herein to stimulate proliferation and differentiation of hematopoietic cells in vitro and in vivo. AVP is disclosed herein to stimulate hematopoiesis.

Arginine Vasopressin Receptor 1B (AVPR1B): A type of arginine vasopressin receptor reported herein to be involved in modulation of bone marrow stromal cells (BMSCs), hematopoietic stem and progenitor (HSPC) cells. AVPR1B is also known as vasopressin 3 receptor (VPR3) or antidiuretic hormone receptor 1b. It is a protein that in humans is encoded by the AVPR1B (arginine vasopressin receptor 1B) gene. AVPR1B belongs to the subfamily of G-protein coupled receptors. Its activity is mediated by G proteins, which stimulate a phosphatidylinositol-calcium second messenger system. It is a major contributor to homeostasis and the control of water, glucose, and salts in the blood. Arginine vasopressin has four receptors, each of which are located in different tissues and have specific functions. AVPR1B is a G-protein coupled pituitary receptor that has only recently been characterized because of its rarity.

It has been found that the 420-amino-acid sequence of the AVPR1B shared the most overall similarities with the AVP1A, AVP2 and oxytocin receptors. AVPR1B maps to chromosome region 1q32 and is a member of the vasopressin/oxytocin family subfamily. The nucleic acid sequences and amino acid sequences for AVPR1B are publically known, see for example, GenBank Accession Nos. NM_000707 and NM_011924 (Human and Mouse mRNA, respectively) and NP_000698 and NP_036054 (Human and Mouse amino acid sequences, respectively) each of which is incorporated by reference in its entirety as available on Oct. 1, 2013.

Arginine Vasopressin Receptor 1B (AVPR1B) Stimulatory Molecule: A molecule capable of stimulating the AVPR1B receptor and/or stimulating the signal transduction pathway of AVPR1B. In some examples, an AVPR1B stimulatory molecule stimulates AVPR1B and stimulates HSC proliferation.

Agonist: An AVPR1B ligand or drug that provokes a biological response upon binding to the AVPR1B, such as increasing hematopoetic (blood) stem cell proliferation and differentiation. Exemplary AVPR1B agonists are known to one of skill in the art and include, but are not limited to, those disclosed in Manning et al. (*J. Neuroendocrinology* 24:609-628, 2012) which is hereby incorporated by reference in its entirety.

Arginine Vasopressin Receptor 1B (AVPR1B) Antagonist: An AVPR1B ligand or drug that does not provoke a biological response upon binding to the AVPR1B, but blocks or dampens agonist-mediated responses, such as reducing or inhibiting excessive hematopoetic (blood) stem cell proliferation. Exemplary AVPR1B antagonists are known to one of skill in the art and include, but are not limited to, those disclosed in Manning et al., *J. Neuroendocrinology* 24:609-628, 2012 (which is hereby incorporated by reference in its entirety), Craighead et al., *Prog. Brain Res.* 170: 527-535, 2008 (which is hereby incorporated by reference in its entirety), Guillon et al., *J. Neuroendocrinol.* 16(4): 356-361, 2004 (which is hereby incorporated by reference), and/or Baker et al., *Bioorg Med Chem Lett* 21(12):3603-3607, 2011 (which is hereby incorporated by reference in its entirety). In some examples, an AVPR1B antagonist is SSR149415.

Chemotherapeutic agent or Chemotherapy: Any chemical agent with therapeutic usefulness in the treatment of diseases characterized by abnormal cell growth. Such diseases include tumors, neoplasms, and cancer. In one example, a chemotherapeutic agent is a radioactive compound. One of skill in the art can readily identify a chemotherapeutic agent of use (see for example, Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., 2000 Churchill Livingstone, Inc; Baltzer and Berkery. (eds): Oncology Pocket Guide to Chemotherapy, 2nd ed. St. Louis, Mosby-Year Book, 1995; Fischer Knobf, and Durivage (eds): The Cancer Chemotherapy Handbook, 4th ed. St. Louis, Mosby-Year Book, 1993).

Contacting: Placement in direct physical association; includes both in solid and liquid form. Contacting can occur in vitro with isolated cells or in vivo by administering the agent to a subject.

Control: A reference standard. A control can be a known value indicative of a non-anemic or an anemic subject. A difference between a test sample and a control can be a decrease or conversely an increase. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Differentiation: Refers to the process whereby relatively unspecialized cells (such as embryonic stem cells or other stem cells) acquire specialized structural and/or functional features characteristic of mature cells. Similarly, "differentiate" refers to this process. Typically, during differentiation, cellular structure alters and tissue-specific proteins appear.

Effective amount or Therapeutically effective amount: The amount of agent sufficient to prevent, treat, reduce and/or ameliorate the symptoms and/or underlying causes of any of a disorder or disease, or to increase the number of cells, such as to increase the proliferation of cells, including stem cells. In one embodiment, an "effective amount" is sufficient to reduce or eliminate a symptom of a disease, such as a sign or symptom of anemia. In another embodiment, an effective amount is an amount sufficient to overcome the disease itself. In a further example, an effective amount of an agent is an amount that produces a statistically significant increase in the number of cells in culture as compared to a control, such as a culture not treated with the agent or treated with vehicle alone.

In some examples, an effective amount is an amount of a pharmaceutical preparation that alone, or together with a pharmaceutically acceptable carrier or one or more additional therapeutic agents, induces the desired response.

The condition or disease, such as anemia, does not need to be completely inhibited for the pharmaceutical preparation to be effective. Treatment can involve only slowing the progression of the disease temporarily, but can also include halting or reversing the progression of the disease permanently. For example, a pharmaceutical preparation can alleviate one or more signs or symptoms associated with anemia by increasing stem cell proliferation by a desired amount, for example by at least 20%, at least 50%, at least 60%, at least 70%, at least 80%, at least 90%, at least 95%, at least 98%, or even at least 100%, as compared to proliferation in the absence of the pharmaceutical preparation. In other examples, a pharmaceutical preparation can alleviate one or more signs or symptoms associated with polycythemia by decreasing red blood cell production by a desired amount, for example by at least 20%, at least 50%, at least 60%, at least 70%, at least 80%, at least 90%, at least 95%, at least 98%, or even at least 100%, as compared to production in the absence of the pharmaceutical preparation. Effective amounts of the agents described herein can be determined in many different ways, such as assaying for a reduction in of one or more signs or symptoms associated with the condition, such as anemia, hemorrhage, or polycythemia in the subject or measuring the expression level of one or more molecules known to be associated with the various conditions. Effective amounts also can be determined through various in vitro, in vivo or in situ assays, including the assays described herein.

The disclosed therapeutic agents can be administered in a single dose, or in several doses, for example daily, during a course of treatment. However, the effective amount can be dependent on the source applied, the subject being treated, the severity and type of the condition being treated, and the manner of administration.

Erythrocyte: The most common type of blood cell and the vertebrate organism's principal means of delivering oxygen ($O_2$) to the body tissues via the blood flow through the circulatory system. Erythrocyte is also known as a red blood cell.

Erythropoiesis: The process by which red blood cells (erythrocytes) are produced. It is stimulated by decreased $O_2$ in circulation, which is detected by the kidneys, which then secrete the hormone erythropoietin (EPO). This hormone stimulates proliferation and differentiation of red cell precursors, which activates increased erythropoiesis in the hemopoietic tissues, ultimately producing red blood cells. In postnatal birds and mammals (including humans), this usually occurs within the red bone marrow. In the early fetus, erythropoiesis takes place in the mesodermal cells of the yolk sac. By the third or fourth month, erythropoiesis moves to the spleen and liver. After seven months, erythropoiesis occurs in the bone marrow. Increased level of physical activity can cause an increase in erythropoiesis. However, in humans with certain diseases and in some animals, erythropoiesis also occurs outside the bone marrow, within the spleen or liver. This is termed extramedullary erythropoiesis.

Erythropoietins available for use as therapeutic agents are produced by recombinant DNA technology in cell culture, and include Epogen/Procrit (epoetin alfa) and Aranesp (darbepoetin alfa); they are used in treating anemia resulting from chronic kidney disease, inflammatory bowel disease (Crohn's disease and ulcer colitis) and myelodysplasia from the treatment of cancer (chemotherapy and radiation).

Recombinant EPO has a variety of glycosylation patterns giving rise to alfa, beta, delta, and omega forms:

epoetin alfa: Darbepoetin (Aranesp); Epocept (Lupin pharma); Nanokine (Nanogen Pharmaceutical biotechnology); Epofit (Intas pharma); Epogen, made by Amgen; Epogin; Eprex, made by Janssen-Cilag; Binocrit, made by Sandoz; Procrit[19]

epoetin beta: NeoRecormon, made by Hoffmann-La Roche; Recormon; Methoxy polyethylene glycol-epoetin beta (Mircera) by Roche epoetin delta: Dynepo trademark name for an erythropoiesis stimulating protein, by Shire plc epoetin omega: Epomax epoetin zeta (biosimilar forms for epoetin alpha): Silapo (Stada); Retacrit (Hospira)

Miscellaneous: EPOTrust, made by Panacea Biotec Ltd; Erypro Safe, made by Biocon Ltd.; Repoitin, made by Serum Institute of India Limited; Vintor, made by Emcure Pharmaceuticals; Erykine, made by Intas Biopharmaceutica; Wepox, made by Wockhardt Biotech; Espogen, made by LG life sciences; ReliPoietin, made by Reliance Life Sciences; Shanpoietin, made by Shantha Biotechnics Ltd; Zyrop, made by Cadila Healthcare Ltd.; EPIAO (rHuEPO), made by Shenyang Sunshine Pharmaceutical Co. LTD. China; Darbepoetin alfa is a form created by five substitutions (Asn-57, Thr-59, Val-114, Asn-115 and Thr-117) that create two new N-glycosylation sites; and Novel erythropoiesis-stimulating protein (NESP; Macdougall IC (July 2000). "Novel erythropoiesis stimulating protein". Semin. Nephrol. 20 (4): 375-81. PMID 10928340).

Hemorrhage: The loss of blood or blood escaping from the circulatory system. Hemorrhaging (bleeding) can arise due to either traumatic injury, underlying medical condition, or a combination thereof.

Inhibit: To decrease, limit or block the action or function of a molecule. In an example, the stimulation of stem cell, such as HSC proliferation and/or differentiation or an inhibitor of an AVPR1B receptor activity or molecules involved in intracellular signaling triggered by AVPR1B receptor activation which induce stem cell proliferation and/or differentiation is decreased.

Inhibiting a disease or condition: A phrase referring to reducing the development of a disease or condition, for example, in a subject who is at risk for a disease or who has a particular disease. Particular methods of the present disclosure provide methods for inhibiting anemia.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of the compositions herein disclosed. For example an AVPR1B antagonist or agonist can be administered in the presence of one or more pharmaceutically acceptable carriers, including a non-natural or natural pharmaceutically acceptable carrier molecule.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (for instance, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. Embodiments of other pharmaceutical compositions can be prepared with conventional pharmaceutically acceptable carriers, adjuvants, and counter-ions, as would be known to those of skill in the art. The compositions in some embodiments are in the form of a unit dose in solid, semi-solid, and liquid dosage forms, such as tablets, pills, capsules, lozenges, powders, liquid solutions, or suspensions.

Polycythemia: A disease state in which the proportion of blood volume that is occupied by red blood cells increases. Blood volume proportions can be measured as hematocrit level. It can be due to an increase in the number of red blood cells ("absolute polycythemia") or to a decrease in the volume of plasma ("relative polycythemia"). Polycythemia is sometimes called erythrocytosis, but the terms are not synonymous because polycythemia refers to any increase in red blood cells, whereas erythrocytosis only refers to a documented increase of red cell mass.

Stem cell: A cell that can generate a fully differentiated functional cell of a more than one given cell type. The role of stem cells in vivo is to replace cells that are destroyed during the normal life of an animal. Generally, stem cells can divide without limit and are totipotent or pluripotent. After division, the stem cell may remain as a stem cell, become a precursor cell, or proceed to terminal differentiation. A nervous system (NS) stem cell is, for example, a cell of the central nervous system that can self-renew and can generate astrocytes, neurons and oligodendrocytes.

A hematopoetic stem cell (HSC) is, for example, a cell that gives rise to all other blood cells. They give rise to the myeloid (monocytes and macrophages, neutrophils, basophils, eosinophils, erythrocytes, megakaryocytes/platelets, dendritic cells), and lymphoid lineages (T-cells, B-cells, NK-cells). The definition of hematopoietic stem cells has changed in the last two decades. The hematopoietic tissue contains cells with long-term and short-term regeneration capacities and committed multipotent, oligopotent, and unipotent progenitors. HSCs constitute 1:10.000 of cells in myeloid tissue. HSCs are a heterogeneous population. Three classes of stem cells exist, distinguished by their ratio of lymphoid to myeloid progeny (L/M) in blood. Myeloid-biased (My-bi) HSC have low L/M ratio ($>0$, $<3$), whereas lymphoid-biased (Ly-bi) HSC show a large ratio ($>10$). The third category consists of the balanced (Bala) HSC for which $3 \leq L/M \leq 10$. Only the myeloid-biased and -balanced HSCs have durable self-renewal properties. In addition, serial transplantation studies have shown that each subtype preferentially re-creates its blood cell type distribution, suggesting an inherited epigenetic program for each subtype. HSCs can be identified and characterized based upon morphology, presence and/or absence of particular markers and functional assays, such as the cobblestone area-forming cell (CAFC) assay.

A bone marrow stem cell is, for example, an adult, mesoderm-derived cell that is capable of generating cells of mesenchymal lineages, typically of two or more mesenchymal lineages, e.g., osteocytic (bone), chondrocytic (cartilage), myocytic (muscle), tendonocytic (tendon), fibroblastic (connective tissue), adipocytic (fat) and stromogenic (marrow stroma) lineage. Bone marrow stem cells are present in or (partly) isolated from a sample of bone marrow. A sample of bone marrow may be obtained, e.g., from iliac crest, femora, tibiae, spine, rib or other medullar spaces of a subject. Bone marrow stem cells encompass any and all subtypes thereof, such as without limitation, "rapidly self-renewing cells" RS-1 or RS-2 as described in Colter et al. 2000 (PNAS 97(7): 3213-8); "side population" (SP) cells as described by Goodell et al. 1997 (Nat Med 3(12): 1337-45); osteogenic precursor (OP) cells which are initially identified by their low density (e.g., upon density gradient centrifugation), non-adherent nature and low-level of expression of osteogenic markers (as described by Long et al. 1995. J Clin Invest. 95(2): 881-7; U.S. Pat. No. 5,972,703); primitive precursor cells which can generate cells of both the haematopoietic and non-haematopoietic lineages as described by Krause et al. 2001 (Cell 105: 369-377) and Dominici et al. 2004. (PNAS 101(32): 11761-6); and others.

Subject: Living multi-cellular vertebrate organisms, a category that includes human and non-human mammals.

Under conditions sufficient to: A phrase that is used to describe any environment that permits the desired activity.

iii. Methods of Use

Disclosed herein are methods of modulating erythropoiesis in subjects with anemia or polycythemia with AVPR1B molecules. In some embodiments, methods of stimulating AVPR1B receptors are disclosed, such as for inducing erythropoiesis. In some examples, methods of inhibiting AVPR1B receptors or receptor activity are disclosed, such as in a subject that has or is at risk of developing polycythemia. In some examples, the disclosed methods are used to treat a subject with anemia, hemorrhage or polycythemia.

(1) Methods of Stimulating AVPR1B Receptors

Methods of stimulating AVPR1B receptors are disclosed. In some examples, the method includes administering an effective amount of an AVPR1B agonist which activates an AVPR1B receptor and induces erythropoiesis in patients suffering from anemia resulting from a number of conditions, including, but not limited to, chronic kidney disease, inflammatory bowel disease (Crohn's disease and ulcer colitis) and/or myelodysplasia from the treatment of cancer (chemotherapy and radiation). In some examples, the subject is receiving or has received chemotherapy. In some examples, the subject has or is at risk of acquiring disorders or is undergoing drug treatments characterized by hemolysis. In some examples, the subject has or is at risk of hemorrhage. In some examples, the subject has or is at risk of exposure to radiation, such as at nuclear reactor accidents/meltdowns or during war. In some examples, the subject is at risk of hemorrhage due to an injury experience at a trauma scene, such as a car accident, suicide bombing, terrorist attack, bombing, or during war. For example, the disclosed methods include administering an effective amount of an AVPR1B agonist in the field and help people survive injuries including exposure to radiation or mass bleeding that otherwise would be lethal. Also, in irradiation injury, a AVPR1B agonist can be administered to enhance red blood cell manufacturing from quiescent progenitors that are much less affected by radiation.

In some examples, the method includes administering an effective amount of the AVPR1B receptor stimulatory molecule followed by administering one or more additional erythropoiesis stimulatory molecules. In some examples, the method includes administering an effective amount of the AVPR1B receptor stimulatory molecule prior to administering one or more additional erythropoiesis stimulatory molecules, such as erythropoietin. In some examples, the additional erythropoiesis stimulatory molecule is administered at least one hour after the administration of the AVPR1B receptor stimulatory molecule, such as between 2 and 96 hours, 12 and 72 hours, 24 and 48 hours, including 1 hour, 2 hours, 3 hours, 4 hours, 5 hours, 6 hours, 7 hours, 8 hours, 9 hours, 10 hours, 11 hours, 12 hours, 15 hours, 18 hours, 24 hours, 30 hours 36 hours, 48 hours, 72 hours or 96 hours. In some examples, the AVPR1B receptor stimulatory molecule and one or more additional erythropoiesis stimulatory molecules are co-administered. In some examples, the method includes selecting a subject, such as selecting a subject at risk of acquiring or having anemia, prior to administering the effective amount of one or more AVPR1B stimulatory molecules.

Also disclosed are methods of stimulating stem cells, such as HSC or bone marrow stem cell proliferation and/or differentiation. In some embodiments, the method includes administering an effective amount of an AVPR1B stimulatory molecule to a subject in need thereof, thereby stimulating HSC proliferation. In some examples, the subject has or is at risk of developing a condition associated anemia, such as anemia resulting from chronic kidney disease, inflammatory bowel disease (Crohn's disease and ulcer colitis) and/or myelodysplasia from the treatment of cancer (chemotherapy and radiation). In some examples, the subject is receiving or has received chemotherapy. In some examples, the subject has or is at risk of hemorrhage. In some examples, the subject has or is at risk of exposure to radiation, such as at nuclear reactor accidents/meltdowns or during war. In some examples, the subject is at risk of hemorrhage due to an injury experience at a trauma scene, such as a car accident, suicide bombing, terrorist attack, bombing, or during war. For example, the disclosed methods include administering an effective amount of an AVPR1B agonist in the field and help people survive injuries including exposure to radiation or mass bleeding that otherwise would be lethal.

In some examples, the method includes selecting a subject, such as selecting a subject at risk of acquiring or having anemia, a condition associated with anemia, or hemorrhage. In some examples, the method includes administering an effective amount of the AVPR1B receptor stimulatory molecule followed by administering one or more additional erythropoiesis stimulatory molecules. In some examples, the method includes administering an effective amount of the AVPR1B receptor stimulatory molecule prior to administering one or more additional erythropoiesis stimulatory molecules, such as erythropoietin. In some examples, the additional erythropoiesis stimulatory molecule is administered at least one hour after the administration of the AVPR1B receptor stimulatory molecule, such as between 2 and 96 hours, 12 and 72 hours, 24 and 48 hours, including 1 hour, 2 hours, 3 hours, 4 hours, 5 hours, 6 hours, 7 hours, 8 hours, 9 hours, 10 hours, 11 hours, 12 hours, 15 hours, 18 hours, 24 hours, 30 hours 36 hours, 48 hours, 72 hours or 96 hours. In some examples, the AVPR1B receptor stimulatory molecule and one or more additional erythropoiesis stimulatory molecules are co-administered. In one particular example, the method includes administering an effective amount of the AVPR1B receptor stimulatory molecule for 12 to 72 hours followed by administering one or more additional erythropoiesis stimulatory molecules, such as erythropoietin.

a. AVPR1B Stimulatory Molecules

In some examples, the AVPR1B stimulatory molecule is an AVPR1B receptor agonist. Exemplary AVPR1B agonists are known to one of skill in the art and include, but are not limited to, those disclosed in Manning et al., *J. Neuroendocrinology* 24:609-628, 2012, Manning et al., *Prog. Brain Res.* 170: 473-512, 2008 or Craighead et al., *Prog. Brain Res.* 170: 527-535, 2008 (each of which is hereby incorporated by reference in its entirety). In some examples, the AVPR1B receptor agonist is an agonist listed in Table 1. In some examples, the AVPR1B receptor agonist is d[Leu4, Lys8]-VP. In some examples, the AVPR1B receptor agonist is peripherally active (i.e., the agonist has no effect on the central nervous system).

b. Additional Erythropoiesis Stimulatory Molecules

In some examples, an additional erythropoiesis stimulatory molecule includes erythropoietin, including erythropoietins available for use as therapeutic agents and produced by recombinant DNA technology in cell culture, which include Epogen/Procrit (epoetin alfa) and Aranesp (darbepoetin alfa). In some examples, one or more additional erythropoiesis stimulatory molecules includes one or more recombinant EPO including one or more of epoetin alfa (Darbepoetin (Aranesp); Epocept (Lupin pharma); Nanokine (Nanogen Pharmaceutical biotechnology); Epofit (Intas pharma); Epogen, made by Amgen; Epogin; Eprex, made by Janssen-Cilag; Binocrit, made by Sandoz; Procrit), epoetin beta (NeoRecormon, made by Hoffmann-La Roche; Recormon; Methoxy polyethylene glycol-epoetin beta (Mircera) by Roche), epoetin delta (Dynepo trademark name for an erythropoiesis stimulating protein, by Shire plc), epoetin omega: (Epomax), epoetin zeta ((biosimilar forms for epoetin alpha): Silapo (Stada); Retacrit (Hospira)), EPOTrust (made by Panacea Biotec Ltd), Erypro Safe (made by Biocon Ltd.), Repoitin (made by Serum Institute of India Limited) Vintor (made by Emcure Pharmaceuticals); Erykine (made by Intas Biopharmaceutica), Wepox (made by Wockhardt Biotech), Espogen (made by LG life sciences), ReliPoietin (made by Reliance Life Sciences), Shanpoietin (made by Shantha Biotechnics Ltd), Zyrop (made by Cadila Healthcare Ltd.), EPIAO (rHuEPO, made by Shenyang Sunshine Pharmaceutical Co. LTD. China), NESP (Macdougall IC (July 2000) "Novel erythropoiesis stimulating protein" Semin. Nephrol. 20 (4): 375-81. PMID 10928340), or erythropoiesis stimulating molecules disclosed in Craighead et al., *Prog. Brain Res.* 170: 527-535, 2008 (which is hereby incorporated by reference in its entirety), Guillon et al., *J. Neuroendocrinol.* 16(4): 356-361, 2004 (which is hereby incorporated by reference), Manning et al., *J. Neuroendocrinology* 24:609-628, 2012 (which is hereby incorporated by reference in its entirety), or Baker et al., *Bioorg Med Chem Lett* 21(12):3603-3607, 2011 (which is hereby incorporated by reference in its entirety).

(2) Methods of Inhibiting AVPR1B Receptors

Methods of inhibiting hematopoetic stem cell (HSC) proliferation and differentiation are also disclosed. In some embodiments, the method includes administering an effective amount of an AVPR1B inhibitory molecule to a subject in need thereof, thereby inhibiting HSC proliferation. In some examples, the subject has or is at risk of developing a condition associated with excessive HSC proliferation. In some examples, the subject has or is at risk of developing polycythemia. In some examples, an AVPR1B inhibitory molecule is an AVPR1B antagonist. Exemplary AVPR1B antagonists are known to one of skill in the art and include, but are not limited to, those disclosed in Manning et al., *J. Neuroendocrinology* 24:609-628, 2012 (which is hereby incorporated by reference in its entirety), Craighead et al., *Prog. Brain Res.* 170: 527-535, 2008 (which is hereby incorporated by reference in its entirety), Guillon et al., *J. Neuroendocrinol.* 16(4): 356-361, 2004 (which is hereby incorporated by reference), and/or Baker et al., *Bioorg Med Chem Lett* 21(12):3603-3607, 2011 (which is hereby incorporated by reference in its entirety). In some examples, an AVPR1B antagonist is SSR149415. In some examples, the method includes selecting a subject, such as selecting a subject at risk of acquiring or having polycythemia prior to administering the effective amount of one or more AVPR1B inhibitory molecules.

In some examples, the method includes administering an effective amount of the AVPR1B receptor inhibitory molecule prior to administering one or more additional erythropoiesis inhibitory molecules, such as a low dose of aspirin, hydroxyurea or pegylated interferon. It is noted that hydroxyurea has been used for treating polycythemia since the late 1800s, but it has severe side effects. Thus, a specific drug capable of inhibiting the proliferation of erythroid progenitors, such as an AVPR1B inhibitory molecule, is a much more desirable method of treating polycythemia. In particular embodiments, methods of reducing erythroid lineage proliferation are disclosed including administering an effective amount of the AVPR1B receptor inhibitory molecule polycythemia.

In some examples, this method includes administering an effective amount of the AVPR1B receptor inhibitory molecule to a subject that did not respond to phlebotomy or in addition to phlebotomy.

In some examples, the additional erythropoiesis inhibitory molecule is administered at least one hour after the administration of the AVPR1B receptor inhibitory molecule, such as between 2 and 96 hours, 12 and 72 hours, 24 and 48 hours, including 1 hour, 2 hours, 3 hours, 4 hours, 5 hours, 6 hours, 7 hours, 8 hours, 9 hours, 10 hours, 11 hours, 12 hours, 15 hours, 18 hours, 24 hours, 30 hours 36 hours, 48 hours, 72 hours or 96 hours. In some examples, the AVPR1B receptor inhibitory molecule and one or more additional erythropoiesis inhibitory molecules are co-administered. In one particular example, the method includes administering an effective amount of the AVPR1B receptor inhibitory molecule for 12 to 72 hours followed by administering one or more additional erythropoiesis inhibitory molecules.

iv. Administration of an Effective Amount of an AVPR1B Molecule

For any of the disclosed methods, an effective amount of an AVPR1B modulatory molecule is one when administered by a particular route and concentration induces the desired response (e.g., stimulating cell proliferation and/or differentiation, treatment of anemia, hemorrhaging, or polycythemia).

a. Administration Routes, Formulations and Concentrations

Methods of administration of the disclosed AVPR1B modulatory molecules are routine, and can be determined by a skilled clinician. The disclosed AVPR1B modulatory molecules or other therapeutic substance could be in general administered topically (in a patch), nasally, intravenously, orally, intramuscularly, parenterally or as implants, but even rectal or vaginal use is possible in principle. The disclosed AVPR1B modulatory molecules also may be administered to a subject using a combination of these techniques.

Suitable solid or liquid pharmaceutical preparation forms are, for example, aerosols, (micro)capsules, creams, drops, drops or injectable solution in ampoule form, emulsions, granules, powders, suppositories, suspensions, syrups, tablets, coated tablets, and also preparations with protracted release of active compounds (such as in a skin patch), in whose preparation excipients and additives and/or auxiliaries such as binders, coating agents, disintegrants, flavorings, lubricants, solubilizers, sweeteners, or swelling agents are customarily used as described above. The pharmaceutical agents are suitable for use in a variety of drug delivery systems. For a brief review of various methods for drug delivery, see Langer, "New Methods of Drug Delivery," Science 249:1527-1533 (1990), incorporated by reference herein to the extent not inconsistent with the present disclosure.

The disclosed AVPR1B modulatory molecules agents or other therapeutic agents of the present disclosure can be formulated into therapeutically-active pharmaceutical agents that can be administered to a subject parenterally or orally. Parenteral administration routes include, but are not limited to epidermal, intraarterial, intramuscular (IM and depot IM), intraperitoneal (IP), intravenous (IV), intrasternal injection or infusion techniques, intranasal (inhalation), intrathecal, injection into the stomach, subcutaneous injections (subcutaneous (SQ and depot SQ), transdermal, topical, and ophthalmic.

The disclosed AVPR1B modulatory molecules or other therapeutic agents can be mixed or combined with suitable pharmaceutically acceptable excipients to prepare pharmaceutical agents. Pharmaceutically acceptable excipients include, but are not limited to, alumina, aluminum stearate, buffers (such as phosphates), glycine, ion exchangers (such as to help control release of charged substances), lecithin, partial glyceride mixtures of saturated vegetable fatty acids, potassium sorbate, serum proteins (such as human serum albumin), sorbic acid, water, salts or electrolytes such as cellulose-based substances, colloidal silica, disodium hydrogen phosphate, magnesium trisilicate, polyacrylates, polyalkylene glycols, such as polyethylene glycol, polyethylene-polyoxypropylene-block polymers, polyvinyl pyrrolidone, potassium hydrogen phosphate, protamine sulfate, group 1 halide salts such as sodium chloride, sodium carboxymethylcellulose, waxes, wool fat, and zinc salts, for example. Liposomal suspensions may also be suitable as pharmaceutically acceptable carriers.

Upon mixing or addition of one or more disclosed AVPR1B modulatory molecules and/or or other therapeutic agents, the resulting mixture may be a solid, solution, suspension, emulsion, or the like. These may be prepared according to methods known to those of ordinary skill in the art. The form of the resulting mixture depends upon a number of factors, including the intended mode of administration and the solubility of the agent in the selected carrier. Pharmaceutical carriers suitable for administration of the disclosed AVPR1B modulatory molecules or other therapeutic agents include any such carriers known to be suitable for the particular mode of administration. In addition, the disclosed AVPR1B modulatory molecules or other therapeutic substance can also be mixed with other inactive or active materials that do not impair the desired action, or with materials that supplement the desired action, or have another action.

Methods for solubilizing may be used where the agents exhibit insufficient solubility in a carrier. Such methods are known and include, but are not limited to, dissolution in aqueous sodium bicarbonate, using cosolvents such as dimethylsulfoxide (DMSO), and using surfactants such as TWEEN® (ICI Americas, Inc., Wilmington, Del.).

The disclosed AVPR1B modulatory molecules or other therapeutic agents can be prepared with carriers that protect them against rapid elimination from the body, such as coatings or time-release formulations. Such carriers include controlled release formulations, such as, but not limited to, microencapsulated delivery systems. A disclosed AVPR1B modulatory molecule or other therapeutic agent is included in the pharmaceutically acceptable carrier in an amount sufficient to exert a therapeutically useful effect, typically in an amount to avoid undesired side effects, on the treated subject. The therapeutically effective concentration may be determined empirically by testing the compounds in known in vitro and in vivo model systems for the treated condition. For example, mouse models may be used to determine effective amounts or concentrations that can then be translated to other subjects, such as humans, as known in the art.

Injectable solutions or suspensions can be formulated, using suitable non-toxic, parenterally-acceptable diluents or solvents, such as 1,3-butanediol, isotonic sodium chloride solution, mannitol, Ringer's solution, saline solution, or water; or suitable dispersing or wetting and suspending agents, such as sterile, bland, fixed oils, including synthetic mono- or diglycerides, and fatty acids, including oleic acid; a naturally occurring vegetable oil such as coconut oil, cottonseed oil, peanut oil, sesame oil, and the like; glycerine; polyethylene glycol; propylene glycol; or other synthetic solvent; antimicrobial agents such as benzyl alcohol and methyl parabens; antioxidants such as ascorbic acid and sodium bisulfite; buffers such as acetates, citrates, and phosphates; chelating agents such as ethylenediaminetetraacetic acid (EDTA); agents for the adjustment of tonicity such as sodium chloride and dextrose; and combinations thereof. Parenteral preparations can be enclosed in ampoules, disposable syringes, or multiple dose vials made of glass, plastic, or other suitable material. Buffers, preservatives, antioxidants, and the like can be incorporated as required. Where administered intravenously, suitable carriers include physiological saline, phosphate-buffered saline (PBS), and solutions containing thickening and solubilizing agents such as glucose, polyethylene glycol, polypropyleneglycol, and mixtures thereof. Liposomal suspensions, including tissue-targeted liposomes, may also be suitable as pharmaceutically acceptable carriers.

For topical application, one or more disclosed AVPR1B modulatory molecules, or other therapeutic agent may be made up into a cream, lotion, ointment, solution, or suspension in a suitable aqueous or non-aqueous carrier. Topical application can also be accomplished by transdermal patches or bandages, which include the therapeutic substance. Additives can also be included, e.g., buffers such as sodium metabisulphite or disodium edetate; preservatives such as bactericidal and fungicidal agents, including phenyl mercuric acetate or nitrate, benzalkonium chloride, or chlorhexidine; and thickening agents, such as hypromellose.

If the disclosed AVPR1B modulatory molecule, or other therapeutic agent is administered orally as a suspension, the pharmaceutical agents can be prepared according to techniques well known in the art of pharmaceutical formulation and may contain a suspending agent, such as alginic acid or sodium alginate, bulking agent, such as microcrystalline cellulose, a viscosity enhancer, such as methylcellulose, and sweeteners/flavoring agents. Oral liquid preparations can contain conventional additives such as suspending agents, e.g., gelatin, glucose syrup, hydrogenated edible fats, methyl cellulose, sorbitol, and syrup; emulsifying agents, e.g., acacia, lecithin, or sorbitan monooleate; non-aqueous carriers (including edible oils), e.g., almond oil, fractionated coconut oil, oily esters such as glycerine, propylene glycol, or ethyl alcohol; preservatives such as methyl or propyl p-hydroxybenzoate or sorbic acid; and, if desired, conventional flavoring or coloring agents. When formulated as immediate release tablets, these agents can contain dicalcium phosphate, lactose, magnesium stearate, microcrystalline cellulose, and starch and/or other binders, diluents, disintegrants, excipients, extenders, and lubricants.

If oral administration is desired, one or more disclosed AVPR1B modulatory molecules, or other therapeutic substances can be provided in a composition that protects it from the acidic environment of the stomach. For example, the disclosed AVPR1B modulatory molecules or other therapeutic agents can be formulated with an enteric coating that maintains its integrity in the stomach and releases the active compound in the intestine. The disclosed AVPR1B modulatory molecules, or other therapeutic agent can also be formulated in combination with an antacid or other such ingredient.

Oral compositions generally include an inert diluent or an edible carrier and can be compressed into tablets or enclosed in gelatin capsules. For the purpose of oral therapeutic administration, one or more of the disclosed modulatory molecules, or other therapeutic substances can be incorporated with excipients and used in the form of capsules, tablets, or troches. Pharmaceutically compatible adjuvant materials or binding agents can be included as part of the composition.

The capsules, pills, tablets, troches, and the like can contain any of the following ingredients or compounds of a similar nature: a binder such as, but not limited to, acacia, corn starch, gelatin, gum tragacanth, polyvinylpyrrolidone, or sorbitol; a filler such as calcium phosphate, glycine, lactose, microcrystalline cellulose, or starch; a disintegrating agent such as, but not limited to, alginic acid and corn starch; a lubricant such as, but not limited to, magnesium stearate, polyethylene glycol, silica, or talc; a gildant, such as, but not limited to, colloidal silicon dioxide; a sweetening agent such as sucrose or saccharin; disintegrants such as potato starch; dispersing or wetting agents such as sodium lauryl sulfate; and a flavoring agent such as peppermint, methyl salicylate, or fruit flavoring.

When the dosage unit form is a capsule, it can contain, in addition to material of the above type, a liquid carrier, such as a fatty oil. In addition, dosage unit forms can contain various other materials that modify the physical form of the dosage unit, for example, coatings of sugar and other enteric agents. One or more of the disclosed modulatory agents, or other therapeutic agent can also be administered as a component of an elixir, suspension, syrup, wafer, tea, chewing gum, or the like. A syrup may contain, in addition to the active compounds, sucrose or glycerin as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, they can be of the sustained release type so that the compounds need to be administered less frequently.

In some examples, one or more of the disclosed AVPR1B modulatory molecules and/or a therapeutic agent is intraperitoneal injected into the peritoneum of a subject. When particular methods of the present disclosure are used to treat one or more signs or symptoms associated with anemia, hemorrhaging, or polycythemia, the subject is typically treated a sufficient period of time to reduce, inhibit or prevent one or more signs or symptoms associated with such conditions. For example, the subject may be treated at least 1 hour, such as for 2 to 96 hours, for 12 to 72 hours, for 24 to 48 hours, including 1 hour, 2 hours, 3 hours, 4 hours, 5 hours, 6 hours, 7 hours, 8 hours, 9 hours, 10 hours, 11 hours, 12 hours, 15 hours, 18 hours, 24 hours, 30 hours 36 hours, 48 hours, 72 hours or 96 hours. In some examples, the subject is treated for a day, a week, a month or longer. Treatment can be initiated prior to the on-set of a particular condition, such as anemia, to a subject at risk of acquiring anemia, such as a subject undergoing chemotherapy. In some implementations, the treatment is initiated between about 1 and about 96 hours following chemotherapy treatment, such as between about 24 and about 48 hours following chemotherapy. In some cases, a single administration of the substance is effective to provide the desired therapeutic effect. In further examples, additional administrations are provided in order to achieve the desired therapeutic effect.

In some examples, the method includes administering an effective amount of the AVPR1B receptor stimulatory molecule prior to administering one or more additional erythropoiesis stimulatory molecules, such as erythropoietin. In some examples, the additional erythropoiesis stimulatory molecule is administered at least one hour after the administration of the AVPR1B receptor stimulatory molecule, such as between 2 and 96 hours, 12 and 72 hours, 24 and 48 hours, including 1 hour, 2 hours, 3 hours, 4 hours, 5 hours, 6 hours, 7 hours, 8 hours, 9 hours, 10 hours, 11 hours, 12 hours, 15 hours, 18 hours, 24 hours, 30 hours 36 hours, 48 hours, 72 hours or 96 hours after the administration of the AVPR1B receptor stimulatory molecule.

Amounts effective for various therapeutic treatments of the present disclosure may, of course, depend on the severity of the condition/disease and the weight and general state of the subject, as well as the absorption, inactivation, and excretion rates of the therapeutically-active compound or component, the dosage schedule, and amount administered, as well as other factors known to those of ordinary skill in the art. It also should be apparent to one of ordinary skill in the art that the exact dosage and frequency of administration will depend on the particular AVPR1B receptor modulatory molecule, or other therapeutic substance being administered, the particular condition being treated, the severity of the condition being treated, the age, weight, general physical condition of the particular subject, and other medication the subject may be taking. Typically, dosages used in vitro may provide useful guidance in the amounts useful for in vivo administration of the pharmaceutical composition, and animal models may be used to determine effective dosages for treatment of particular disorders. For example, mouse models may be used to determine effective dosages that can then be translated to dosage amount for other subjects, such as humans, as known in the art. Various considerations in dosage determination are described, e.g., in Gilman et al., eds., *Goodman And Gilman's: The Pharmacological Bases of Therapeutics,* 8th ed., Pergamon Press (1990); and *Remington's Pharmaceutical Sciences,* 17th ed., Mack Publishing Co., Easton, Pa. (1990), each of which is herein incorporated by reference to the extent not inconsistent with the present disclosure.

Particular dosage regimens can be tailored to a particular subject, condition to be treated or desired result. For example, an initial treatment regimen can be applied to arrest the condition. Such initial treatment regimen may include administering a higher dosage of one or more of the disclosed modulatory molecules, or administering such material more frequently, such as daily. After a desired therapeutic result has been obtained, such as a desired level of HSC proliferation, a second treatment regimen may be applied, such as administering a lower dosage of one or more of the disclosed modulatory agents or administering such material less frequently, such as monthly, bi-monthly, quarterly, or semi-annually. In such cases, the second regimen may serve as a "booster" to restore or maintain a desired level of red blood cell production or HSC proliferation.

In specific examples, the one or more disclosed AVPR1B modulatory molecules is administered to a subject in an amount sufficient to provide a dose of the agent of between about 10 fmol/g and about 500 nmol/g, such as between about 2 nmol/g and about 20 nmol/g or between about 2 nmol/g and about 10 nmol/g. In additional examples, an AVPR1B modulatory molecule is administered to a subject in an amount sufficient to provide a dose of between about 0.01 μg/kg and about 1000 mg/kg or between about 0.1 mg/kg and about 1000 mg/kg, in particular examples this amount is provided per day or per week. In another example, a disclosed AVPR1B modulatory molecule is administered to a subject in an amount sufficient to provide a dose of agent of between about 0.2 mg/kg and about 2 mg/kg. In further examples, the AVPR1B modulatory molecule is administered to a subject in an amount sufficient to provide a concentration of the AVPR1B modulatory molecule in the administrated material of between about 5 nM and about 500 nM, such as between about 50 nM and about 200 nm, or about 100 nM. In other examples, the AVPR1B modulatory molecule is administered to a subject between about 500 μg/ml and about 1 μg/ml, such as about 300 μg/ml and about 3 μg/ml, about 200 μg/ml and about 20 μg/ml, including 500 μg/ml, 400 μg/ml, 300 μg/ml, 250 μg/ml, 200 μg/ml, 150 μg/ml, 100 μg/ml, 50 μg/ml, 25 μg/ml, 12.5 μg/ml, 6.25 μg/ml, 3.125 μg/ml, 2.5 μg/ml and 1.25 μg/ml.

In some examples, the specific concentration of the AVPR1B modulatory molecule administered is determined based upon receptor affinity and bioavailability.

In some implementations, the effective amount of one or more of the disclosed AVPR1B modulatory molecules is administered as a single dose per time period, such as every 12 hours, day, week, or month can be divided into at least two unit dosages for administration over a period. Treatment may be continued as long as necessary to achieve the desired results. For instance, treatment may continue for about 3 or 4 weeks up to about 12-24 months or longer, including ongoing treatment. The compound can also be administered in several doses intermittently, such as every few days (for example, at least about every two, three, four, five, or ten days) or every few weeks (for example at least about every two, three, four, five, or ten weeks).

b. Desired Response

One or more disclosed modulatory agents and/or additional therapeutic agents are administered by a specific route and/or concentration to generate a desired response. In some examples, a desired response refers to an amount effective for lessening, ameliorating, eliminating, preventing, or inhibiting at least one symptom of a disease, disorder, or condition treated and may be empirically determined. In various embodiments of the present disclosure, a desired response is cell proliferation, such as proliferation of HSC or bone marrow stem cells, red blood cell production. In various embodiments of the present disclose, a desired response is reduced cell proliferation, such as in a subject having polycythemia.

In particular examples, the improvement in cell proliferation compared with a control is at least about 10%, such as at least about 30%, or at least about 50% or more, including an at least 15%, at least 20%, at least 25%, at least 30%, at least 40%, at least 45%, at least 50%, at least 60%, at least 70%, at least 80%, at least 90%, including a 10% to 90% increase, 20% to 80% increase, 30% to 70% increase or a 40% to 60% increase (e.g., a 10%, 20%, 30%, 40%, 50%, 60%, 70%, 80%, 90%, 95%, 100%, 200% or more increase).

In particular examples, cell proliferation is reduced as compared with a control is at least about 10%, such as at least about 30%, or at least about 50% or more, including an at least 15%, at least 20%, at least 25%, at least 30%, at least 40%, at least 45%, at least 50%, at least 60%, at least 70%, at least 80%, at least 90%, including a 10% to 90% decrease, 20% to 80% decrease, 30% to 70% increase or a 40% to 60% decrease (e.g., a 10%, 20%, 30%, 40%, 50%, 60%, 70%, 80%, 90%, 95%, 100%, 200% or more decrease).

EXAMPLES

Example 1

Materials and Methods

This Example describes the Materials and Methods utilized in Examples 2 and 3.

Mice and Rats

For the animal studies, 8-28 week-old, age and gender matched C57BL/6 wildtype mice (WT), AVPR1A KO, AVPR1B KO, AVPR2 heterozygous and OXTR KO mice and littermate controls (on C57BL/6 background) were used. In initial characterizations of the KOs and wild-type controls, older mice were used (up to 52 weeks of age). Brattleboro and Long-Evans (LE) rats (http://www.rrrc.us) were used for tissue harvest to culture BMSCs similarly to mice and bred in house for the in vivo studies.

Human Tissue

Human brain tissue was a gift from the Human Brain Tissue Bank, Semmelweis University (HBTB) and the Semmelweis University Regional Committee of Science and Research Ethic to remove human brain tissue samples, collect, store and use them for research. Human bone marrow sections were obtained as surgical waste from de-identified patients under procedures approved by the Office of Human Subjects Research, NIH.

Cells

Mouse bone marrow stromal cells (mBMSCs) were isolated from C57BL/6 mice and cultured as described before (Nemeth, K. et al. *Nature medicine* 15, 42-49, doi:10.1038/nm.1905 (2009). Human bone marrow stromal cells (hBMSCs) from healthy donors were obtained from the Bone Marrow Stromal Cell Transplantation Center of the NIH and were cultured as described earlier (Nemeth, K. et al. *Stem Cells* 30, 222-231, doi:10.1002/stem.771 (2012)). Human peripheral blood CD34$^+$ cells were isolated from healthy donors after 5 days of G-CSF treatment (10 μg/kg Filgrastim; Amgen, Thousand Oaks, Calif.) and leukopheresis. Cells were sorted using anti-CD34 magnetic beads (Miltenyi Biotech, Auburn, Calif.) and subsequently frozen and stored at −150° C.

RT-PCR

Total RNA was isolated from human CD34$^+$ cells (see above), a human hypothalamus sample (paraventricular nucleus, PVN), mouse bone marrow LSK (lineage negative, Sca-1 positive and c-kit positive) cells, human BMSCs and mouse BMSCs using the Stratagene Absolutely RNA Microprep kit (Stratagene, La Jolla, Calif.). The DNase treatment step was slightly modified. Briefly, on column DNA digestion was performed using Qiagen DNase (RNase free DNase kit, Qiagen, Valencia, Calif.) at room temperature for 30 minutes. Isolated total RNA was reverse transcribed using oligo-dT primers and Moloney-murine leukemia virus reverse transcriptase according to the instructions of the manufacturer (Promega, Madison, Wis.).

The resultant cDNA was amplified with QuantiTect SYBR Green RT-PCR kit (Qiagen) or with SYBR Green Supermix (Bio-Rad, Hercules, Calif.). For qPCR, cDNA (2 μls of cDNA for AVP expression and 1-1 μl for OXT or beta-actin expression) was amplified with QuantiTect SYBR Green RT-PCR kit and the expression data were normalized to human beta-actin expression.

Primers were designed, if practical, to produce PCR products spanning introns. For primer pairs targeting to the same exon, control studies using 1-step RT-PCR without reverse transcriptase were performed.

RT-PCR conditions were as follows: 50° C. for 30 min reverse transcription (only for the 1-step RT-PCR), 95° C. for 15 min initial activation of the Taq polymerase and denaturation of the reverse transcriptase and then 40 cycles of 94° C. for 15 sec denaturation, various primer-specific temperatures (Tables 1 and 2) for 30 sec annealing, and 72° C. for 30 sec extension. PCR products were run on 2% agarose gels and visualized with ethidium bromide.

TABLE 1

Exemplary AVP receptor agonists and antagonists:

| | Target | Mass | Cat# | Company |
|---|---|---|---|---|
| Agonists | | | | |
| dCha4AVP | AVPR1B | 1094.31 | 3126 | Tocris |
| [Arg8]-Vasopressin (AVP) | | 1085.3 | 24289 | AnaSpec |
| [Phe2, Ile3, Orn8] Vasopressin | AVPR1A | 992.2 | 66-0-11 | American Peptide Company |
| d[Leu4, Lys8]-VP | AVPR1B | 1026 | generous gift from Dr M. Manning | University of Toledo |
| (Deamino-Cys1, Val4, D-Arg8)-Vasopressin dVDAVP, (Val4)-Desmopressin | AVPR2 | 1040.24 | H-3176 | Bachem |
| Antagonists | | | | |
| SR 49059 - Relcovaptan | AVPR1A | 620.5 | 2310 | Tocris |
| SSR 149415 - Nelivaptan | AVPR1B | 630.11 | Axon 1114 | Axon Medchem |
| (1-Adamantaneacetyl1, D-Tyr(Et)2, Val4, Abu6, Arg8•9)-Vasopressin | AVPR2 | 1239.53 | H-7705 | Bachem |

TABLE 2

Human primers:

| Target | Primer sequence | PCR product size | Annealing T | Cycles |
|---|---|---|---|---|
| Human AVPR1A NM_000706 | huAVPR1A for 1: CCGCCTGGGTGCTGA GCTTC (SEQ ID NO: 1) huAVPR1A rev 1: TCTTCCCGCGGACGT TGCAC (SEQ ID NO: 2) 1 step RT-PCR | 234 bp | 65° C. | 45 |
| Human AVPR1B NM_000707 | huAVPR1B for 1: GGCTGCCATCTCGGG TCAGC (SEQ ID NO: 3) huAVPR1B rev1: CAGGCAAGGTGACGC AGGGG (SEQ ID NO: 4) | 283 bp | 55° C. | 45 |
| Human AVPR2 NM_000054 | Hu AVPR2 for: ATTCATGCCAGTCTG GTGC (SEQ ID NO: 5) Hu AVPR2 rev: TCACGATGAAGTGTC CTTGG (SEQ ID NO: 6) | 423 bp | 58° C. | 45 |
| Human OXTR NM_000916 | hOTRo32: ATCATCGTGCTGGCC TTCATCGTG (SEQ ID NO: 7) hOTRo33: CCTTATACACAAACA TACGCCATC (SEQ ID NO: 8) | 430 bp | 55° C. | 45 |
| Human AVP NM_000490 | Hu AVP 1 for: CGACCTGGAGCTGAG ACAG (SEQ ID NO: 9) Hu AVP 1 rev: CGGCAGGTAGTTCTC CTCCT (SEQ ID NO: 10) | 145 bp | 55° C. | 40 |
| Human OXT NM_000915 | Hu OXT 2 for: GGAGGAGAACTACCT GCCGT (SEQ ID NO: 11) Hu OXT 2 rev: GCTGGGAGAAGGTGG CTT (SEQ ID NO: 12) | 146 bp | 65° C. | 40 |
| Human CCND1 NM_053056 | SABiosciences PPH00128F | 146 bp | 60° C. | 40 |
| Human MYC NM_002467 | SABiosciences PPH00100B | 87 bp | 60° C. | 40 |
| Human LEF1 NM_016269 | SABiosciences PPH02778C | 72 bp | 60° C. | 40 |

PCR products were run on 2% agarose gels and visualized with ethidium bromide. (For specific PCR conditions, primer sequences and target gene bank accession numbers, see Tables 1 and 2).

Immunocytochemistry

Sorted mouse bone marrow cells in droplets of 20 μl PBS were put onto positively charged slides (AmLabs, Bradenton, Fla.) and allowed to sediment for 30 min at 4° C. 20 μl of 4% PFA/PBS was added and the cells were fixed to the slides for 10 min at room temperature and dried. Subsequently, the slides were washed in 0.1M Tris (to remove salts from the PBS) and air-dried.

Human and mouse BMSCs were put into chamber slides in αMEM with 20% FBS and allowed to attach overnight. The cells in the chamber slides were fixed using 4% PFA/PBS for 10 min at room temperature. Fixed cells were stored in PBS at 4° C. Cells on slides or in chamber slides were washed with PBS, blocked using Power Block Universal Blocking Reagent (Biogenex, San Ramon, Calif.), and incubated with the primary antibody overnight.

TABLE 3

Mouse primers:

| Target | Primer sequence | PCR product size | Annealing temp | Cycles |
| --- | --- | --- | --- | --- |
| Mouse AVPR1A NM_016847 | ms AVPR1A F: CAGATGTGGTCAGTC TGGGATA (SEQ ID NO: 13) mAVPR1A R: CTCATGCTATCCGAG TCATCCT (SEQ ID NO: 14) | 215 bp | 60° C. | 45 |
| Mouse AVPR1B NM_011924 | ms AVPR1B #13: GCTGGCCCAAGTCCT CATCTTCTG (SEQ ID NO: 15) AVPR1B #12: GCGGTGACTCAGGGA ACGT (SEQ ID NO: 16) | 323 bp | 60° C. | 45 |
| Mouse AVPR2 NM_019404 | ms V2 for 1: CACGTCTGCAGTGCC TGGGG (SEQ ID NO: 17) ms AVPR2ev 1: CATGGAAGCGGTCGG TGGCA (SEQ ID NO: 18) | 302 bp | 62° C. | 45 |
| Mouse OXTR NM_001081147 | ms OXTR F: CCTTTCTTCTTCGTG CAGATGT (SEQ ID NO: 19) ms OXTR R: GGAGGAGTTGCTTTT CTTGCTA (SEQ ID NO: 20) | 240 bp | 60° C. | 45 |
| Mouse AVP NM_009732 | ms AVP for: GGCATCTGCTGCAGC GACGAGA (SEQ ID NO: 21) ms AVP rev: TAGACCCGGGGCTTG GCAGAA (SEQ ID NO: 22) 1 step RT-PCR | 188 bp | 65° C. | 40 |
| Mouse OXT NM_011025 | Qiagen SYBR Green Quantitect assay: QT00252203, 1 step RT-PCR | 184 bp | 55° C. | 40 |
| Mouse AVPR2* NM_019404 | ms AVPR2 F: CAAGGGACACCC TGGTTCTA (SEQ ID NO: 23) R: CTACGCAACTCC GAGGAGAC (SEQ ID NO: 24) | 145 bp | 60° C. | 45 |
| Mouse AVPR1A* NM_016847 | ms AVPR1A F: TAGGCCTGGTTC GTAAGCAT (SEQ ID NO: 25) R: TTCAATCACGGA CCAGTTCA (SEQ ID NO: 26) | 148 bp | 60° C. | 45 |
| Mouse EPOR* NM_010149.3 | ms EPOR F: GTCTGACTTGGC CTCAAAGC (SEQ ID NO: 27) R: GTGAGGTGGAGT GGGAGGTA (SEQ ID NO: 28) | 133 bp | 60° C. | 45 |
| Mouse AVPR1B* NM_011924 | ms AVPR1B: F: ATCCGAACCGTG AAGATGAC (SEQ ID NO: 29) R: TCATTAGGGGCA TTCTCGTC (SEQ ID NO: 30) | 110 bp | 60° C. | 45 |

*Designed for Q-PCR

After blocking endogenous peroxidase with Peroxidase Block (DAKO, Carpinteria, Calif.), secondary antibodies and tyramide-fluorophores were used to detect the target protein. Cell nuclei were stained with DAPI. (See Tables 4 and 5 for primary and secondary antibodies and reagents used for immunostaining.)

Paraffin-embedded human toe sections were deparaffinized, microwave treated and incubated with the first primary antibody that was visualized using a fluorochrome tyramide. Following a microwave treatment to eliminate any possibility of a non-specific binding to previous reagents another microwave treatment was used (Toth, Z. E. & Mezey, E. *The Journal of histochemistry and cytochemistry: official journal of the Histochemistry Society* 55, 545-554, doi:10.1369/jhc.6A7134.2007 (2007)) and the second staining initiated. The sections were analyzed using a Leica DMI600 inverted fluorescent microscope and Volocity software to perform Z series and iterative restoration.

Immunohistochemical controls included using no primary antibody; testing transfected versus untransfected cells against the target peptide or using knockout animal cells as negative controls when it was available. Furthermore, for additional confirmation for the AVPR1B and AVP itself several different antibodies were used raised against different portions of the peptide/protein.

AVP and OXT Release (AVP RIA and OXT ELISA)

Five million mouse or 2 million human BMSCs were plated in T75 flasks in αMEM medium with 20% FBS and allowed to attach overnight. The medium was replaced the next day with 3 ml of αMEM with 2% FBS. Supernatants of the cultures were collected and centrifuged (1600 rpm, 5 min, 4° C.) to remove possible cell debris and then frozen and stored at −20° C. Samples were extracted on solid phase columns (Alpco Diagnostics, Salem, N.H.) and evaporated to dryness under vacuum. The remaining pellets were reconstituted with phosphate buffer. AVP radioimmunoassay was performed according to the protocol of the manufacturer (Vasopressin Ultrasensitive RIA kit, Alpco Diagnostics). For the measurement of OXT, cells were cultured, stimulated and supernatants were prepared as described above. The amount of OXT was determined using a competitive OXT immunoassay kit (Assay Designs, Ann Arbor, Mich.).

Intracellular $Ca^{2+}$ Measurements and cAMP Assay

Human BMSCs were loaded with Fura-2 and the cells were stimulated with AVP, or OXT. Intracellular $Ca^{2+}$ concentration was assayed as described before (Ely, J. A. et al. *J Biol Chem* 266, 18635-18641 (1991). To study their response to AVP and specific AVP receptor agonists and antagonists human CD34+ hematopoietic progenitors were Fura-2 loaded and Cytoplasmic Ca2+ measurements were performed in cells kept in suspension using a fluorescence spectrophotometer (Deltascan, Photon Technology International). Ratiometric measurements were recorded at 340/380 nm excitation and 500 nm emission and the ratios were plotted against time. Ionomycin (10 μM) was added at the end of each run to determine the maximum fluorescence ratio.

cAMP Measurements

For cAMP quantitation, $8 \times 10^5$ per well human BMSCs were plated in 6 well plates and left to attach overnight. Next day, the medium was changed and the cells were stimulated with AVP or deamino-$Cys^1$, D-$Arg^8$ AVP (DDAVP, a V2 receptor agonist) at $10^{-6}$ M for 4 minutes. Cells were washed with PBS and lysed with R&D cell lysis buffer. Cyclic AMP was measured with the R&D cAMP Parameter assay kit (R&D Systems, Minneapolis, Minn.) according to manufacturer's instructions. Total protein concentrations of the cell lysates were measured using the Micro BCA Protein Assay kit (Pierce, Rockford, Ill.) and cAMP amount was normalized to 100 μg of total protein.

For cAMP measurements in $CD34^+$ human hematopoietic progenitor cells derived from two donors. The cAMP femto 2 kit (Cat#62AM5PEB, Cisbio) was used according to manufacturers instructions. The measurements were done on a Wallac Victor2 1420 multilabel counter (Perkin Elmer).

BrdU Cell Proliferation Assay

Sorted mouse bone marrow LSK cells (10000 cells/well) were plated in a 96 well plate in Stemspan serum free expansion medium (STEMCELL Technologies, Vancouver, Canada) with Pen/Strep, and the following hematopoietic factors: 100 ng/ml TPO, 50 ng/ml FLT3L, 50 ng/ml IL-3 and SCF 100 ng/ml (Peprotech, Rocky Hill, N.J.). Cells were treated with $10^{-8}M$-$10^{-14}M$ or OXT (Sigma-Aldrich, St. Louis, Mo.). When using human $CD34^+$ cells (5000 cells/well), human SCF, TPO, FLT3L and G-CSF (Peprotech, each at 50-100 ng/ml) were added to the Stemspan medium. Cells were treated with $10^{-8}M$-$10^{-14}M$ AVP. After 24 hours, BrdU at a 1:1000 concentration was added to the cultures and incorporation of BrdU was measured using the Cell Proliferation ELISA BrdU kit (Roche, Mannheim, Germany) after another 24 hours of incubation.

EdU Proliferation Assay

In vivo AVP-treated/hemorrhaged/control mice were IP injected with 10 μM/1000 g BW 5-ethynyl-2'-deoxyuridine (EdU: Life Technologies) for 2 hours. Single cell suspensions from the tibial and femoral bone marrows of mice (n=5 in each group) were prepared. After lysing the cells with ACK buffer, cells of the erythroid lineage were labeled with antibodies against TER-119 (BD Pharmingen) and CD71 (BD Pharmingen) or CD44 (BD Pharmingen) conjugated with FITC or PE fluorophores. After washing with FACS buffer, cells were fixed/permeabilized according to the manufacturer's recommendation (Life Technologies). Incorporated EdU molecules were visualized by a click reaction with Alexa Fluor 647-conjugated picolyl-azide and cell nuclei were stained with DAPI. Cell cycle characteristics of erythroid cells were detected with a Beckman-Coulter MoFlo Astrios flow cytometer.

CFU Assay $CD34^+$ cells from healthy donors were plated into semi-solid methylcellulose medium (Methocult) containing hematopoietic factors (GM-CSF 5 ng/ml, IL-3 5 ng/ml, SCF 50 ng/ml, EPO 2.5 U/ml). AVP, OXT or a specific human AVPR1B receptor agonist ($dCha^4AVP$) were added to the medium at $10^{-8}$ M or $10^{-6}$ M alone or in combination with 200 ng/ml dickkopf related protein 1 (Dkk1, Wnt pathway inhibitor) or $10^{-8}$ M 1L-6-hydroxymethyl-chiro-inositol 2-(R)-2-O-methyl-3-O-octadecylcarbonate (HIMO; an Akt inhibitor).

The number of erythroid colony forming units (E-CFU) and granulocyte-macrophage colony forming units (GM-CFU) were determined based on morphological criteria on $7^{th}$ and $14^{th}$ days in culture.

Flow Cytometry

Single cell suspensions from the tibial and femoral bone marrow of C57BL/6 mice and AVPR1B KO, AVPR2+/− were made. After lysing the red blood cells with ACK buffer, Fc receptors were blocked with mouse IgG. Cells were stained with biotinylated lineage antibodies (BD mouse lineage panel kit: anti mouse Gr-1, B220, CD11b, TER119, CD3e), c-kit APC and Sca-1 FITC antibodies. After 3 times wash in FACS buffer (1×PBS/5% FBS), streptavidin PE was used as a fluorophore. Cells were fixed in 2% PFA/PBS and analyzed with an BD LSRII or a BD FACS Calibur flow cytometer (for details on the antibodies used see Table 5).

TABLE 5

Antibodies used for flow cytometry studies.

| Antibodies | Clones | Fluorochromes | Source |
| --- | --- | --- | --- |
| anti-mouse | | | |
| CD45.1 | A20 | eFluor450 | Ebiosciences |
| CD45.2 | 104 | AlexaFluor700 | Ebiosciences |
| Gr-1 (Ly-6G) | RB6-8C5 | APC-eFluor 780 | Ebiosciences |
| B220 (CD45R) | RA3-6B2 | PE-Cy7 | Ebiosciences |
| Ter-119 | TER-119 | APC | Ebiosciences/BD Biosciences |
| CD3e | 145-2C11 | PE | Ebiosciences |
| CD11b (Mac-1) | M1/70 | PerCp-eFluor710 | Ebiosciences |
| CD71 | C2 | PE | BD Biosciences |
| CD41 | MWReg30 | FITC | BD Biosciences |
| CD61 | | PE | BD Biosciences |
| sca1 (Ly-6A/E) | D7 | FITC or PE-Cy7 | BD Biosciences/ Ebiosciences |
| c-kit (CD117) | 2B8 | APC | BD Biosciences |
| CD34 | RAM34 | AlexaFluor700 | Ebiosciences |
| CD150 | mShad150 | PE | Ebiosciences |
| CD48 | HM48-1 | PerCp Cy5.5 | Ebiosciences |
| CD16/32 | 93 | PerCpCy5.5 | Biolegend |
| Flt3 (CD135) | A2F10 | PE | Ebiosciences |
| IL-7R (CD127) | A7R34 | PerCpCy5.5 | Ebiosciences |
| anti-human | | | |
| CD34 | | PE | BD Biosciences |
| CD38 | | FITC | BD Biosciences |
| Other antibodies | | | |
| Streptavidin | | APC Cy7 | Biolegend |
| Streptavidin | | PE | BD Biosciences |
| Vybrant DyeCycle Violet Stain | | | Invitrogen |
| biotin mouse lineage panel | | | BD Biosciences |
| mouse hematopoietic lineage biotin panel | | | Ebiosciences |

TABLE 5-continued

Antibodies used for flow cytometry studies.

| Antibodies | Clones | Fluorochromes | Source |
|---|---|---|---|
| DAPI | D1306 | | Molecular Probes |
| Anti Rat IgG1 | MRG1-58 | | BioLegend |
| Mix-n-Stain CF Dye Kit | | CF532 | Biotium |
| Anti Rat IgG2b | | FITC | Southern Biotech |

For lineage negative, Sca-1 positive and c-kit positive (LSK) cell sorting, rat anti-mouse lineage antibodies (anti CD4, CD8, B220, Ter119, Gr-1, CD11b) were added to bone marrow cell suspension after ACK lysis and cells were depleted using anti-rat magnetic beads (Biomag anti rat IgG, Qiagen). Lineage negative cells were stained with c-kit PE/Cy5 and Sca-1-FITC antibodies and the double positive population was further enriched with anti-PE and anti-FITC magnetic beads (Miltenyi). LSK cells were sorted on a DAKO Cytomation MoFlo cell sorter. For LSK subpopulation sorting lineage depleted cells were stained for c-kit, Sca-1, CD48, CD150 and CD34 and 4 LSK subpopulations were sorted using the gating strategy described by Wilson et al. (34).

Sorted cells from HSC (LSK, $CD34^-$, $CD48^-$, $CD150^+$), MPP1 (LSK, $CD34^+$, $CD48^-$, $CD150^+$), MPP2 (LSK, $CD34^+$, $CD48^+$, $CD150^+$) and MPP3/4 (LSK, $CD34^+$, $CD48^+$, $CD150^-$) subpopulations were plated in 1×PBS onto coated glass slides fixed with 2% PFA and immunostained for AVPR1B. Erythropoietic progenitors were sorted based on CD71 and Ter119 markers. All cells were sorted using a MoFlo Astrios cell sorter (Beckman Coulter).

Competitive Repopulation Assay

Based on the published protocol by Miller et al. (*Curr Protoc Immunol* Chapter 22, Unit 22B 22, doi:10.1002/0471142735.im22b02s80 (2008)) female, 6-8 weeks old B6SJL-Ptprc Pepc/BoyJ (CD45.1) mice were irradiated (2×450G, 6 hours difference between irradiations) and transplanted next day with 2 million Z/EG (lacZ/EGFP) bone marrow cells (competitor GFP expressing CD45.2 cells) and with 2 million WT or AVPR1b KO bone marrow cells (CD45.2 cells). Transplanted mice were kept in sterile caging for 4 weeks after transplant and trimethoprim-sulfamethoxazole were added to their drinking water. After 1,2,3,4 months peripheral blood were obtained from the retro-orbital plexus of the mice and ACK lysed blood cells were stained for CD45.1, CD45.2, Gr-1, CD11b, CD3, B220 markers and analyzed with LSRII flow cytometer. Bone marrow and spleen cells were isolated 4 months after transplant and analyzed the same way.

LSK Subpopulation Sorting

Bone marrow from femurs and tibiae of 20 C57BL6 mice were isolated and pooled. ACK lysed bone marrow cells were incubated with rat lineage antibodies and depleted with anti-rat magnetic secondaries. Lineage depleted cells were stained for c-kit, Sca-1, CD48, CD150 and CD34 and 4 LSK subpopulations were sorted using the gating strategy described by Wilson et al. (*Cell* 135, 1118-1129, doi: 10.1016/j.cell.2008.10.048 (2008)). Sorted cells from HSC (LSK, $CD34^-$, $CD48^-$, $CD150^+$), MPP1 (LSK, $CD34^+$, $CD48^-$, $CD150^+$), MPP2 (LSK, $CD34^+$, $CD48^+$, $CD150^+$) and MPP3/4 (LSK, $CD34^+$, $CD48^+$, $CD150^-$) subpopulations were plated in 1×PBS onto coated glass slides fixed with 2% PFA and immunostained for AVPR1b or OXTR. To identify proliferating and apoptotic cells based on DNA content in some of studies, Vybrant Dye-cycle Violet live cell staining and propidium iodide were combined with the above markers.

In Vivo AVP Injections

Short-term effect of a single intraperitoneal AVP injection: [Arg8]-Vasopressin (Ana-spec) (100 μg/kg body weight) together with 20 mg/kg body weight o-phenantroline (Sigma-Aldrich) or vehicle PBS with 20 mg/kg body weight o-phenantroline. 16 hours later bone marrow (two hind limbs) and spleen cells were obtained to study the distribution of HSCs and multipotent progenitors (MPP) as well as intermediate lineage-com-mitted progenitors and the erythroid populations as described before (n=5/group) (Wilson et al. *Cell* 135, 1118-1129, doi:10.1016/j.cell.2008.10.048 (2008); Pronk, C. J. et al. *Cell Stem Cell* 1, 428-442, doi:10.1016/j.stem.2007.07.005 (2007); Weissman, I. L. *Cell* 100, 157-168 (2000). Serial AVP injections: Mice (n=8-9) were injected ip. 2 times/day with AVP 100 μg/kg body weight or PBS for 6.5 days. After day 6.5, mice were euthanized and the erythroid populations ($CD71^+$, $Ter119^+$) in spleen and bone marrow were analyzed (Cheshier, S. H. et al., *Stem Cells Dev* 16, 707-717, doi:10.1089/scd.2007.0017 (2007).

Experimental Hemorrhage (Short and Long Term)

Twenty five percent of their calculated circulating blood volume (calculated based on Animal Research Advisory Committee Guidelines for survival bleeding of mice and rats, OACU, NIH) was drained from the retro-orbital plexus of wild type and AVPR1B KO mice.

For the short-term studies, 24 hours after bleeding bone marrow and spleen were harvested (n=5/group). Hematopoietic stem cells (HSCs), multipotent progenitors and intermediate lineage-committed progenitors were analyzed as described before (for details about antibodies see Table 4). Megakaryocytes were studied using CD41, CD61 markers.

TABLE 4

Reagents used for immunostaining.

| | Cat no | Source | Dilution |
|---|---|---|---|
| Receptor antibodies | | | |
| Rabbit Anti AVPR1A (H70) | Sc-30025 | Santa Cruz | 1/500 |
| Rabbit Anti AVPR1B | | S. J. Lolait[16] | 1/500 |
| Rabbit Anti AVPR2 | LS-A272 | MBL International | 1/500 |
| Rabbit Anti OXTR | LS-A244 | MBL International | 1/500 |
| AVP and OXT antibodies | | | |
| Rabbit VA4 AVP peptide | | H. Gainer (NIH)[15] | 1/500 |
| Rabbit VA10 OXT peptide | | H. Gainer (NIH)[15] | 1/500 |
| Mouse mAb PS38 (Neurophysin I) | | H. Gainer (NIH)[17, 20] | 1/500 |
| Mouse mAb PS41 (Neurophysin II) | | H. Gainer (NIH)[17, 20] | 1/500 |
| Rabbit Anti Alk. Phosphatase | HPA007105 | Sigma | 1/500 |
| Secondary antibodies and other reagents | | | |
| Anti rabbit polymer HRP | 87-9263 | Invitrogen/ Zymed Labs | 1/1 |
| Anti mouse polymer HRP | 87-9163 | Invitrogen/ Zymed Labs | 1/1 |
| FITC tyramide | | homemade | 1/20000 |
| Alexa 594 tyramide | | homemade | 1/2000 |
| FITC Plus tyramide | NEL741001KT | Perkin Elmer | 1/750 |

TABLE 4-continued

Reagents used for immunostaining.

| | Cat no | Source | Dilution |
|---|---|---|---|
| Cy3 Plus tyramide | NEL744001KT | Perkin Elmer | 1/1000 |
| DAPI (5 mg/ml stock in dimethylformamide) | D1306 | Molecular Probes | 1/25000 |

For the long-term hemorrhage studies, 2, 5, 9, and 16 days later 50 μls of peripheral blood was obtained from the tail vein of wild type and AVPR1B KO mice that underwent hemorrhage and from the non-bled wild type controls (n=8-10/group).

The reticulocyte ratio of peripheral blood was determined using the Retic-Count flow kit (BD Biosciences) according to the manufacturer's instructions. Hematocrit values were measured with an automated analyzer. The reticulocyte index was calculated as follows: reticulocyte ratio %/total gated cells×hematocrit/45.

Spleen and Bone Marrow Histology

C57BL/6 wild type and AVPR1A, AVPR1B, OXTR KO mice were perfused intracardially with 4% PFA/PBS. Long bones (femur, tibia) and spleens were fixed in 4% PFA/PBS for 2 days and then transferred to 70% ethanol. The bones were decalcified with 0.25M EDTA/PBS for 2 weeks. The decalcification process was checked with a Faxitron X-ray imager. Decalcified bones and the spleens were embedded into paraffin. Tissue sections were cut, put onto slides, deparaffinized and stained with hematoxylin-eosin for histological evaluation.

In Vivo Anemia Models to Study the Regeneration of Peripheral Blood Cells

Three models of anemia were used.

1. Hemorrhage

Mice were anesthetized with isoflurane. Twenty five percent of their calculated circulating blood volume (calculated based on Animal Research Advisory Committee Guidelines for survival bleeding of mice and rats, OACU, NIH) was drained from the retro-orbital plexus.

24 hours after bleeding bone marrow and spleen were harvested (n=5/group). Hematopoietic stem cells (HSCs), multipotent progenitors and intermediate lineage-committed progenitors were analyzed (for details about antibodies see Table 5). Megakaryocytes were studied using CD41, CD61 markers.

The reticulocyte ratio of peripheral blood was determined using the Retic-Count flow kit (BD Biosciences) according to the manufacturer's instructions. Hematocrit values were measured with an automated analyzer and microhematocrit tubes. The reticulocyte index was calculated as follows: reticulocyte ratio %/total gated cells×hematocrit/45.

To infuse vasopressin into the mice, AVP filled ALZET pumps were implanted subcutaneously on the dorsal aspect of the neck (5 ug/day, Alzet 1007D—7 days, 2002-14 days). Vasopressin was also given immediately and 6 hours later as a bolus injection (100 μg/kg). Alzet pumps were inserted subcutaneously. The dimensions and pump specification are: ALZET, (DURECT Corporation, Cupertino, Calif., USA) mini-osmotic pump models 1007D or 2002. The pumps deliver 0.5 μl/h of the desired substance for a for 2-week period. In some cases, erythropoietin antibody (100 μg/mice) was given before anesthesia with the corresponding control antibody. This antibody proved to be neutralizing EPO's effect in hemorrhage based on previous pilot experiments and the amount of EPO given was set up accordingly. Following the initial hemorrhage blood samples were taken at 2, 4 and in some cases 6 days later to determine hematocrit and corrected reticulocyte values.

2. Phenylhydrazine

Phenylhydrazine, a known hemolytic agent, was injected intraperitoneally by administration of phenylhydrazine hydrochloride ip. 50 mg/kg body wt. (injection volume range of 100-150 μls) on day 0 and 1 and then mice were implanted with ALZET micro-osmotic pumps as described above to deliver AVP or vehicle. Blood samples were taken at 2, 4 and in some cases 6 and 14 days later to determine hematocrit and corrected reticulocyte values.

3. Sublethal Irradiation to Suppress the Bone Marrow

Mice were irradiated with 4.5 Grays, and 24 hours later mice were implanted with ALZET micro-osmotic pumps as described above to deliver AVP or vehicle. Mice were treated with Trimethoprim and Sulfamethoxazole (Bactrim, Septra) for 7 days before irradiation and continued the treatment for 4 weeks after irradiation. Using a pediatric formulation, the stock concentration contains 40 mg/5 ml Trimethoprim and 200 mg/5 ml Sulfa, so that the treated drinking water will deliver 0.13 mg/ml trimethoprim and 0.67 mg/ml sulfa to the mice.

Generating Mice with AVPR1B KO Bone Marrow

Since enough homozygous age and gender matched AVPR1B KO mice with appropriate controls could not be bred to do a variety in vivo studies we decided to use bone marrow transplantation on age (8-10 weeks) and gender (male) matched C57B/6 mice. Pooled BM from homozygous AVPR1B mice was used and as a control pooled BM of their WT littermates were used. After the mice recovered from the transplants, we used hemorrhage and phenylhydrazine (see above) to test if the AVPR1B KO BM has the same capacity to recover following anemia then the WT mice.

Studies in Brattleboro Rats that Genetically Lack Vasopressin

Homozygous Brattleboro (BB) rats (2 months old) and their WT controls, the Long Evans (LE) rats were exposed to sublethal irradiation and blood samples were taken from the orbital plexus at 2, 4, 6, 12 and 19 days to compare the recovery of peripheral blood counts.

Studies on BMSCs Freshly Isolated Following Acute Hemorrhage

C57BL/6 male mice were bled as described above or used as controls (n=2-3 in each group). 30 minutes after experimental hemorrhage under anesthesia (twenty five percent of their calculated circulating blood volume was drained from the retro-orbital plexus) animals were euthanized and limbs dissected. Marrows were flushed out and the bones were digested with collagenase type 1 (Worthington cat# S5P8401), crushed, and processed for depletion. Using QIAGEN Bio-Mag anti-rat beads, and appropriate antibodies (See Table 3) lineage positive cells were depleted using magnetic beads (Biomag anti rat IgG, QIAGEN). All cells were stained for CD45, Ter-119 and CD31. (In some cases for Sca-1 and PDGFRα, too as additional controls to make sure that we in fact isolated BMSCs). Using a BC MoFlo Astrios sorter triple negative (CD45-, Ter119-, CD31-) cells were then sorted and the RNA was extracted immediately using Trizol LS (INVITROGEN #10296028), and Quick-RNA Miniprep kit (Zymo Research #R1055) according to manufacturer's instructions, followed by cDNA synthesis (INVITROGEN Super-ScriptIII #11752). The resultant cDNA was then amplified with QuantiTect SYBR Green RT-PCR kit (QIAGEN) using AVP specific primers and the mRNA was compared between BMSCs derived from control versus hemorrhaged mice. The resulting PCR products were sequenced to make sure that the amplicon is indeed AVP.

Finally, the sorted cells were also checked to show that they are able to form colonies and—if using the specific media—they can form bone and adipose tissue.

Sequencing of Direct PCR Products

PCR products were cleaned over Sephadex G-50 Superfine columns (provided by GE Healthcare, lot number 10089708).

Brattleboro/LE Rat BMSC and Human Hematopoietic Progenitor Co-Cultures

Rat BMSCs were isolated and cultured from the bone marrow of 5-6 weeks old male Brattleboro (animals that lack the ability to produce vasopressin) and Long-Evans rats (control strain for the Brattleboro rats) as described before. For flow cytometry studies, 100000 rat BMSCs per well were plated in αMEM medium (20% FBS) in 12 well plates in quadruplicates and incubated overnight. Next day, medium was removed and 200000 human CD34 cells per well were added in Stemspan medium with factors (human SCF, TPO, FLT3L and G-CSF 100 ng/ml). Co-culture was stimulated with AVP or left unstimulated (PBS) and next day BrdU was added. After 24 hours the cells were trypsinized, brought up in αMEM (20% FBS), resuspended and strained through 70 μm cell strainer. For normalization, Sigma beads were added to each sample tube. Cells were washed with FACS buffer and stained for human CD34 and CD38. The subsequent steps were done according to the BD BrdU Flow kit protocol. At flow cytometry measurements, cell numbers were normalized to Sigma bead numbers.

For transwell studies, 10000 human CD34 cells per well were plated in Corning HTS 96 well transwell system (4 μm pore size) into the lower wells in quadruplicates in Stemspan medium with factors (see above), and 5000 rat BMSCs per well were added into upper wells. Co-culture was stimulated with AVP by introducing it into the upper wells. Next day BrdU was added into lower wells and after 24 hours, upper wells with rat BMSCs were removed, the plates were centrifuged, Stemspan medium removed and CD34 cells were air dried to the bottom of the plates. All subsequent steps were done according to Roche BrdU Cell proliferation kit protocol.

Comparison of Peripheral Blood Values Following EPO Vs. AVP Injections in Hemorrhage AVP (100 μg/kg bodyweight) or EPOetin alfa (50 U/bodyweight, EPOgen) was administered intra-peritoneally to mice, immediately following hemorrhage. The amount of EPOetin alfa was based on studies in order to provide comparable data with the AVP treated groups. Hematocrit and reticulocyte counts were measured at different time points.

EPO Neutralization Studies

In some cases Erythropoietin antibody (100 μg/mice) was given before anesthesia with the corresponding control antibody. This antibody proved to be neutralizing EPO's effect in hemorrhage based on previous pilot experiments and the amount of EPO given was set up accordingly.

Statistical Analyses

The biostatistical analysis of the in vivo experiments were performed by Social and Scientific Systems, Inc. Student's t-test or analysis of variance was used with appropriate corrections. Data were evaluated with Graphpad Prism 5.0 software and P value of <0.05 was accepted as statistically significant. Data are given as mean±SD.

Example 2

Stimulation of Hematopoiesis in the Bone Marrow Niche by Systemic and Stromal Vasopressin This example demonstrates stimulation of hematopoiesis in the bone marrow niche by systemic and stromal vasopressin and indicates that a peripherally active AVPR1B agonist can be used to induce erythropoiesis in patients suffering from anemia.

Hemorrhage results in the loss of body fluid, proteins, electrolytes, and blood cells. Following hemorrhage in humans, the hypothalamic hormone AVP is released into the systemic circulation. AVP, also known as the antidiuretic hormone, stimulates water reabsorption by the kidneys to help restore water balance. The finding that hematopoietic stem and progenitor cells (HSPCs) have receptors for AVP indicate that this peptide might stimulate hematopoiesis and help replenish not just the volume but also lost blood cells. To test this hypothesis, anemia was induced by removing blood from animals and found that AVP administration significantly increased red blood cell (RBC) production in wild-type (WT) mice. In two additional models of anemia—one based on lysing circulating RBCs and the other based on killing bone marrow cells by irradiation—AVP administration also accelerated the restoration of RBC numbers in the blood. Following sublethal irradiation, it was observed that Long-Evans rats increased RBC numbers considerably more quickly than AVP-deficient Brattleboro rats did, indicating a physiological role for endogenous AVP in hematopoiesis. Using in vitro studies with mice and human HSPCs and genetically modified mice it was found that it is the AVPR1B receptor that is responsible for these effects, it was also established that in addition to circulating AVP there is a local source of the hormone in the bone marrow. Marrow stromal cells (MSCs) make AVP and release it onto receptors on the HSPCs that they cradle. Based on these discoveries (as described herein) and the finding that human $CD34^+$ cells proliferate in response to AVP and a specific AVPR1B agonist, the inventors discovered that a peripherally active AVPR1B agonist can be used to induce erythropoiesis in patients suffering from anemia.

Arginine-vasopressin (AVP) and oxytocin (OXT) are nine amino acid long peptides that differ from one another in two positions. The structurally related genes encoding AVP and OXT are oriented tail-to-tail on the same chromosome. Most of the AVP and OXT found in blood are made by magnocellular neurons in the hypothalamic supraoptic (SON) and paraventricular (PVN) nuclei. The peptides are synthesized as parts of precursor preprohormones that are cleaved as they are transported in axons that terminate in the posterior pituitary. These precursors yield their respective nonapeptides (OXT or AVP), a carrier protein, neurophysin (OXT-neurophysin or AVP-neurophysin), and, in the case of AVP, an N-terminal glycopeptide known as copeptin. Once it is released from nerve endings in the posterior pituitary into the bloodstream, AVP regulates salt and water homeostasis and OXT regulates parturition and lactation. AVP and OXT also act within the CNS as neurotransmitters to drive a variety of social and affinitive behaviors.

Vasopressin Receptors (AVPR1A, AVPR1B, AVPR2) and the Oxytocin Receptor (OXTR) are Expressed by Hematopoietic Stem and Progenitor Cells in Mice and Humans. AVP and a Specific AVPR1B Agonist Elicit a Calcium Response in Human HSPCs.

Figures 1B, 1C, 1D:
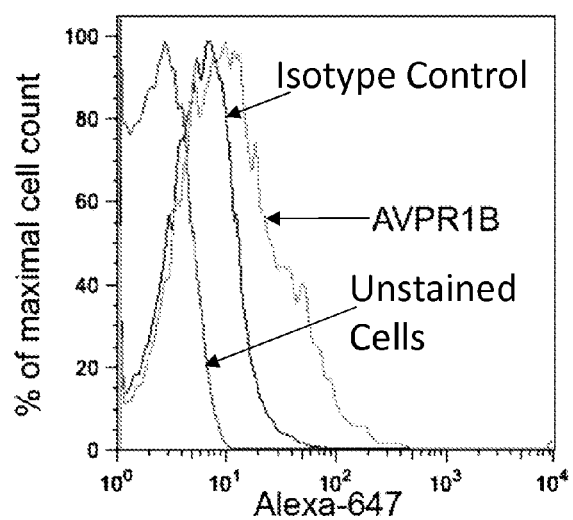
Figure 1E:
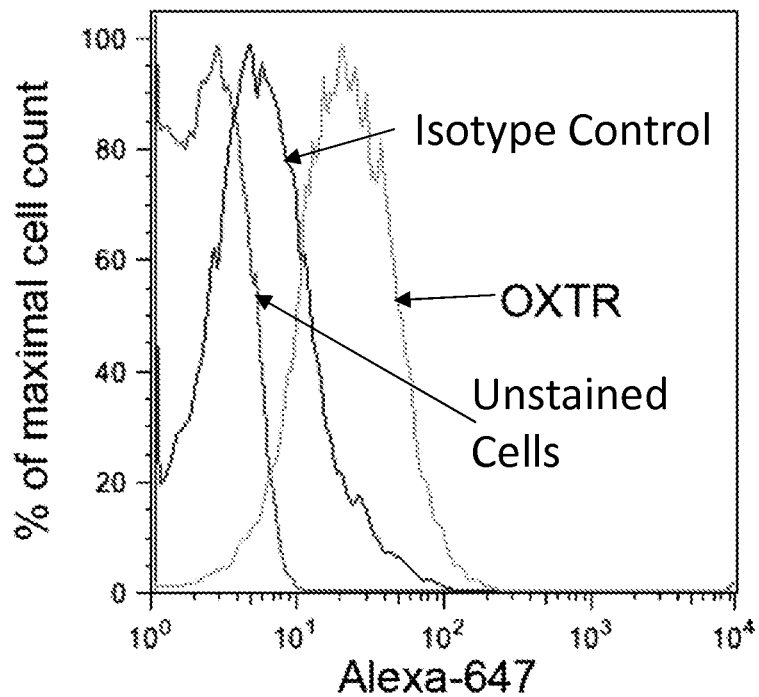
Figure 1F:
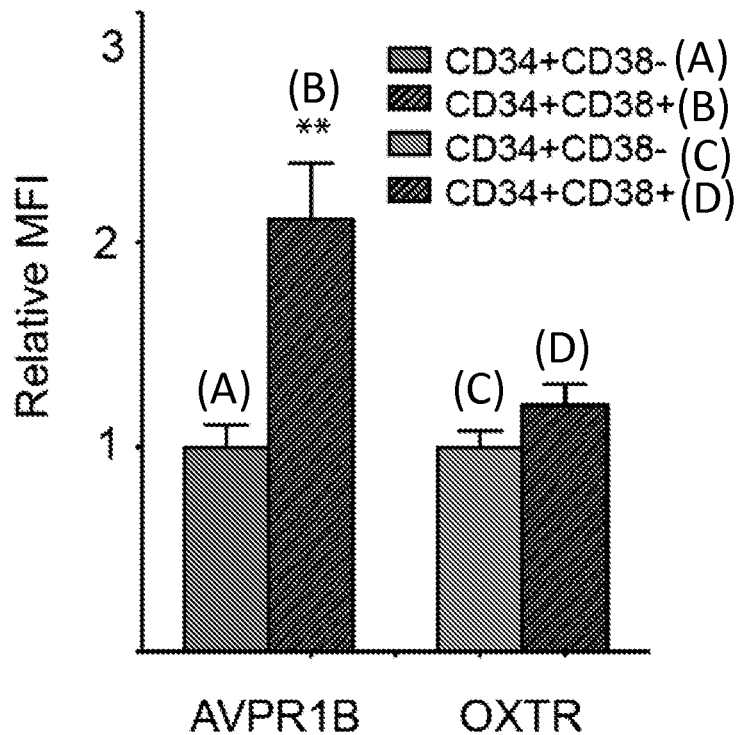

Using RT-PCR, AVPR1A, AVPR1B, AVPR2, and OXTR transcripts were detected in mouse LSK cells and human ($CD34^+$) cell mRNA; no PCR products were found in control reactions (no template or no RT). Immunocytochemistry revealed all of these receptors in the plasma membrane of mouse hematopoietic stem and progenitor cell populations (HSC, MPP1, MPP2 and MPP3/4) (FIG. 1A, 1B) as well. Omitting the primary antibodies eliminated the staining. Similarly, it was found by means of flow cytometry that the AVPR1B and OXTR were present in human CD34+, and CD34+CD38+ double positive cells. (Antibodies directed at the AVPR1A and AVPR2 receptors were not available for such studies.) The CD34+CD38+ progenitor population had significantly more intense staining with AVPR1B receptor antibody than the CD34+CD38− population did. OXTR expression seemed similar in both cell populations (FIG. 1D-1F). These data indicate that mRNAs encoding the AVPR1A, AVPR1B, AVPR2 and OXTR receptors and the receptor proteins are made by mouse and human hematopoietic progenitor cells.

CD34+ cells isolated from human volunteers were used to determine whether these receptors were functional in the human HSPCs. When these cells were treated with either AVP or an AVPR1B agonist there were increases in their intracellular calcium levels, but they did not respond to an AVPR1A agonist. The AVP-induced increase in calcium could be blocked with a specific AVPR1B antagonist, but not an AVPR1A antagonist (see Table 1). Human cells from two different donors were tested with identical results.

Changes in Hematopoiesis in AVPR1B Receptor Knockout Mice

AVPR1A, AVPR1B, AVPR2, and OXTR receptor knockout mice were evaluated. The AVPR1B animals all displayed "extra-medullary hematopoiesis". Wild type and AVPR1B KO mice had similar complete blood cell counts and bone marrow histology, but more megakaryocytes were observed in the AVPR1B KO spleen sections than in sections from wild type animals (FIG. 2A). To quantitate this finding, dissociated spleen cells were stained using antibodies for megakaryocyte markers CD41 and CD61 and analyzed the cells by flow cytometry. The number of CD41+CD61+ spleen cells was indeed significantly higher in the AVPR1B KO animals than in their wild type littermates (FIG. 2A). This data indicates that AVPR1B KO mice have a compensatory increase in hematopoiesis in their spleens. This was not observed in the other AVP and OXT receptor-deficient mice examined. This is consistent with the fact that many papers have been published about X-linked nephrogenic diabetes insipidus, a problem that results from mutations in the AVPR2 gene, but no one has commented on any defect in hematopoiesis in people with this trait or in mouse models of the disorder. Similarly, no abnormalities in hematopoiesis have been described in AVPR1A KO mice. Based on the observations summarized above, it was decided to mainly focus on the role of the vasopressin AVPR1B receptor in regulating hematopoiesis. It is possible, however, that the other AVP receptors might also affect this process, and as noted in the following section, OXT may drive myelopoiesis.

AVP, AVPR1B Agonists and OXT Increase the Number of Hematopoietic Stem Cells and Progenitors In Vitro To analyze the effects of AVP and OXT on mouse hematopoietic stem cells and progenitors, mouse LSK cells were sorted and maintained them in culture for 2 days. At the initiation of the cell culture, the cells were treated with AVP or OXT, and for the last 24 hours their proliferation was followed using BrdU incorporation. As a negative control, cells were treated with a biologically inactive relative of AVP, desGlyAVP. AVP and OXT both induced proliferation of the cells studied, but the control peptide did not. The AVP and OXT dose-response curves were bell-shaped. The proliferation rates were highest at $10^{-12}$ M and $10^{-10}$ M (FIG. 2B).

Figure 2B:
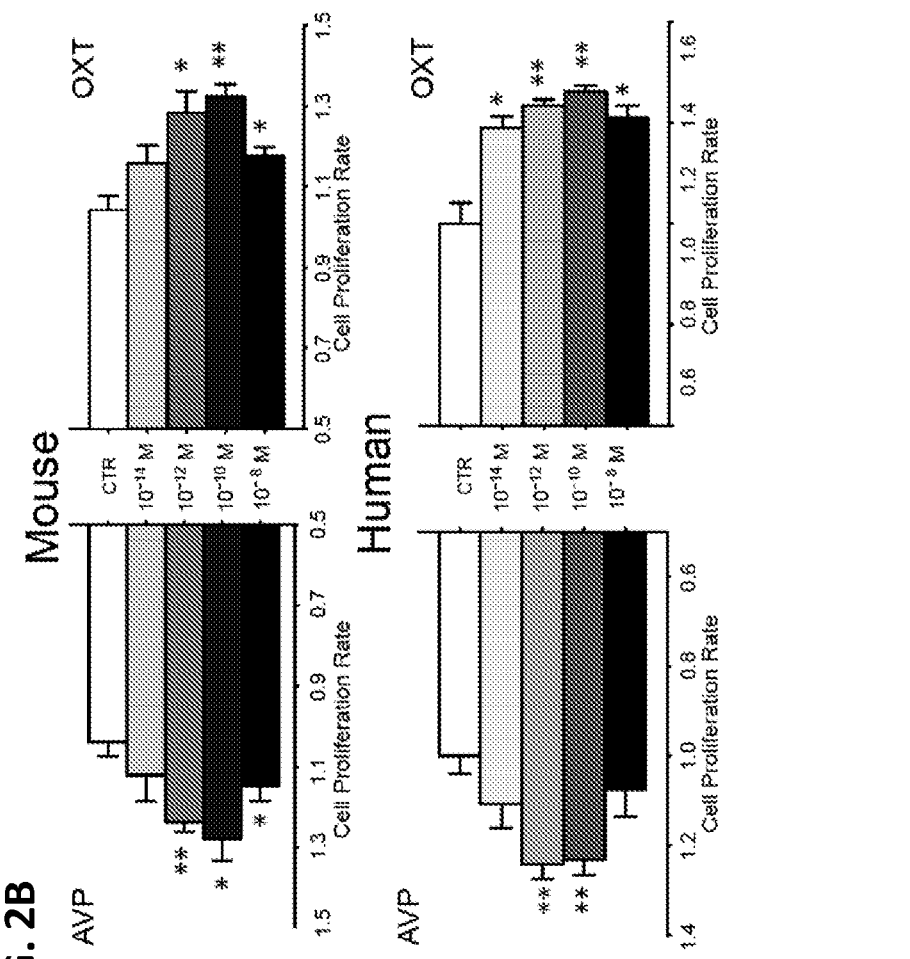
FIGS. 2A-2D show the effect of AVPR1B deficiency in vivo and AVP and OXT on hematopoiesis in vitro.
Figure 2A:
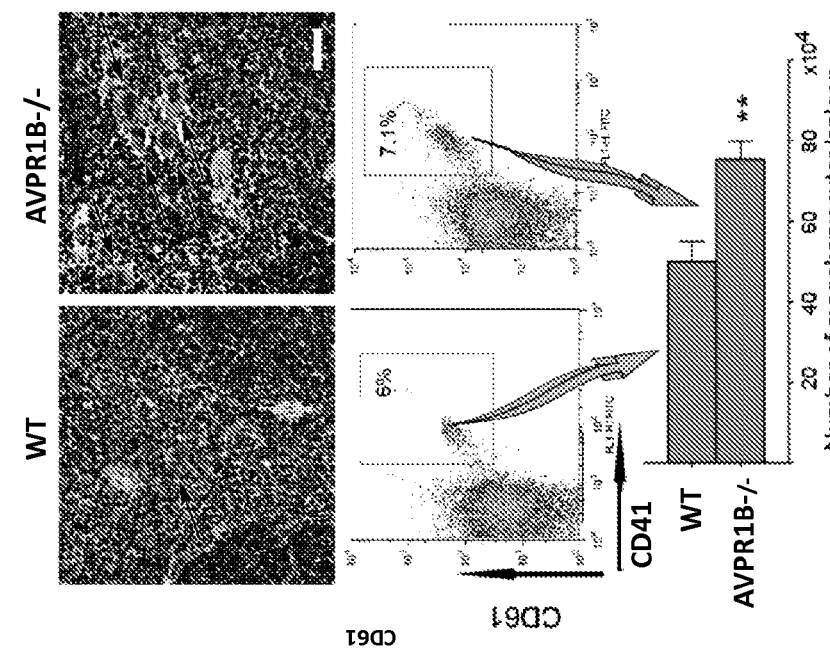
Figure 2D:
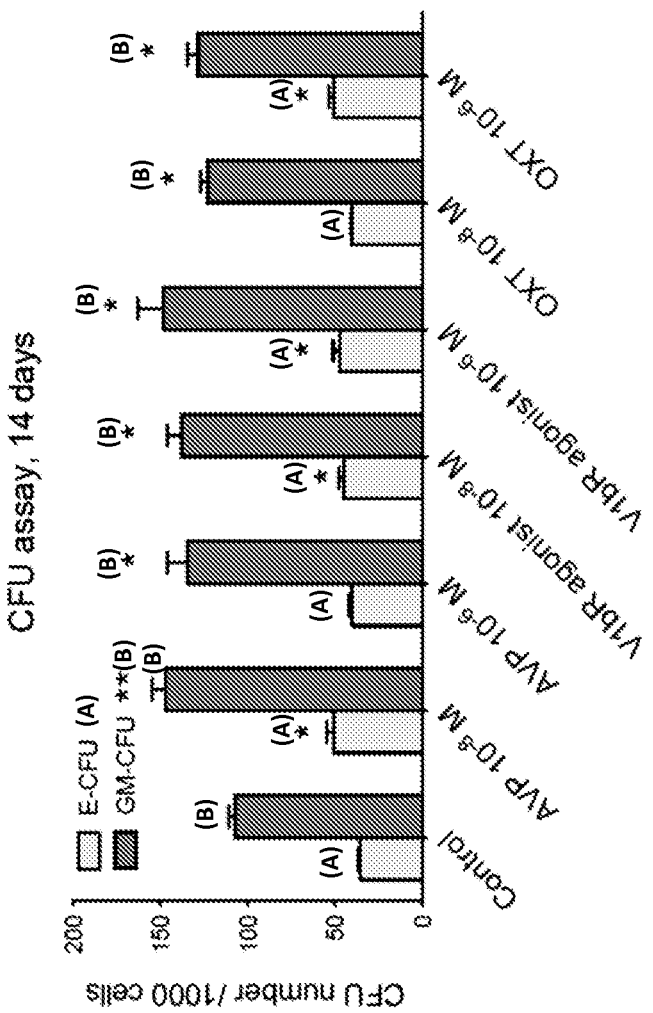
Figure 2C:
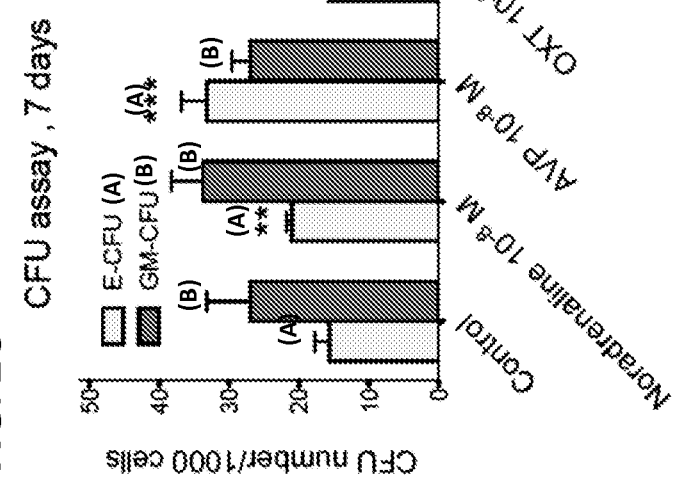

Human CD34+ cells responded to AVP and OXT in much the same way as mouse LSK cells did (FIG. 2B). Both AVP and AVPR1B agonist induced proliferation of human HSPCs that was blocked by a specific AVPR1B antagonist. Since the BrdU cell proliferation assay does not distinguish stem cells from progenitors, it was decided to perform a bone marrow competitive repopulation assay in mice, an assay that can pinpoint defects in the hematopoietic stem cell population. No difference was detected in the engraftment rate of WT versus AVPR1B KO bone marrow cells, raising the possibility that the major effect of vasopressin on hematopoiesis is on downstream progenitors versus HSCs. Colony forming unit assays were used to examine the effect of the peptides on CD34+ cells. Erythroid and granulocyte-macrophage colonies were grown in a selective semi-solid medium. AVP; an AVPR1B receptor agonist; OXT; or noradrenaline (a positive control) were added to the medium. Subsequently, the numbers of colony-forming units per 1000 plated CD34+ cells were counted (CFU numbers). AVP and noradrenaline at $10^{-8}$M significantly increased erythroid-colony forming unit (E-CFU) numbers (FIG. 2C). The AVPR1B receptor agonist increased both E-CFU and granulocyte macrophage-colony forming unit (GM-CFU) numbers, while OXT increased only GM-CFU numbers (FIG. 2D) indicating that the effect is more likely to be at the progenitor than the stem cell level. However, differences were observed among donors. AVP increased only E-CFU in cells from one donor studied but increased both E-CFU and GM-CFU in another. The disclosed data indicate that AVP, acting on the AVPR1B, increases both E-CFU and GM-CFU numbers, while OXT specifically increases GM-CFU numbers.

AVP Affects Wnt Pathway- and OXT Akt Pathway-Signaling

Figure 3A:
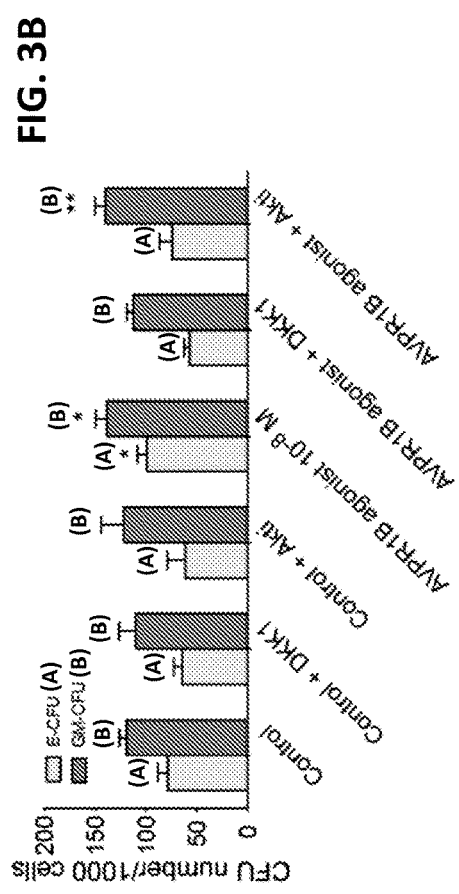
FIGS. 3A-3D show studies of signaling pathways.
Figure 3B:
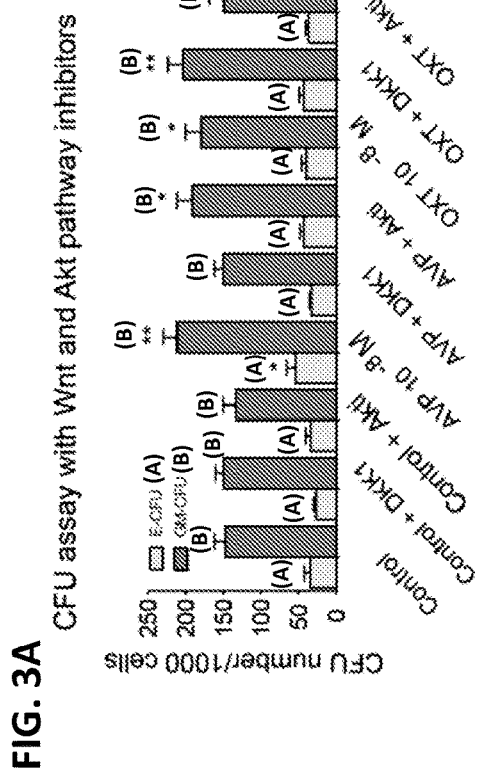

To pinpoint the molecular pathways involved in AVP- and OXT-induced hematopoiesis, human CFU assays were performed in the presence of pathway inhibitors for the Wnt, Akt, Sonic Hedgehog and Notch pathways, all of which are known to have roles in HSC proliferation, survival and differentiation. The Wnt pathway inhibitor Dickkopf-related protein 1 (Dkk1, 200 ng/ml) blocked the increase in GM-CFU numbers elicited either by $10^{-8}$ M AVP or AVPR1B agonist (FIG. 3A). HIMO ($10^{-8}$ M), an Akt inhibitor, had no effect on the response of cells to either AVP agonist (FIG. 3B), but it did block the increase in GM-CFU numbers induced by $10^{-8}$ M OXT. Dkk1 did not alter the cellular response to OXT. Neither Dkk1 nor HIMO affected GM-CFU numbers on their own.

Figure 3D:
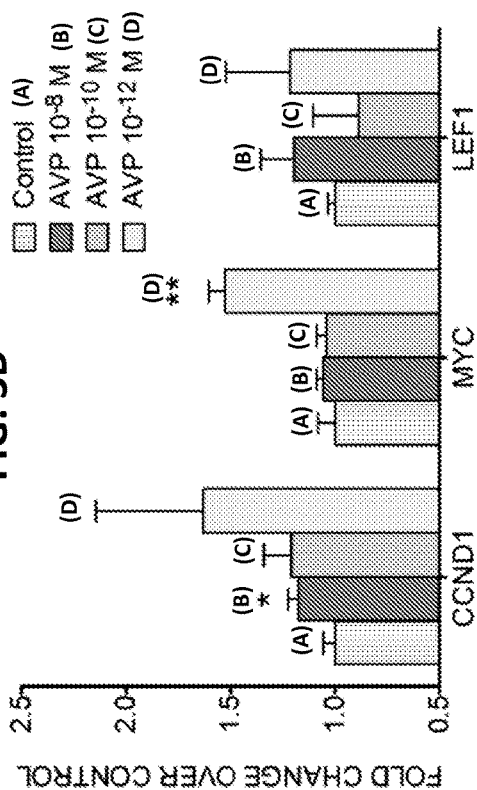
Figure 3C:
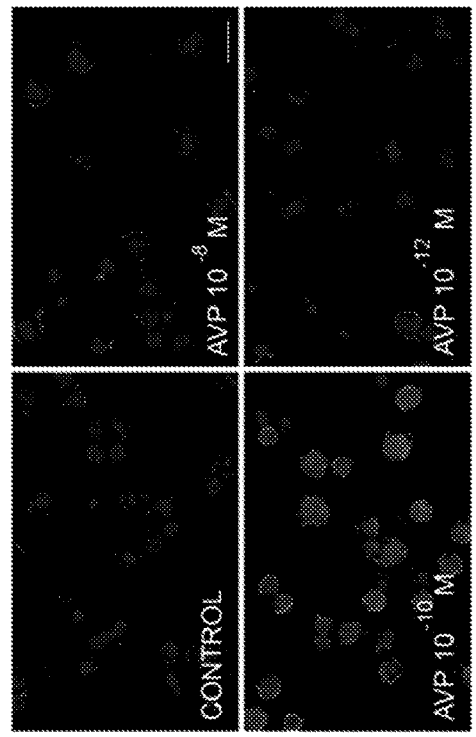

The idea that AVP affects Wnt pathway activation was supported by an additional study showing that the peptide at a concentration of $10^{-10}$ M drives nuclear translocation of β-catenin in CD34+ cells in vitro (FIG. 3C). RNA isolated from the AVP stimulated CD34+ cells had significantly more cyclin D1 (CCND1), and v-myc myelocytomatosis viral oncogene homolog (avian) (MYC) and an increase (statistically not significant) in the lymphoid enhancer-binding factor 1 (LEF1)—all markers of the Wnt pathway activation (FIG. 3D)—than control cells did. In a single microarray study of Wnt pathway activation (Superarray, SA Biosciences) an over two-fold difference in a number of genes was observed following AVP stimulation of CD34+ cells, such as CDON, DKK1, DPP10, FZD7 (upregulated) and CDKN2A, FST and KLF5 (down-regulated).

Changes in Peripheral Blood Counts in Response to AVP

To determine whether AVP could contribute to restoring peripheral blood counts in anemic animals, a variety of models were employed. In the first of these, blood was removed from C57BL6 male mice and an Alzet pump was used to deliver either AVP or vehicle to the animals for one week. Hematocrits were determined and corrected reticulocyte numbers 2, 4 and in most cases 6 days after the animals were bled. AVP treatment caused a significant increase in both markers 2 days post hemorrhage and a significantly higher hematocrit 4 days afterwards (FIG. 4A). In this same model of anemia the AVPR1B agonist also significantly improved RBC recovery (FIG. 4A). Although a hypothesis was that AVP has a role in hemorrhage induced anemia, it was also wondered whether AVP delivery could improve recovery from anemia induced by phenylhydrazine (i.e., hemolytic anemia) or by sublethal irradiation resulting in bone marrow damage. In both cases the delivery of AVP significantly improved outcome measures on day 2 and to some extent on day 4 (FIGS. 4B, 4C). It appears that AVP does not require the pathological environment produced by dehydration to stimulate hematopoiesis. The role of AVP was confirmed in recovery from anemia in another model: AVP-/- Brattleboro rats that suffer from diabetes insipidus were sublethally irradiated as were WT (Long-Evans, LE) controls. The vasopressin-deficient animals exhibited a marked lag in the recovery of their hematocrit and corrected reticulocyte numbers versus the LE controls (FIG. 4D). It was next determined if mice with AVPR1B-/- bone marrow could restore blood cell numbers as efficiently as animals with WT bone marrow following marrow ablation. After mice were lethally irradiated, they were transplanted them with either WT or AVPR1B KO bone marrow and looked at their hematocrits and corrected reticulocyte numbers. As FIG. 4E, 4F show, both of these returned to normal significantly faster in the mice with WT marrow cells.

Figure 4G:
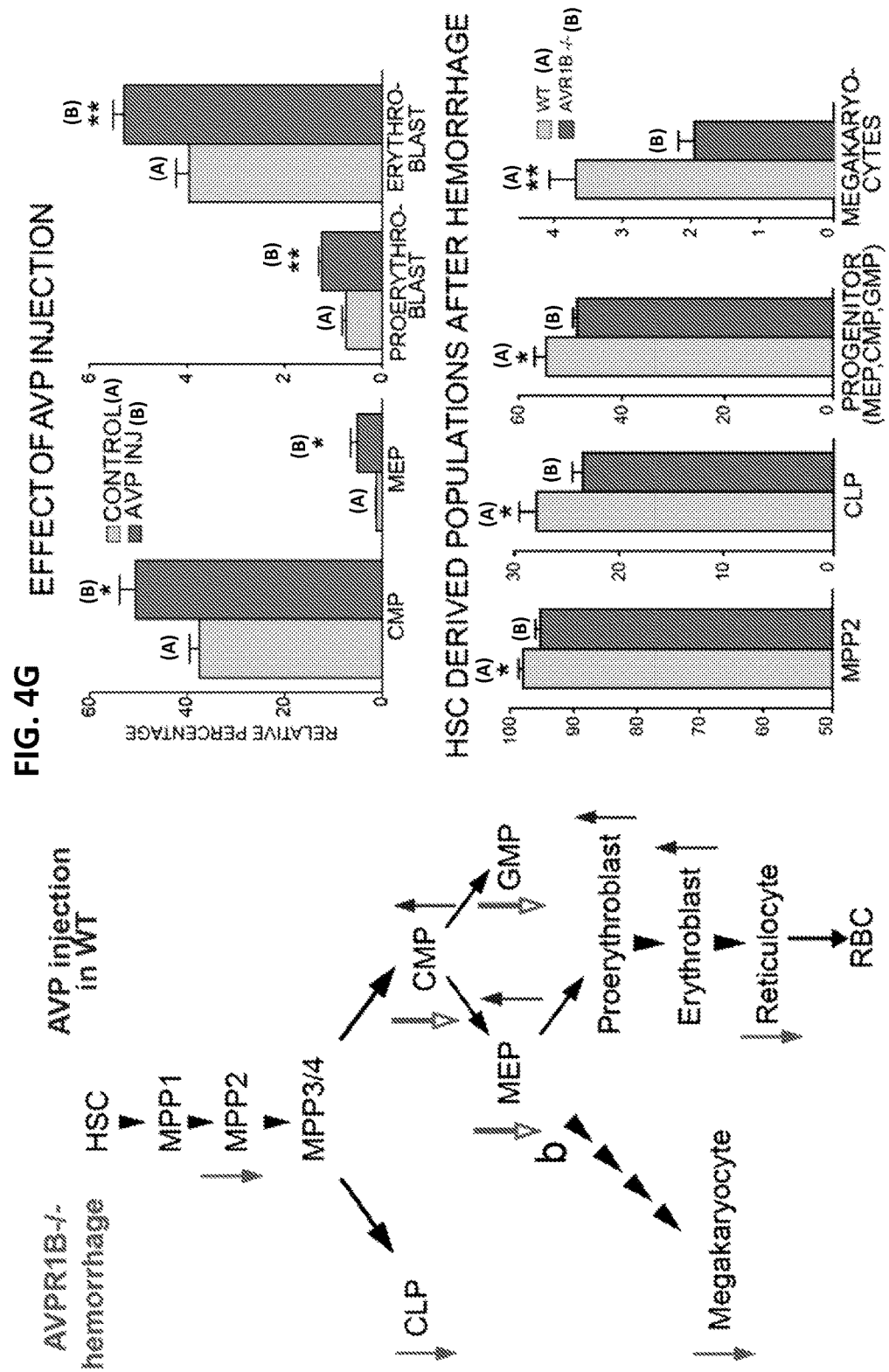

Finally, how AVPR1B KO mice would respond to blood removal was determined. After withdrawal of 25% of their blood, KO and WT mice were allowed to recover, and 2, 5, 9 and 16 days later hematocrit and reticulocyte values were determined. The reticulocyte index was significantly lower in the AVPR1B knockouts than in wild type animals 5 days after experimental hemorrhage. In parallel with this, decreased numbers of several hematopoietic progenitors were detected in the bone marrow of AVPR1B KO mice vs matched WT controls (FIG. 4G).

Changes in Bone Marrow Cell Populations in Response to AVP

To determine whether AVP affects various hematopoietic cell populations in the bone marrow in vivo, mice were injected intraperitoneally with AVP (i.p. 100 µg/kg body weight plus the protease inhibitor o-phenantroline 20 mg/kg body weight in PBS) or o-phenanthroline alone in PBS. 16 hours later bone marrow samples from the mice were evaluated and a significant increase in the number of red blood cell producing progenitors and blast cells (common myeloid progenitors, megakaryocyte-erythroid progenitors, proerythroblast, and erythroblasts) in the vasopressin injected animals was found. No difference was detected in the number of HSCs and early multipotent progenitors (MPPs) (FIG. 4G).

AVP and OXT are Made and Released by Bone Marrow Stromal Cells (BMSCs)

In some of the in vitro studies described above, AVP or OXT was applied to cells for many hours at relatively high concentrations, or injected into animals in large amounts. It is possible that following hemorrhage, for example, sufficient amounts of the hormones enter the marrow space in the blood to jump start hematopoiesis, but the possibility that there might also be a local source of the peptide hormones was also considered. Since the HSCs and the hematopoietic progenitors are surrounded and nurtured by the bone marrow stromal cells (BMSCs), the latter could potentially generate high local concentrations of AVP and/or OXT in response to the serum levels of these hormones. To address this hypothesis, first receptors for AVP/OXT receptors on BMSCs were looked at and it was found that on both mouse and human cells all of the receptors were present. Next it was determined if the BMSCs could also make AVP and OXT. RNA was isolated from cultured human and mouse BMSCs (and from human and mouse hypothalami to serve as positive controls). AVP and OXT transcripts were detected in the BMSCs and in hypothalamic samples using RT-PCR. When full flushed bone marrow cells (following lysis of red cells) were used no PCR product was generated, indicating that enrichment for BMSCs is necessary. While the BMSCs make much less mRNA than hypothalamic neurons do, it should be remembered that these neurons release their peptide products into the general circulation where they are greatly diluted and quickly metabolized. Cells like BMSCs may not need to secrete much hormone to have effects on HSPCs if they target their peptides to receptors on the surface of nearby cells.

To confirm the results of the RT-PCR study, the AVP- and OXT-precursor proteins in BMSCs were looked for using polyclonal antibodies for immunocytochemistry that recognize neurophysin II (AVP) or neurophysin I (OXT), carrier molecules that make up part of each peptide's precursor. In both mouse and human BMSCs, a punctuate staining pattern was observed in the cytoplasm suggesting that the peptides are stored in vesicles as they are in the terminals of hypothalamic neurons (FIGS. 5A, 5B and FIG. 5C, 5D). Cultured BMSCs spontaneously release both hormones (FIGS. 5E-5H).

Figure 5J:
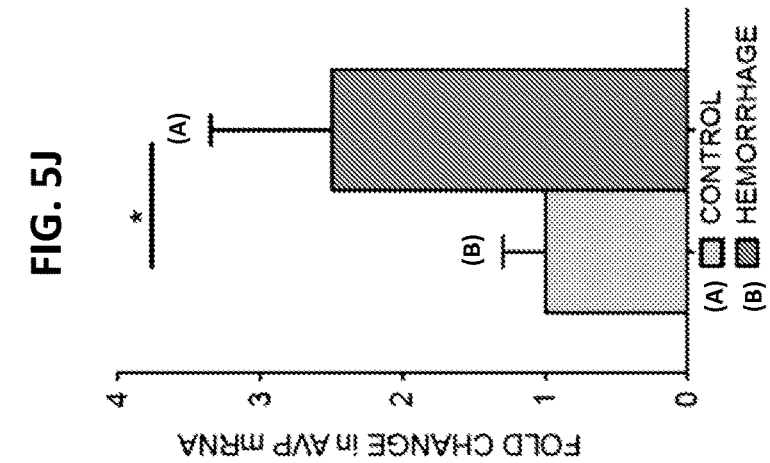
Figure 5I:
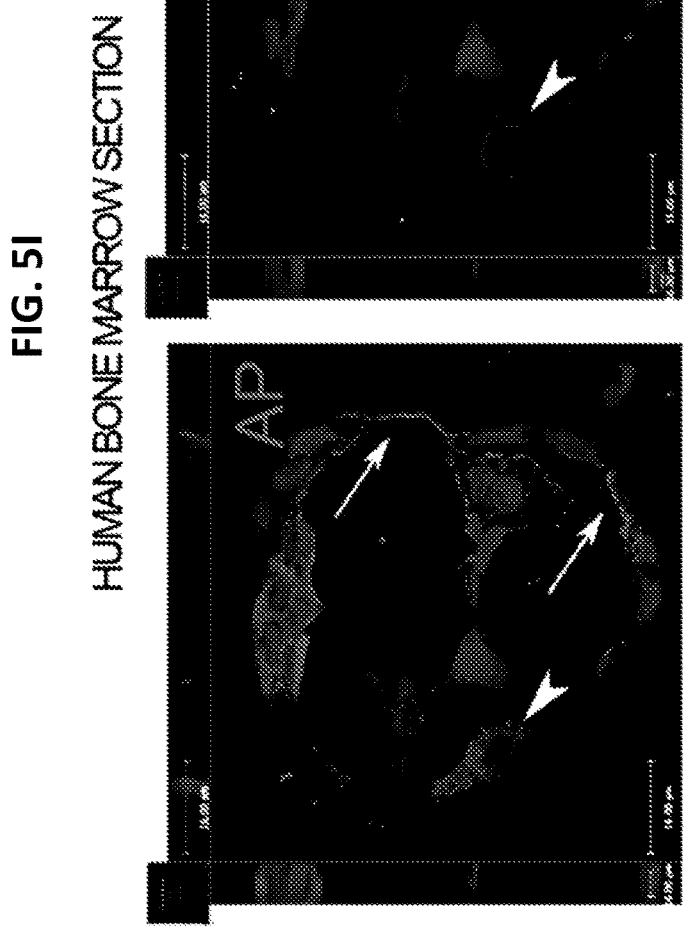

To show that the expression of AVP and OXT is not a result of culturing BMSCs, sections of decalcified human bone were fixed and stained. BMSCs in these samples, which were identified by alkaline phosphatase staining, were also positive for AVP and OXT (FIG. 5I). Some sections were stained with an anti-CD34 antibody and no AVP or OXT were found in $CD34^+$ cells. Instead, these cells were surrounded by AVP or OXT positive BMSCs.

AVP mRNA Levels Increase in BMSCs Following Hemorrhage

To determine whether AVP mRNA levels increase in BMSCs following hemorrhage, we isolated samples of the cells from mice after removing blood from them. After isolating the marrow we depleted lineage positive cells and then we performed fluorescence sorting for triple negative cells (CD31; CD45 and Ter119) to isolate the BMSC population. Following this, qPCR was used to measure the AVP transcript. In four independent studies, cells from animals that had undergone hemorrhage 30-120 minutes prior to sacrifice had 2 to 3.8 times more AVP mRNA than cells from control mice (FIG. 5L). PCR products were sequenced and found that their sequences were identical to mouse AVP cDNA. To confirm that the isolated cells were indeed BMSCs, functional tests were used to show that they could form colonies and make bone and adipose tissue when they were plated in the appropriate media. These studies indicate that AVP is able to induce its own release from BMSCs.

AVP-Induced AVP Release Stimulates $CD34^+$ Cell Proliferation In Vitro

Human hematopoietic progenitors ($CD34^+$ cells from healthy volunteers) and BMSCs derived either from Brattleboro rats or Long-Evans rats were co-cultured. A low concentration of AVP ($10^{-13}$ M) failed to induce proliferation of the $CD34^+$ cells in the presence of Brattleboro-derived BMSCs, but this same concentration of AVP did cause $CD34^+$ cells to proliferate when they were cultured in the presence of LE cells (FIG. 5K-5M). This indicates that AVP released by the LE BMSCs drives $CD34^+$ cell proliferation. It should be noted that protease inhibitors were added to the culture medium when these studies were done. It is not clear that concentrations of AVP as low as $10^{-13}$ M could stimulate HSPC proliferation in the marrow space, but based on the study described above, it is believed that BMSCs could amplify stimulatory signals intended for HSPCs (FIG. 5K-5M).

Discussion

Although the physiological roles of AVP and OXT as neurohormones and neurotransmitters have been investigated for over a hundred years, their effects on hematopoiesis have received little or no attention. In the late 1970s, Hunt and colleagues reported that cellular proliferation increased in bone marrow of rats following hemorrhage. After loss of blood, there were two peaks of mitotic activity—at 4 hours and 18 hours. Erythropoietin (EPO) appeared to drive the second wave of mitosis, while the first one disappeared following hypophysectomy and was not observed in Brattleboro rats (animals that lack AVP). The inventors concluded that AVP might be responsible for the first proliferative response, but the cell(s) in the bone marrow that responded to circulating AVP (and OXT) were never characterized, and the receptors and regulatory pathways involved were never examined. Both AVP and OXT act on G-protein coupled receptors. The AVPR1B receptor KO mice have an increased number of megakaryocytes in the spleen indicating that in such animals extramedullary hematopoiesis might compensate for a problem in the bone marrow. The spleen, which has a more important role in hematopoiesis in mice than in humans, is thought to be able to increase hematopoiesis because, unlike the marrow, its size is not constrained by space.

To confirm that AVP and OXT receptors are made by bone marrow cells, both RT-PCR and immunocytochemistry were used on previously sorted populations of BM cells. All three of the AVP receptors (AVPR1A, AVPR1B, AVPR2) and the OXT receptor are produced by mouse LSK cells; the AVPR1B and OXTR are produced by human CD34$^+$ cells. AVPR1B expression is higher in human CD34$^+$CD38$^+$ hematopoietic progenitor cells than in the more primitive CD34$^+$CD38$^-$ population suggesting that AVP might have a stronger proliferative effect on the more differentiated progenitor population.

Such an effect was looked for in vitro, and found that both AVP and OXT stimulated LSK proliferation. This was dose-dependent, exhibiting a bell-shaped curve. The proliferation rate was the highest at $10^{-10}$ M concentrations. The decrease of the cell proliferation at higher concentrations ($10^{-8}$ M) might reflect receptor desensitization at high peptide levels. The concentration of AVP in the human serum is normally 0.3-2×$10^{-12}$M. After blood is lost during surgery, the serum concentration of AVP increases to 0.5-1.0×$10^{-10}$M. OXT concentrations in venous dialysates in rats are $10^{-11}$ M at baseline and increase 14-fold after hemorrhage ($10^{-10}$ M). The above peak peptide concentrations after bleeding are consistent with those that resulted in the highest proliferation rate in our in vitro studies.

To study proliferation and differentiation of human CD34$^+$ cells, a selective AVPR1B receptor agonist, was used in addition to AVP and OXT.

AVP, AVPR1B agonist and OXT all increased proliferation and differentiation of human hematopoietic stem cells and/or their progenitors in vitro. Activation of the Wnt pathway appears to mediate the effects of AVP and an AVPR1B agonist while activation of the PI3K/Akt pathway seems to mediate the effect of OXT. Since these effects are specific (a Wnt inhibitor did not block the effect of OXT and an Akt inhibitor did not block the effect of AVP), it appears that the cells respond differently to the two hormones.

After it was found that AVP and OXT stimulate proliferation of mouse and human hematopoietic stem cells and progenitors in vitro, a similar effect of AVP and AVPR1B agonist was looked for in vivo. Infused over a 3 week period, AVP gradually increased RBC numbers in otherwise unmanipulated WT mice. In addition, AVP (and the AVPR1B specific agonist) appeared to stimulate reticulocyte production in animals that had lost RBCs to hemorrhage or hemolysis, or had lost bone marrow cells to irradiation. Transplanted bone marrow cells lacking AVPR1B receptors did not promote recovery of blood levels as effectively as WT cells did following lethal irradiation of the host mice, and rats that could not make AVP did not restore their RBC numbers to normal as quickly as WT rats did after sublethal irradiation. All of these studies indicate that AVP plays an important role in regulating hematopoiesis.

The inventors wondered if there might be a local source of AVP in the BM. This would be advantageous because 1) the hypothalamus would not have to release large amounts of hormones for long periods of time to trigger hematopoiesis, and 2) "supraphysiological" AVP concentrations, which could be harmful to the kidneys and other organs would not be needed for an optimal effect on the marrow. To explore the possibility of such local (paracrine) regulation of homeostasis, it was asked whether BMSCs, which are in close proximity to HSPCs, might make and release AVP and/or OXT. This was indeed the case in vitro (FIGS. 5A-5H). Furthermore, both AVP and OXT induced ERK phosphorylation and when AVP or an AVPR2 agonist were added to BMSC cultures, there was an increase in cyclic AMP, but not intracellular calcium suggesting that the AVPR2 might be responsible for the effect of AVP on BMSCs. In the case of OXT stimulation we observed an increase in intracellular Ca$^{2+}$ concentrations. Thus, it seemed possible that AVP in the blood might stimulate its own release from BMSCs. The AVP released might have an autocrine action that provides positive feedback to these cells as well. The data shown in FIGS. 5K-5M support this hypothesis. A much lower concentration of AVP is required to stimulate HSPC proliferation in vitro in the presence of BMSCs than in their absence. This is not to say that circulating AVP is the only agent that might be capable of releasing BMSC vasopressin. Angiotensin II, which is also released following hemorrhage, might also do this. In addition, factors other than AVP may be secreted by BMSCs after blood loss and contribute to proliferative response of HSPCs observed.

Based on these results, it was hypothesized that elevated levels of AVP might have multiple roles in animals that have lost blood. It acts on the AVPR2 receptors in the kidney to stimulate water resorption to compensate for the volume loss. It also helps to stop the bleeding by releasing von Willebrand factor from endothelial cells. Simultaneously, AVP stimulates hematopoiesis driving the replacement of lost erythrocyte and myeloid cells. AVP seems to drive both erythroid and myeloid cell production. The AVP involved in blood cell replenishment appears to come from two sources: the posterior pituitary and BMSCs. The latter seem to function as local amplifiers of hematopoiesis (FIG. 6). They embrace HSPCs and the factors that they secrete may reach considerably higher concentrations at the HSPC surface than those present in the remainder of the BM niche. Thus, AVP may jumpstart the proliferation of HSPCs. Later, this is likely to be maintained by EPO.

Currently, EPO is the only agent that is used clinically to stimulate hematopoiesis, but there are patients who do not respond to EPO or who cannot take the drug. The studies disclosed herein indicate that a peripherally active AVPR1B agonist can be used to treat patients with anemia due to chemotherapy. Alternatively, nicotine, a potent stimulant of AVP release from the posterior pituitary, can be used for this purpose. In fact, cigarette smokers are known to have high hematocrits that tend to normalize when they stop smoking.

Example 3

Arginine Vasopressin Drives a Rapid Response to Hemorrhage by Boosting Erythropoiesis This example demonstrates that arginine vasopressin drives a rapid response to hemorrhage by boosting erythropoiesis. When the inventors discovered that mRNAs encoding arginine vasopressin (AVP) receptors were made by hematopoietic stem and progenitor cells in the bone marrow, the inventors next determined whether AVP might boost red blood cell production following hemorrhage in addition to stimulating water retention. The inventors discovered that the hormone indeed induced proliferation of hematopoietic progenitors and stimulated early erythroid colony formation in vitro. It is contemplated that these effects are mediated by nuclear translocation of beta-catenin. In vivo, vasopressin had similar actions—it stimulated the proliferation and differentiation of progenitor and erythroid cell populations, and promoted the release of young reticulocytes into the bloodstream. The AVP induced effect on peripheral blood cell recovery was significantly faster than the effect of erythropoietin (EPO), the best known stimulator of red blood cell production. Through this rapid effect AVP may bridge the gap, while the EPO initiated erythropoiesis can result in an increased oxygen carrying capacity at the periphery—which takes 3-5 days. Thus, the antidiuretic hormone, arginine vasopressin, stimulates the proliferation and differentiation of red blood cell precursors in the bone marrow, replenishing cells in the blood before erythropoietin starts working.

The AVPR1B receptor is at least partly responsible for mediating these actions, and they are independent of EPO. Thus, these studies indicate that a specific AVPR1B agonist nicotine, which stimulates AVP release from the posterior pituitary) can be used to "jumpstart" erythropoiesis or promote it in patients who cannot be given EPO.

Following hemorrhage, a compensatory increase in red blood cell production (erythropoiesis) is needed. This increase is thought to be driven mainly by erythropoietin (EPO), a hormone made by specialized cells in the kidney. EPO appears to affect the survival, proliferation, and differentiation of erythroid progenitor cells. It does not act very rapidly, however. Three to four days pass before immature red blood cells (reticulocytes) are seen in the blood after EPO administration.

Following hemorrhage, another hormone, arginine vasopressin (AVP) is immediately secreted from nerve endings in the posterior pituitary. Its antidiuretic effect on the kidney helps to restore fluid balance. When a screening assay revealed that a pool of hematopoietic stem cell and progenitor cells (HSPCs) made AVP receptor mRNAs, it was then determined whether AVP might also stimulate red blood cell production to help overcome acute anemia. The first step was to confirm the presence of the receptors in these cells.

AVP Receptors and the mRNAs that Encode them are Made by Murine and Human Hematopoietic Progenitor Cells Hematopoietic stem cells (HSCs) and their progeny are defined by certain functional hematological assays. HSCs need to ensure serial long-term and multi-lineage repopulation of bone marrow ablated subjects. Progenitor cells are required to form relevant colonies in vitro supported by an appropriate cytokine milieu. There is still ongoing research to further characterize and catalogue the different hematopoietic cell populations and to find unique, selective cell surface markers. HSCs (CD34$^+$/CD38– cells) give rise to a series of lineage-restricted cell types that become progressively more differentiated, and less proliferative. Multipotent progenitors (MPPs) are followed by common lymphoid progenitors (CLP) or common myeloid progenitors (CMP); the latter will give rise to the megakaryocyte/erythroid progenitors (MEPs), which produce megakaryocytes and members of the erythroid lineage. Red blood cells (RBC) are derived from several cells in succession: burst-forming unit-erythroid cells (BFU-E), colony-forming unit-erythroid (CFU-E) cells, proerythroblasts, basophilic, polychromatic and orthochromatic erythroblasts. The stem, multipotent and lineage committed progenitor and erythroblast precursor cells are all nucleated, but after blast cells mature into orthochromatic erythroblasts they extrude their nuclei, yielding young reticulocytes that still contain RNA and cellular organelles. The reticulocytes lose surface area, volume, and cytoplasmic organelles on the way to becoming mature erythrocytes.

Figure 7A:
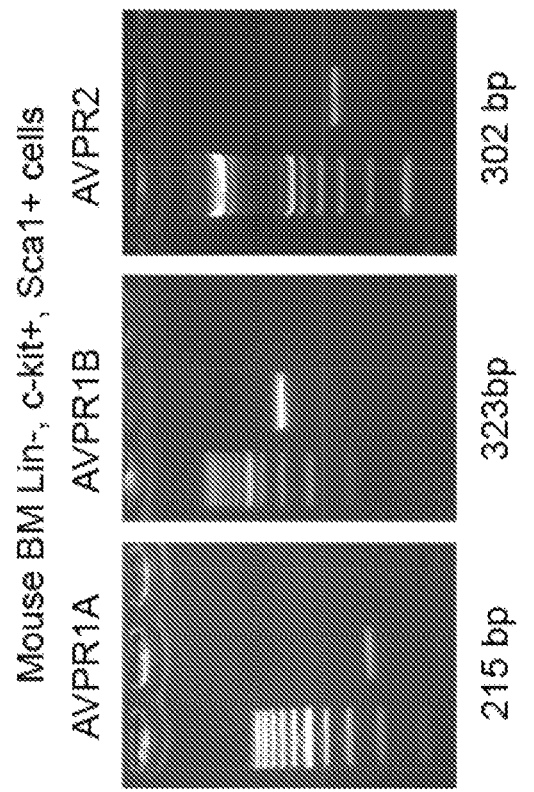
Figure 7B:
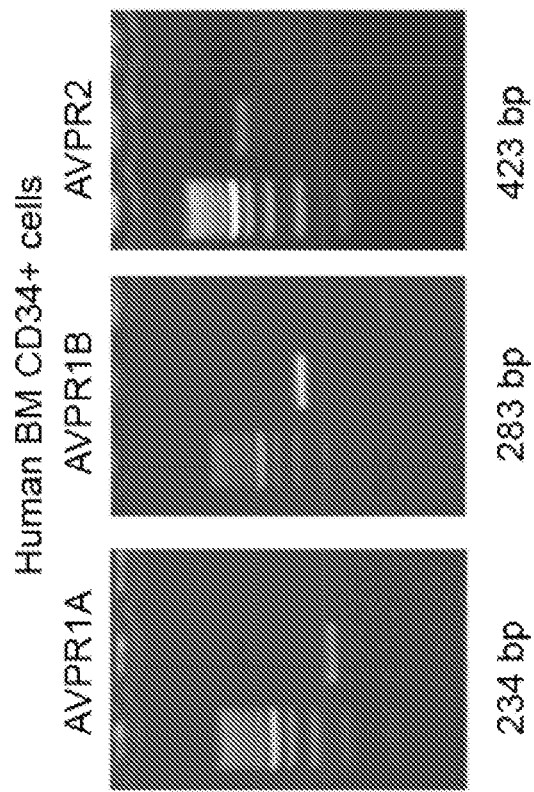
Figure 7C:
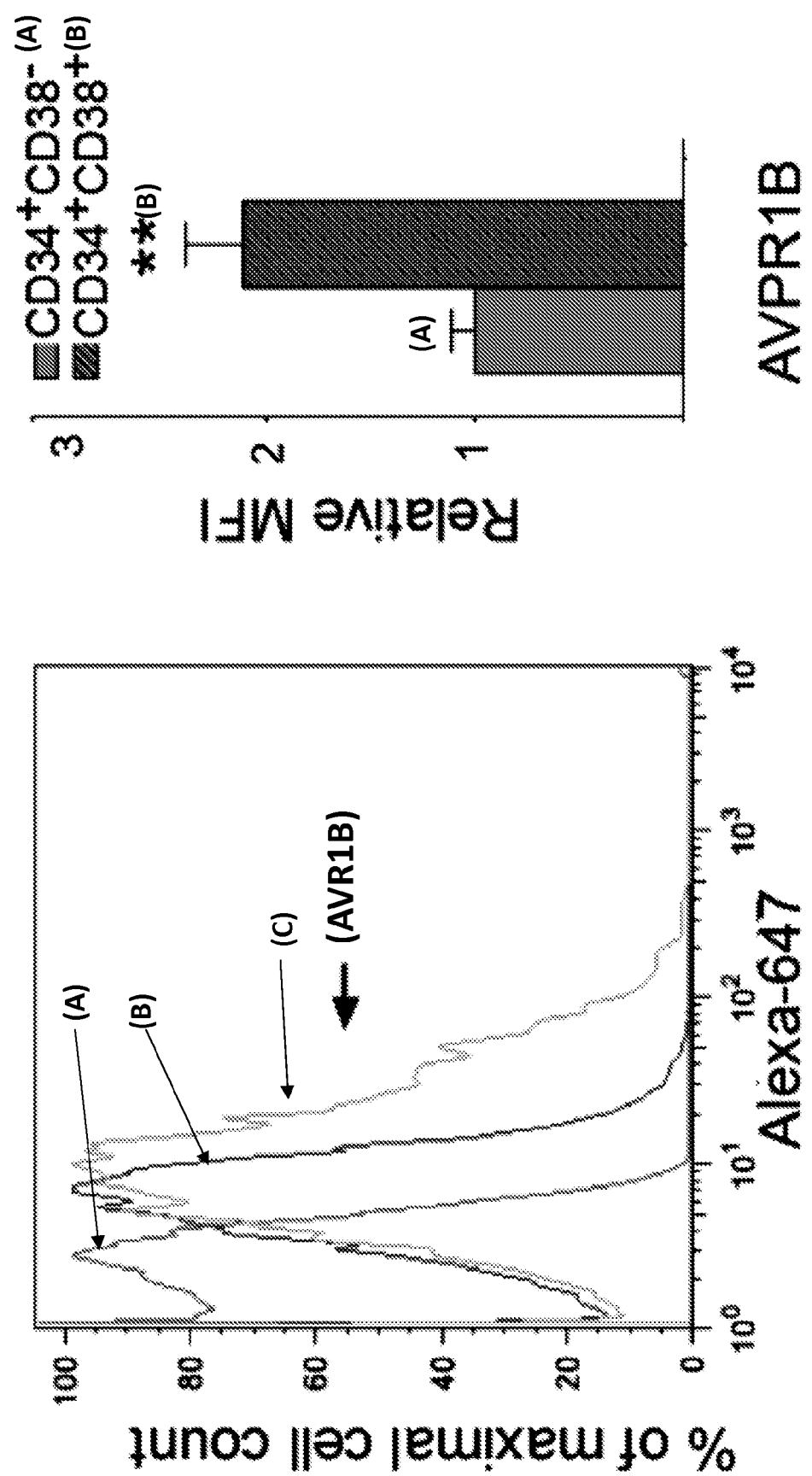
Figure 7D:
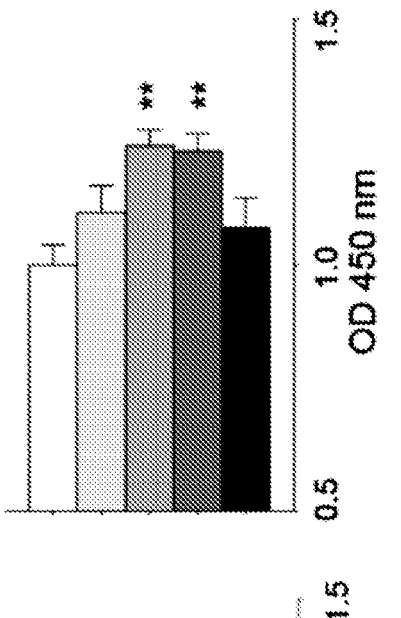
Figure 12:
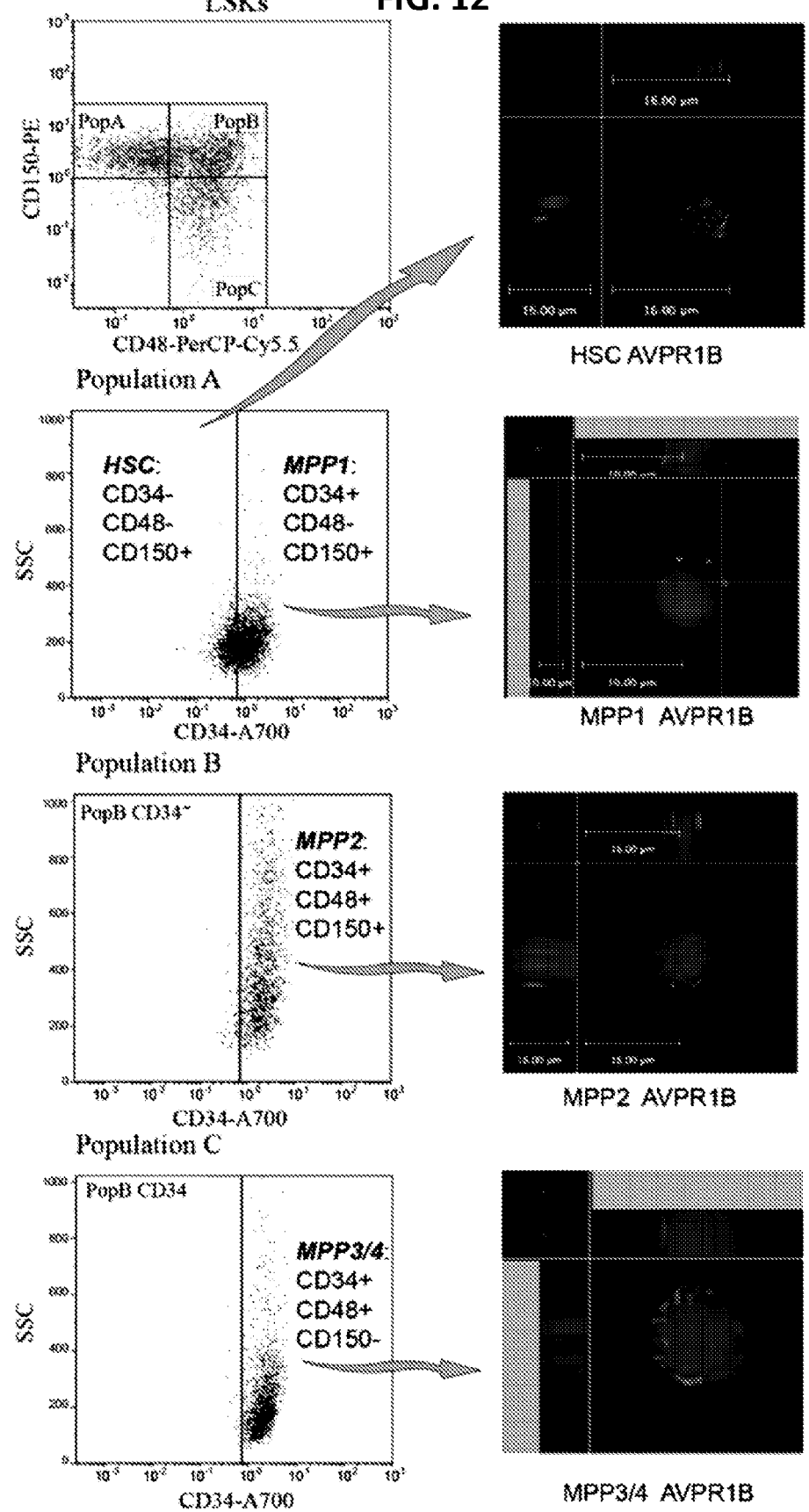
FIG. 12 is ICC demonstration of AVPR1B in mouse hematopoietic progenitors. Hematopoietic progenitor cells were sorted from C57BL/6 bone marrow using a variety of markers. After isolating cells of the different groups, the cells were fixed onto microscope slides and immunocytochemistry was performed to detect the AVPR1B. The detailed technique, controls and the antibodies used are listed in Example 1. After immunostaining, the sections were analyzed using Z series (0.2 µm) and iterative restoration was performed using a Leica DMI6000 inverted fluorescent microscope and Volocity (Perkin-Elmer) software. The immunostaining for the AVPR1B was visualized in all four populations of cells.

The presence of vasopressin receptors in a population of hematopoietic stem and progenitor cells (HSPCs) was determined. Using a microarray-based method the inventors found that hematopoietic progenitors (human CD34$^+$/CD38$^-$ and CD34$^+$/CD38$^+$ cells) make mRNAs that encode AVP receptors. As shown in FIGS. 7A and 7B, mRNAs encoding all three of the AVP receptors could be detected in both human and murine HSPCs. The AVPR1B receptor mRNA appeared to be the most abundant of the three. While an antibody is available that can be used to identify the AVPR1B on sorted cells, antibodies that can be used to detect AVPR1A and AVPR2 receptors are not commercially available. AVPR1B receptors were present on human primitive hematopoietic cells and on more committed progenitors: CD34$^+$/CD38$^-$ and CD34$^+$/CD38$^+$ cells, respectively. They are twice as abundant on the latter (FIG. 7C, right), and are readily detectable on murine MPP1 (FIG. 7D), MPP2 and MPP3/4 (FIG. 12) cells using immunocytochemistry.

AVP Induces Proliferation of Hematopoietic Progenitors

Figure 7E:
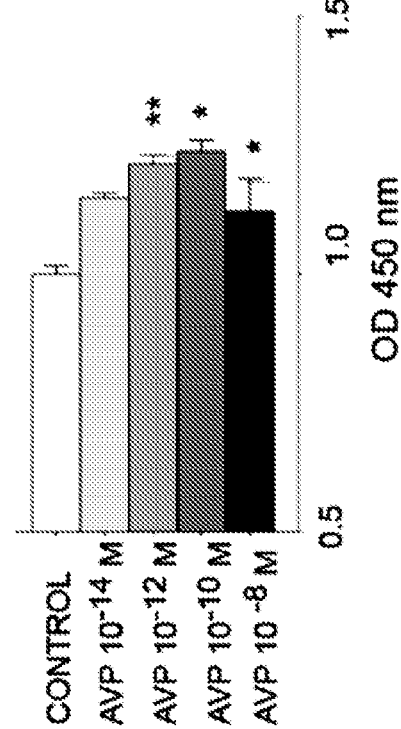
Figure 7F:
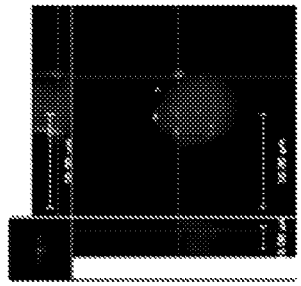

Using BrdU to detect proliferation, we showed that AVP significantly increased the proliferation of cultured murine (FIG. 7E) and human HSPCs (FIG. 7F). The effects of the peptide were greatest at concentrations between $10^{-12}$ and $10^{-10}$ M, ones that are achieved in blood.

Figure 13:
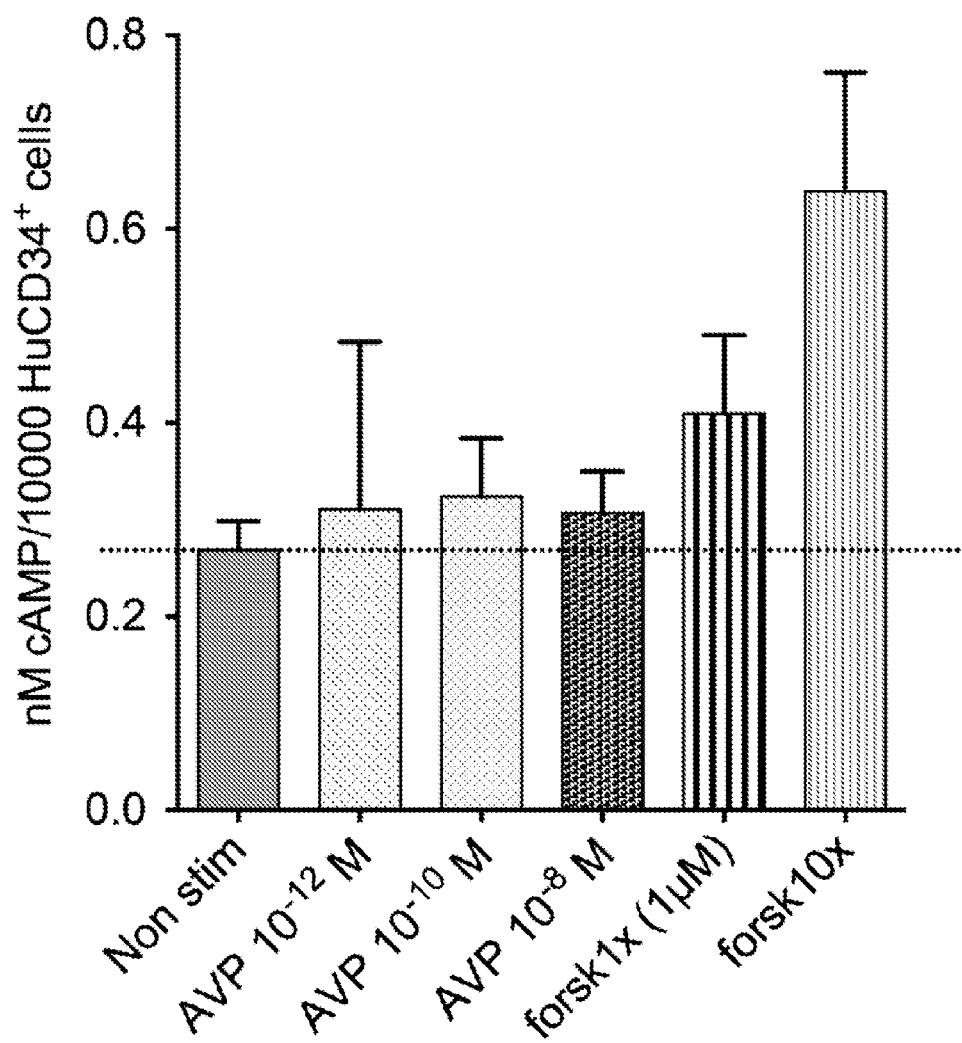
FIG. 13 illustrates AVP stimulation in HuHSPCs increases cAMP concentrations. In two consecutive studies, 10,000 and 100,000 CD34 progenitor cells were plated from two different donors. AVP ($10^{-10}$ M) caused an elevation in cAMP levels compared to the non-stimulated cells. Non-stimulated cells served as negative control and forskolin was used as positive control in both studies.

Stimulation of vasopressin AVPR1A and AVPR1B receptors preferentially in-creases intracellular calcium. Stimulation of AVPR2 receptors increases cyclic AMP. To learn more about the mechanisms that might underlie the proliferative responses we observed, we looked for increases in calcium ion and cyclic AMP concentrations in human progenitor cells. An increase in intracellular calcium was found using AVP or a specific AVPR1B (but not AVPR1A) agonist (FIG. 7G) in human CD34+ progenitors; this effect could be blocked by an AVPR1B antagonist. AVP stimulation also resulted in a moderate increase in cAMP in human CD34$^+$ progenitors. In two consecutive experiments, 10 k and 100 k CD34 progenitor cells were plated from two different donors. AVP $10^{-10}$ M caused an elevation in cAMP levels compared to the non-stimulated cells (FIG. 13). Non-stimulated cells served as negative control and forskolin was used as positive control in both experiments. While this is likely to have been caused by AVPR2 activation, it is also possible that AVPR1B receptors were involved.

Figure 7H:
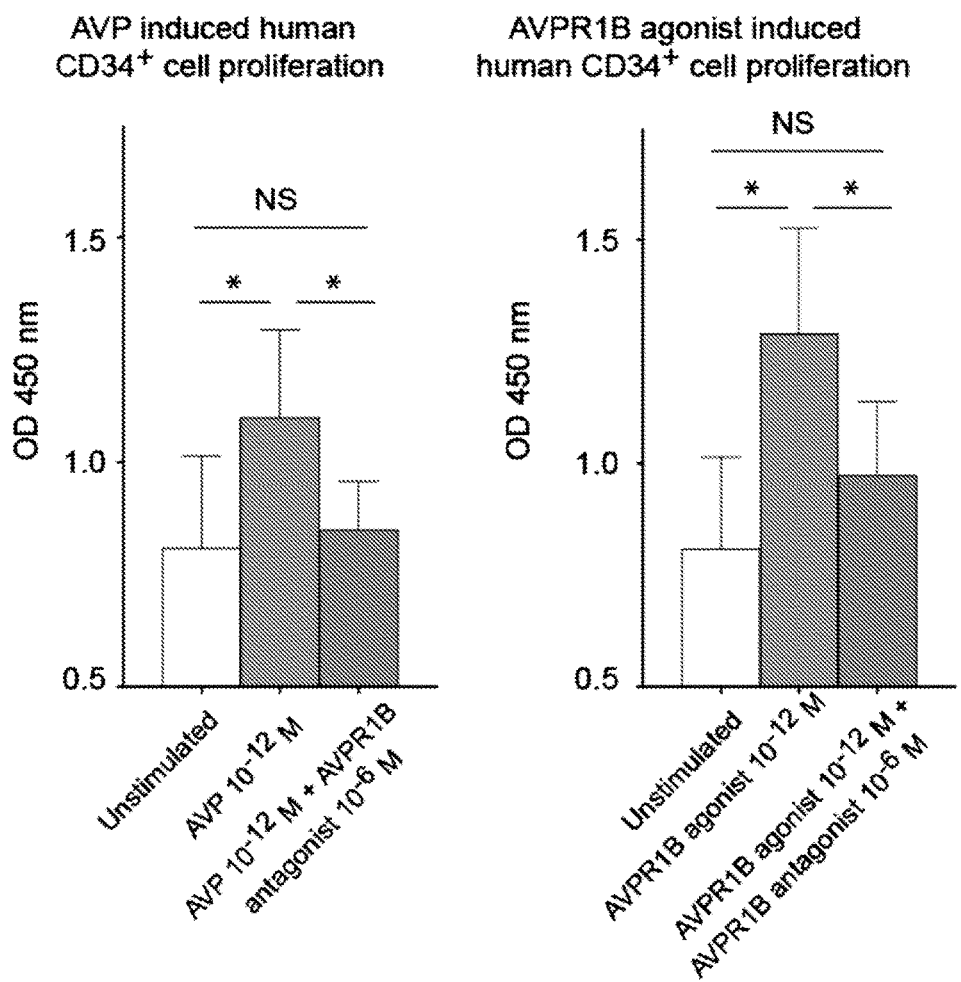

Since AVPR1B receptors are the most abundant subtype on HSPCs and appear to be functional, whether a specific AVPR1B antagonist could block the proliferative effect of AVP on human cells and whether a specific agonist could mimic it was evaluated. As shown in FIG. 7H, both effects were seen. These results indicate that AVPR1B receptors play an important role in mediating progenitor cell proliferation but they are not exclusively responsible for the effects of AVP.

Since differences in both erythroid and myeloid lineages were observed when analyzing the BM from WT versus AVPR1B knockout (KO) mice a competitive repopulation assay was performed to determine if the lack of the receptor exclusively in the BM would result in a disadvantage in repopulation following irradiation. Peripheral blood was examined at 1, 2, 3 and 4 months and spleen and BM cells at 4 months following the transplantation. No difference was found between CD45.1 recipient mice transplanted with CD45.2 WT versus CD45.2 AVPR1B KO BM cells that competed against transplanted CD45.2 Z/EG BM cells in physiological circumstance (no stress was induced on the BM in these mice) (FIG. 14). Since this assay is relevant to the HSC function and the lymphoid (CD3, B220 markers) and myeloid (Gr-1, CD11b markers) lineages, and no difference was found between the groups, the erythroid lineage was further characterized.

AVP Induces Early Erythroid Colony Formation

Figure 7I:
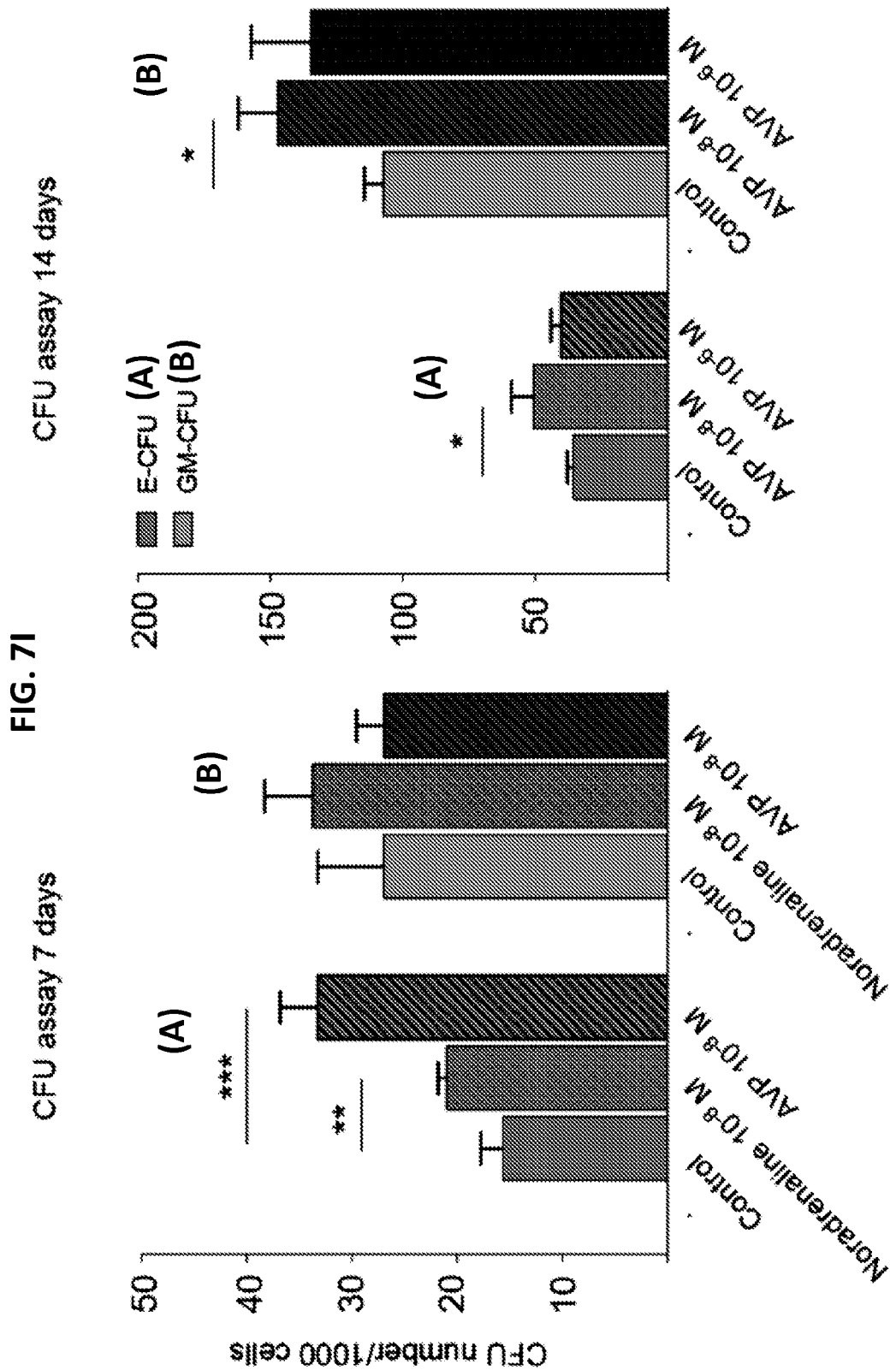

To learn whether the progenitor cells that proliferate in response to AVP give rise to erythrocytes, granulocytes/macrophages, or both cell lineages, Colony Forming Unit (CFU) assays were employed. In these assays, AVP is added at the beginning of the study and not replenished. Since it is gradually degraded, higher concentrations of the peptide are required than those used in the assays of proliferation described earlier. AVP increased erythroid colony formation (FIG. 7I) in cells from all three human donors studied, although the increase appeared to be donor-dependent. Also, granulocyte macrophage colony numbers (GM-FCU) were increased in cells from two donors. In one of the donor cell samples, AVP increased only E-CFU colony numbers at day 7, even more than the positive control (noradrenaline) did. By day 14 both E-CFU and GM-CFU from all donors were stimulated.

AVP Stimulates Wnt Signaling and Drives Nuclear Translocation of β-Catenin

Activation of the canonical Wnt pathway, resulting in translocation of β-catenin into the nucleus, can stimulate proliferation of HSPCs. At a $10^{-10}$ M concentration, AVP had this effect (FIG. 8A). Therefore, whether DKK-1, an inhibitor of Wnt signal transduction, could prevent vasopressin-stimulated colony formation was p. Indeed DKK-1 did block the effect of AVP in the CFU assays, but HIMO (Akti, $10^{-8}$M), an inhibitor of Akt had no effect (FIG. 8B). dCha$^4$AVP, a selective AVPR1B receptor agonist, also stimulated colony formation and was inhibited by DKK-1 (FIG. 8C).

AVP Deficient Rats Recover from Anemia Slowly

Figure 9A:
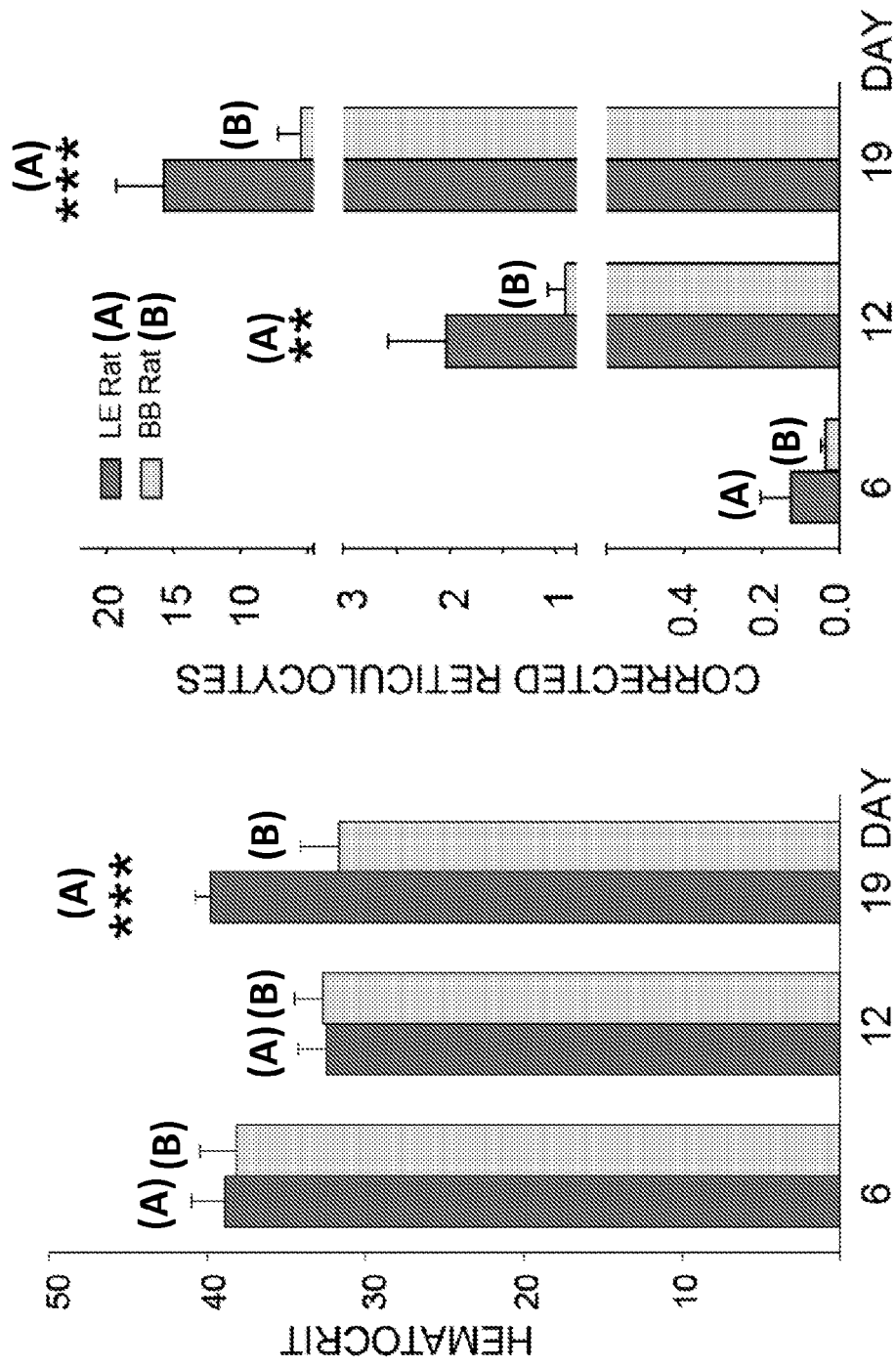

The effects of AVP in vivo were determined by studying Brattleboro rats, animals with a frame-shifting mutation in the AVP gene that impairs procession and secretion of the peptide. The animals were exposed to sublethal levels of irradiation and then monitored their reticulocyte and hematocrit levels over time. As FIG. 9A indicates, reticulocyte counts rebounded more quickly in WT than AVP-deficient rats. By day 19, WT animals also had significantly higher hematocrits. In this study, AVP (in the WT animals) may have acted in vivo in much the same way that it acted in our in vitro studies—by stimulating HSPC proliferation after cells in the marrow were partially destroyed. This is a relatively slow process, and the inventors then wondered if AVP could have more rapid effects.

AVP Increases the Sizes of Progenitor and Erythroid Precursor Cell Populations In Vivo When AVP was injected into wild-type mice, we found a statistically significant increase in sizes of the CMP, MEP populations and in the number of proerythroblasts and erythroblasts 16 hours later (FIG. 9B). To establish if this effect of AVP was a direct effect the inventors next evaluated how the BM of mice that lack the AVPR1B respond to AVP release triggered by hemorrhage. Significantly fewer cells were found in all progenitor populations (MPP2, CLP, MEP, CMP, GMP) and fewer megakaryocytes in the AVPR1B KO mice than their WT counterparts (FIGS. 9B and 9C) indicating the direct involvement of the AVPR1B in response to AVP.

Figure 9D:
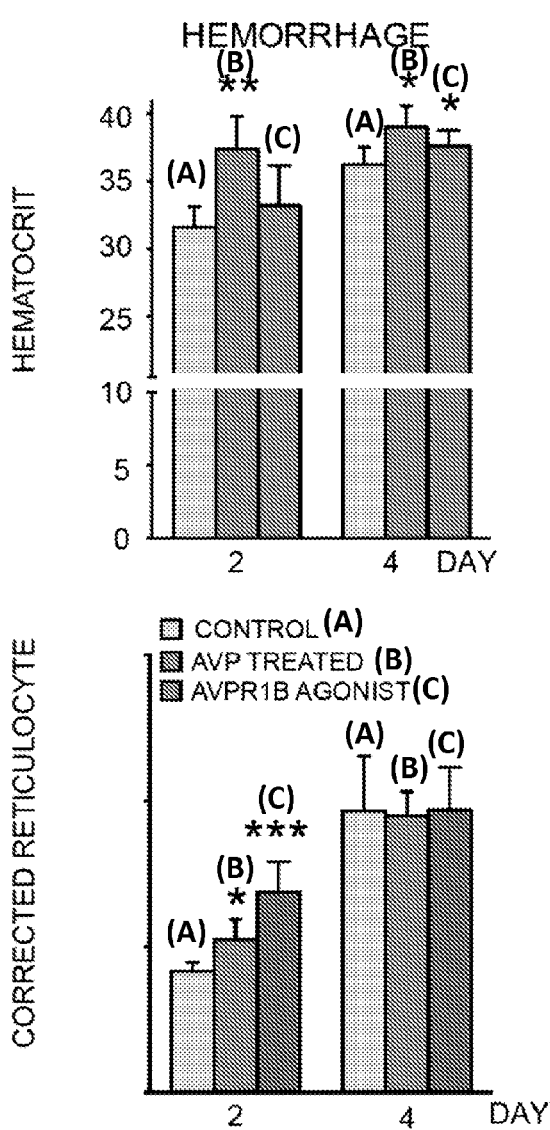
Figure 9E:
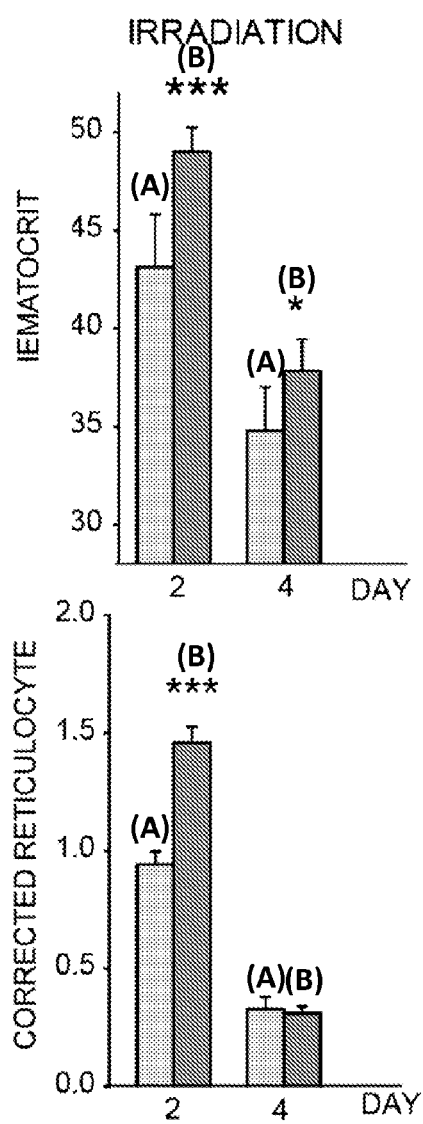

To determine if this peripheral recovery of blood cells occurs in the mice, 25% of the blood volume was acutely removed from mice, and divided them into three groups, the members of which received no treatment, AVP or an AVPR1B agonist. By day 2, reticulocyte numbers had increased in the blood of the AVP and AVPR1B agonist treated mice (FIG. 9D). Between days 2 and 4, their hematocrits also increased. Treating sublethally irradiated mice with vasopressin also resulted in rapid elevations in hematocrit and reticulocyte numbers (FIG. 9E). In these studies, FACS analysis based on a nucleic acid stain (thiazol orange) was used, since young reticulocytes still have large amounts of RNA (following the extrusion of the nucleus). It was observed that AVP significantly increased the number of highly fluorescent (high intensity) reticulocytes, suggesting a quick release of immature cells from the BM.

Figures 9F, 9G:
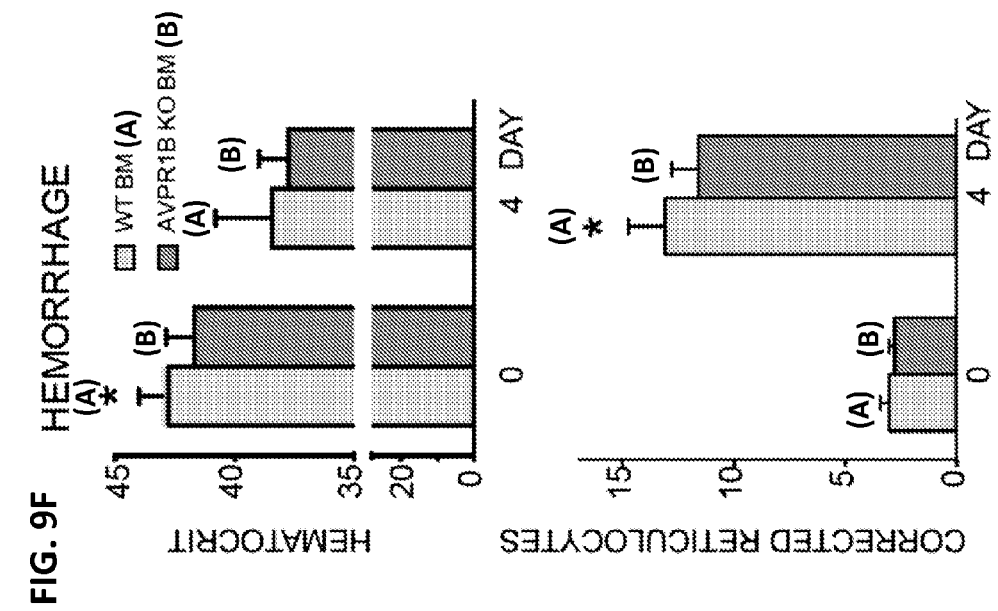

AVPR1B is at Least Partly Responsible for the Effect of AVP on Recovery from Anemia Irradiated mice were transplanted with AVPR1B KO or WT littermate BM. After they recovered, blood was removed from the mice (FIG. 9F) or treated them with phenylhydrazine (FIG. 9G) to induce anemia. Following hemorrhage, peripheral blood cells and volume are lost; following phenylhydrazine treatment, RBCs are lysed, but there is no volume loss. In both cases, mice with AVPR1B KO BM had a significantly slower recovery of their peripheral blood cells than animals transplanted with WT marrow.

Splenectomy does not Alter the Effect of AVP on Recovery from Anemia

The in vivo effects could have a number of underlying mechanisms. In anemic mice, the spleen has been implicated in extramedullary regeneration of blood cells. Cells stored in the spleen could quickly be released into the circulation to increase cell numbers there. To test this hypothesis the inventors performed splenectomies and subsequently subjected the animals to hemorrhage. The AVP-induced hematocrit response in splenectomized mice was no different from controls, indicating that the spleen did not play a significant role in quickly replacing red blood cells in mice in response to AVP (FIG. 15).

The Rapid Effect of AVP on Hematocrit is Independent of EPO

Next it was determined if AVP released EPO to restore blood cell numbers. Two studies were designed to answer this question: in the first study wild type mice were injected with EPO or AVP just after hemorrhage, and hematocrit values at different time points afterwards were analyzed. AVP stimulated an increase in hematocrit compared to PBS 6 hours after hemorrhage, but the increase was only statistically significant at 12 and 24 hours. Differences between EPO and AVP were significant at 6, 12 and 24 hours and disappeared 5 days after hemorrhage (FIG. 10A).

In a second study (FIG. 10B) we injected mice with AVP or PBS in control groups and following hemorrhage used an EPO neutralizing antibody to eliminate the effect of EPO. Even after EPO neutralization, AVP significantly increased hematocrit values. There was no significant difference in corrected reticulocyte (CR) values in the anemic mice between the EPO neutralized or control groups following administration of AVP or PBS at day 2. At day 4 and 6 the AVP increased the CR values over PBS in control mice. EPO neutralization eliminated this difference at day 4, but by day 6 AVP began to increase CR numbers even in the EPO neutralized group.

AVP Induces Differentiation of Erythroblasts and Releases "Shift" Reticulocytes

Figure 10C:
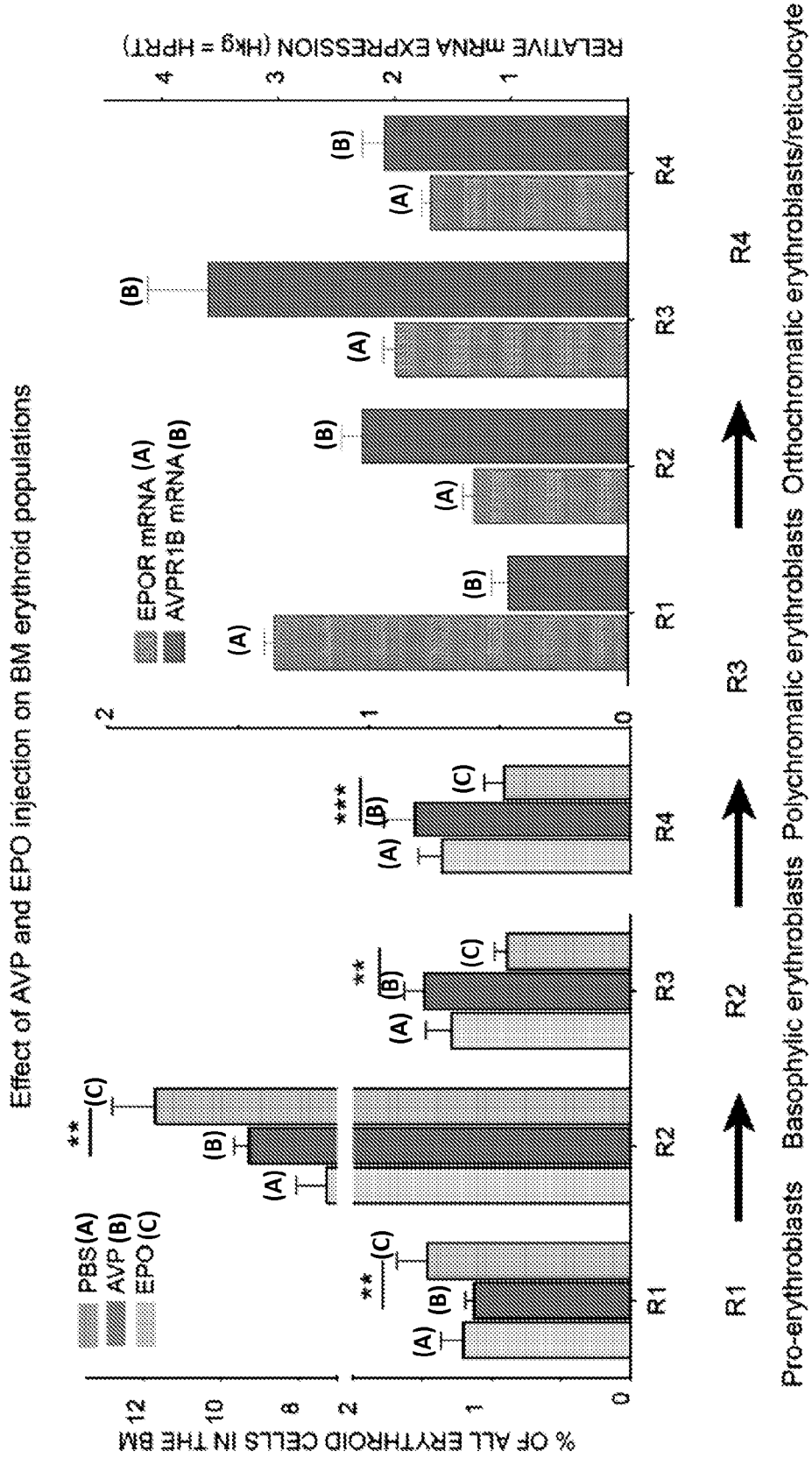
Figure 16:
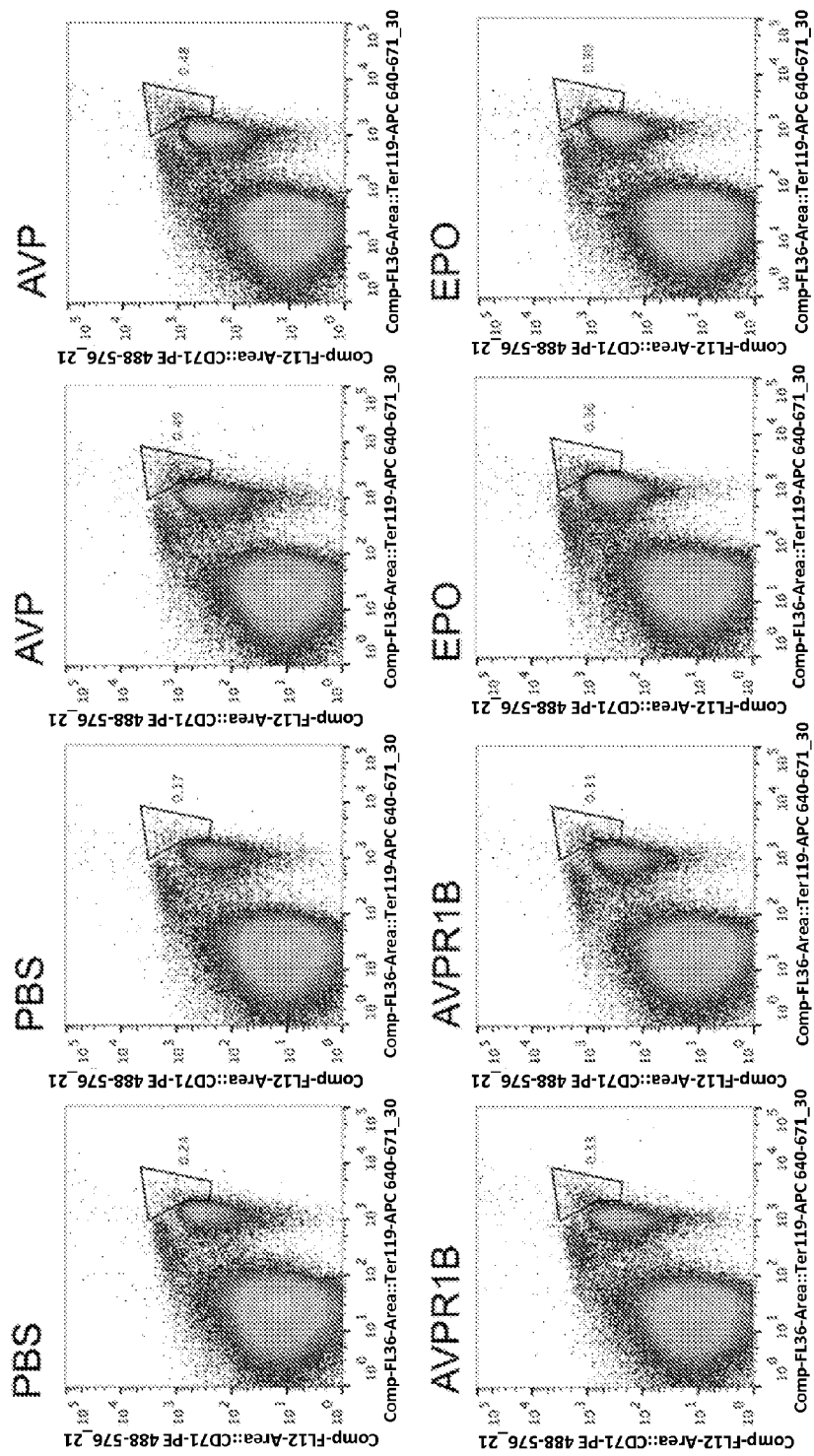
FIG. 16 illustrates the effect of AVP, AVPR1B agonist and EPO on BM erythroid cells. Mice were injected with AVP, AVPR1B and EPO and 16 hours later the BM was analyzed by flow cytometry. The plots demonstrate the different erythroid populations using Ter-119 and CD 71 as markers. There is a clear increase in progenitors following both AVP and AVPR1B injections (gated area).

The inventors determined that AVP induced a fast hematocrit response in severe anemia that is independent of EPO. AVP receptors in the HSPCs was confirmed and they next decided to examine how AVP affects the erythroid lineage cells (developmental stages) in the BM. As in one of the first studies looking at BM 16 hours after AVP injection (FIG. 9B), AVP, AVPR1B agonist, EPO and PBS were injected into mice and looked at the changes in the developing erythroid BM populations including cell cycle data using flow cytometry (FIG. 10C, FIG. 16). In cell populations sorted as above, the presence of AVPR1B and EPO receptor (EPOR) mRNA using QPCR was also determined. AVP significantly increased the numbers of more mature erythroid cells (polychromatic and orthochromatic erythroblasts/reticulocytes) while EPO increased the numbers less mature (proerythroblast/basophilic erythroblast) ones (FIG. 10C and FIG. 16). Cell cycle studies using EdU and Annexin V and DAPI, both showed a significant decrease in apoptosis by AVP in the late progenitor populations. Furthermore there was significantly more EPOR than AVPR1B mRNA in the proerythroblast population, while AVPR1B exceeds EPOR levels starting at the basophilic erythroblast population (FIG. 10C). AVPR2 mRNA was detected in all populations, whereas AVPR1A mRNA was barely detectable.

Discussion

Following severe hemorrhage the body can quickly deteriorate due to a drop in blood pressure and a loss of oxygen-carrying erythrocytes. Due to the volume loss, large amounts of arginine vasopressin (AVP) are released into the circulation by cells of the hypothalamo-hypophyseal system. This hormone is also called the anti-diuretic hormone (ADH) because it inhibits water loss by the kidney. This helps to prevent further volume loss, but has not been shown to promote erythrocyte recovery in the blood. Hypoxia, on the other hand, stimulates erythropoietin (EPO) release by specialized interstitial fibroblasts in the kidney, and this hormone drives the proliferation of erythroid progenitors in the bone marrow. Since this involves the division and differentiation of several consecutive cell populations in the BM, it takes 3-5 days for EPO to increase the number of reticulocytes and mature red blood cells in the periphery. The body could benefit from a much faster increase in blood cells, and hypothesized that since the HSPCs express receptors for AVP the hormone might play an acute role in inducing red blood cell production.

The inventors first detected the presence of all three AVP receptors in mouse LSK (lineage$^-$, Sca-1$^+$, c-kit$^+$) cells (14) as well as human HSPCs (CD34$^+$ cells), and showed that AVP stimulates proliferation of these cells in vitro. This effect was dose-dependent, exhibiting a bell-shaped curve. The proliferation rate was the highest at $10^{-10}$ M. The decrease of the cell proliferation at higher concentrations ($10^{-8}$ M) might reflect receptor desensitization at high peptide levels. The concentration of AVP in the human serum is normally $0.3$-$2\times10^{-12}$M. After blood is lost during surgery, the serum concentration of AVP increases to $0.5$-$1.0\times10^{-10}$ M, concentrations that should be optimal for the proliferative effect observed in vitro.

Stimulating human CD34$^+$ progenitors in vitro resulted in increased intra-cellular Ca$^{2+}$ concentrations when we applied AVP or AVP dCha$^4$AVP, a selective AVPR1B receptor agonist, but not when an AVPR1A agonist was applied suggesting a role for the AVPR1B in the proliferative effect.

The inventors observed the nuclear translocation of β-catenin in response to AVP stimulation. β-catenin mediates the effect of the canonical Wnt signaling pathway leading to HSPC proliferation. The effect of AVP on human HSPCs might be attributed to AVPR1B or AVPR2. The inventors observed the effect of specific AVPR1B agonists on cell proliferation, and an increased cAMP due to AVP stimulation of HSPCs. The disclosed in vitro and in vivo studies both indicated that—although a specific AVPR1B agonist has a significant effect—another receptor might also be involved, since AVP itself was always more effective than the AVPR1B agonist alone. It is possible that in the hematopoietic progenitors these two receptors work in concert to mediate the effect of AVP. One can infer that the differential expression of these two receptor mRNAs in different precursor cells might allow for more fine-tuning of the effect.

The disclosed in vivo results demonstrate that acute injection of AVP increases the percentage of progenitor populations in the BM. The slow recovery of Brattleboro rats after irradiation damage of the BM also confirms the physiological role of AVP in hematopoiesis. The involvement of the AVP1RB in the process is supported by the analysis of the AVPR1B KO mice, where decreased numbers of progenitors are observed. Transplanted bone marrow cells lacking AVPR1B receptors did not promote recovery of red blood cells as effectively as BM derived from WT cells following lethal irradiation of the host mice. Similar to the BM results, in all three anemia models tested, AVP induced a very quick increase in hematocrit as well as an increase in the number of reticulocytes, especially high intensity staining, young reticulocytes.

The effect of EPO versus AVP following hemorrhage was evaluated and AVP started to act very quickly; there was already a significant increase in hematocrit 12 hours following the insult. EPO, on the other hand, needed 3-5 days to improve peripheral blood counts, and in vivo neutralization of EPO did not eliminate the fast action of AVP. These results indicate that AVP has a fast effect that is independent of EPO.

Figure 11:
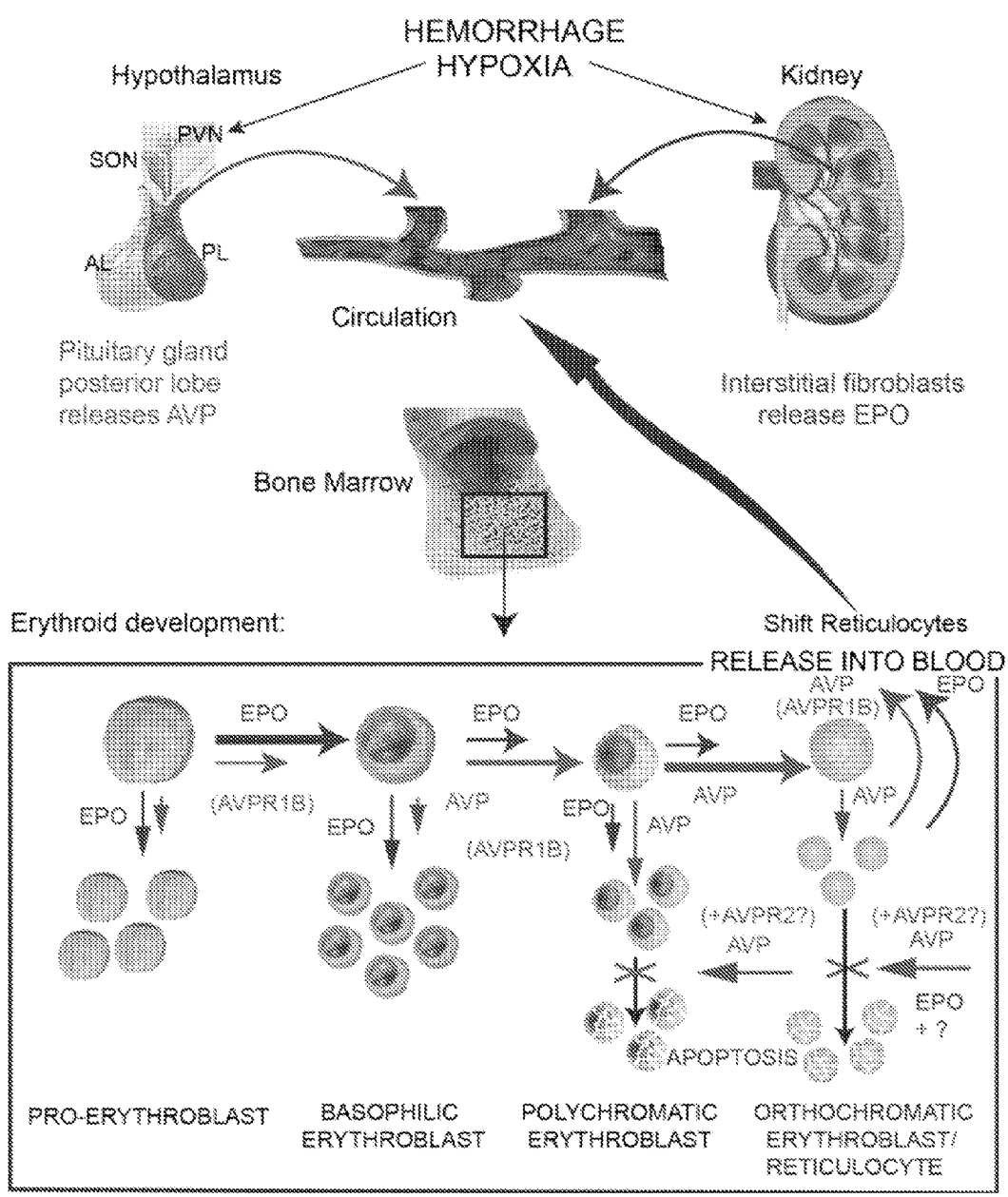
FIG. 11 provides a schematic figure showing the coordinated response to hemorrhage or hypoxia by AVP and EPO. In response to blood loss or hypoxia, AVP is released into the blood from the hypothalamo-hypophyseal system, and EPO is released from the specialized interstitial fibroblasts of the kidney. EPO induces proliferation of proerythroblasts and basophilic erythroblasts, as well as their differentiation down the lineage. AVP induces proliferation of polychromatic and orthochromatic erythroblasts, and might speed up the differentiation/maturation process of young reticulocytes into mature reticulocytes. It is contemplated that AVPR1B could be responsible for the effects on proliferation and differentiation. AVP seems to decrease apoptosis in the most mature population—this effect might be affiliated with the AVPR2. Both EPO and AVP participate in the release of cells into the circulation—AVP might be responsible for the quick release of immature red cells into the circulation (shift-reticulocytes) and speeding up their maturation—thus resulting in a rapid increase in hematocrit values.

Based on these results, elevated levels of AVP were predicted to have multiple roles in animals that have lost blood, and that it acts together with EPO (FIG. 11). It activates AVPR2 receptors in the kidney to stimulate water resorption and compensate for the volume loss. It helps to stop the bleeding by releasing von Willebrand factor from endothelial cells. Simultaneously, AVP stimulates hematopoiesis driving the replacement of lost erythrocytes. Thus, AVP jumpstarts the proliferation of HSPCs. In addition to inducing proliferation and likely speeding up differentiation, AVP also seems to be able to mobilize a large number of immature reticulocytes from the BM into the circulation, where they appear larger and contain more reticulum (cytoplasmic reticular network of ribosomal RNA) than normal reticulocytes. Cell cycle studies using EdU in hemorrhage followed by AVP treatment also indicate that AVP reduces apoptosis of immature blood cells, which would help to fill the acute need. In fact, AVP has been shown to have anti-apoptotic effect in a variety of mammalian cells, including renal tubular and endothelial cells.

Currently, EPO is the only agent that is used clinically to stimulate hematopoiesis, but there are patients who do not respond to EPO or who cannot take the drug. Based upon the discoveries disclosed herein, a peripherally active AVPR1B agonist could be used to treat patients with anemia due to chemotherapy. Alternatively, nicotine patches could also be used for this purpose, since nicotine is a potent stimulant of AVP release from the posterior pituitary. In fact, cigarette smokers are known to have high hematocrits that tend to normalize when they stop smoking.

Example 4

Method to Treat Anemia

This example describes a particular method that can be used to treat anemia in humans by administration of an AVPR1B receptor agonist, such as d[Leu4, Lys8]-VP.

In the case of an acute hemorrhage (such as a trauma in the battlefield) the AVPR1B agonist should be administered as soon as possible. According to the FDA conversion factor between rodents and human, a dose of 5-20 µg/kg bodyweight iv is to be administered. This dose may be repeated twice a day for the first 4 days (or until the patient is stabilized). By day 5, the effect of the EPO released by the bleeding will take effect and will efficiently increase the red cell production. If there is significant blood loss and the patient is unconscious both oral and iv application maybe difficult. For such circumstance a nasal spray of the medicine should work well. In the case of chemotherapy, EPO is usually given to stimulate erythroid production. At the same time, 5-20 µg/kg bodyweight iv AVPR1b treatment should be initiated and the hematocrit and hemoglobin levels should be monitored. The dose and the frequency of the injection should be modified based on the hematocrit/hemoglobin values. In the case of chemotherapy the AVPR1B treatment might be continued parallel with EPO treatment—the two treatment together might work faster than either one alone.

Based upon the teaching disclosed herein, anemia can be treated by administering an effective amount of an AVPR1B receptor agonist, such as d[Leu4, Lys8]-VP, thereby stimulating erythropoiesis and thus treating anemia.

Briefly, the method can include screening subjects to determine if they have anemia or are likely to develop it. Subjects having anemia or at risk of developing anemia, such as a subject undergoing chemotherapy, are selected. Examples of methods that can be used to screen for anemia include monitoring hematocrit and hemoglobin levels. If blood or a fraction thereof (such as serum) is used, 300-1000 µl of blood is collected. Serum can either be used directly or fractionated using filter cut-offs to remove high molecular weight proteins. If desired, the serum can be frozen and thawed before use. If anemia is detected, then the subject is a candidate for receiving the therapies disclosed herein. However, such pre-screening is not required prior to administration of the therapies disclosed herein.

Following subject selection, a therapeutic effective dose of a composition is administered to the subject, wherein the composition includes an AVPR1B receptor agonist, such as d[Leu4, Lys8]-VP. These complexes can then be delivered in vivo by oral, intravenous or nasal application at 50-100 µg/kg (oral) or 1-20 µg/kg (iv). The administration can be repeated every 12 hours for 4 days until initially administered EPO can start to take over.

Assessment

Following the administration of one or more therapies, subjects having anemia can be monitored, such as a hematocrit/hemoglobin elevation indicate the treatment is effective for treating anemia. In particular examples, subjects are analyzed one or more times, starting 12 hours following treatment. Subjects can be monitored using any method known in the art. For example, analysis of biological samples from the subject (for example analysis of blood) can be used to monitor a subject's condition.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of treating anemia, comprising administering an effective amount of an arginine vasopressin receptor 1B (AVPR1B) agonist to a subject having anemia, wherein the AVPR1B agonist is [Arg$^8$]-Vasopressin (AVP), d[Leu$^4$, Lys$^8$]-vasopressin, or dCha$^4$AVP, thereby treating the anemia.

2. The method of claim 1, wherein administering the effective amount of the AVRP1B agonist stimulates hematopoietic stem cell (HSC) proliferation.

3. The method of claim 1, wherein the subject is receiving or has received chemotherapy.

4. The method of claim 1, wherein the anemia is due to a hemorrhage.

5. The method of claim 4, wherein the hemorrhage is due to traumatic injury.

6. The method of claim 1, wherein the AVPR1B agonist is administered with one or more additional erythropoiesis stimulatory molecules.

7. The method of claim 6, wherein the one or more additional erythropoiesis stimulatory molecules is erythropoietin or nicotine.

8. The method of claim 6, wherein the one or more additional erythropoiesis stimulatory molecules is erythropoietin.

9. The method of claim 1, wherein the method comprises administering the effective amount of the AVPR1B agonist followed by administering one or more additional erythropoiesis stimulatory molecules.

10. The method of claim 9, wherein the one or more additional erythropoiesis stimulatory molecules is erythropoietin.

11. The method of claim 10, wherein the method comprises administering the effective amount of the AVPR1B agonist by acute injection or for 12 to 72 hours followed by administering the erythropoietin.

12. The method of claim 1, wherein administering the effective amount of the AVPR1B agonist stimulates erythropoiesis in the subject.

13. The method of claim 1, wherein the subject is receiving or has received radiation.

14. The method of claim 1, wherein the subject was non-responsive or had or at risk of having an adverse reaction to erythropoietin (EPO).

15. The method of claim 1, wherein the anemia results from chronic kidney disease or inflammatory bowel disease.

16. The method of claim 15, wherein the inflammatory bowel disease is Crohn's disease or ulcerative colitis.

17. The method of claim 1, wherein the anemia is due to excessive blood cell destruction.

18. The method of claim 1, wherein the anemia is due to deficient red blood cell production.

19. A method of treating anemia caused by radiation treatment of a cancer in a subject, comprising administering an effective amount of an arginine vasopressin receptor 1B (AVPR1B) agonist to the subject, wherein the AVPR1B agonist is [Arg$^8$]-Vasopressin (AVP), d[Leu$^4$, Lys$^8$]-vasopressin or dCha$^4$AV, thereby treating anemia.

20. The method of claim 19, wherein the method comprises administering the effective amount of the AVPR1B agonist by acute injection or for 12 to 72 hours.

21. The method of claim 20, further comprising administering erythropoietin or nicotine after administering the AVPR1B agonist.

22. The method of claim 19, further comprising administering radiation treatment to the subject prior to administering the AVPR1B agonist.

* * * * *

SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 1
ccgcctgggt gctgagcttc                                                 20

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide primer

```
<400> SEQUENCE: 2
tcttcccgcg gacgttgcac                                               20

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 3
ggctgccatc tcgggtcagc                                               20

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 4
caggcaaggt gacgcagggg                                               20

<210> SEQ ID NO 5
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 5
attcatgcca gtctggtgc                                                19

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 6
tcacgatgaa gtgtccttgg                                               20

<210> SEQ ID NO 7
<211> LENGTH: 24
<212> TYPE: DNA
<213> ORGANISM: Artificial Sequence
<220> FEATURE:
<223> OTHER INFORMATION: synthetic oligonucleotide primer

<400> SEQUENCE: 7
atcatcgtgc tggccttcat cgtg                                          24

<210> SEQ ID NO 8
<211> LENGTH: 24
<212> TYPE: DNA
<213> ORGANISM: Artificial Sequence
<220> FEATURE:
<223> OTHER INFORMATION: synthetic oligonucleotide primer

<400> SEQUENCE: 8
ccttatacac aaacatacgc catc                                          24

<210> SEQ ID NO 9
```

```
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 9
cgacctggag ctgagacag                                              19

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 10
cggcaggtag ttctcctcct                                             20

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 11
ggaggagaac tacctgccgt                                             20

<210> SEQ ID NO 12
<211> LENGTH: 18
<212> TYPE: DNA
<213> ORGANISM: Artificial Sequence
<220> FEATURE:
<223> OTHER INFORMATION: synthetic oligonucleotide primer

<400> SEQUENCE: 12
gctgggagaa ggtggctt                                               18

<210> SEQ ID NO 13
<211> LENGTH: 22
<212> TYPE: DNA
<213> ORGANISM: Artificial Sequence
<220> FEATURE:
<223> OTHER INFORMATION: synthetic oligonucleotide primer

<400> SEQUENCE: 13
cagatgtggt cagtctggga ta                                          22

<210> SEQ ID NO 14
<211> LENGTH: 22
<212> TYPE: DNA
<213> ORGANISM: Artificial Sequence
<220> FEATURE:
<223> OTHER INFORMATION: synthetic oligonucleotide primer

<400> SEQUENCE: 14
ctcatgctat ccgagtcatc ct                                          22

<210> SEQ ID NO 15
<211> LENGTH: 24
<212> TYPE: DNA
<213> ORGANISM: Artificial Sequence
<220> FEATURE:
<223> OTHER INFORMATION: synthetic oligonucleotide primer

<400> SEQUENCE: 15
```

```
gctggcccaa gtcctcatct tctg                                          24

<210> SEQ ID NO 16
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 16
gcggtgactc agggaacgt                                                19

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 17
cacgtctgca gtgcctgggg                                               20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 18
catggaagcg gtcggtggca                                               20

<210> SEQ ID NO 19
<211> LENGTH: 22
<212> TYPE: DNA
<213> ORGANISM: Artificial Sequence
<220> FEATURE:
<223> OTHER INFORMATION: synthetic oligonucleotide primer

<400> SEQUENCE: 19
cctttcttct tcgtgcagat gt                                            22

<210> SEQ ID NO 20
<211> LENGTH: 22
<212> TYPE: DNA
<213> ORGANISM: Artificial Sequence
<220> FEATURE:
<223> OTHER INFORMATION: synthetic oligonucleotide primer

<400> SEQUENCE: 20
ggaggagttg cttttcttgc ta                                            22

<210> SEQ ID NO 21
<211> LENGTH: 22
<212> TYPE: DNA
<213> ORGANISM: Artificial Sequence
<220> FEATURE:
<223> OTHER INFORMATION: synthetic oligonucleotide primer

<400> SEQUENCE: 21
ggcatctgct gcagcgacga ga                                            22

<210> SEQ ID NO 22
<211> LENGTH: 21
<212> TYPE: DNA
```

```
<213> ORGANISM: Artificial Sequence
<220> FEATURE:
<223> OTHER INFORMATION: synthetic oligonucleotide primer

<400> SEQUENCE: 22
tagacccggg gcttggcaga a                                              21

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 23
caagggacac cctggttcta                                                20

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 24
ctacgcaact ccgaggagac                                                20

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 25
taggcctggt tcgtaagcat                                                20

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 26
ttcaatcacg gaccagttca                                                20

<210> SEQ ID NO 27
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 27
gtctgacttg gcctcaaagc                                                20

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 28
gtgaggtgga gtgggaggta                                                20
```

```
<210> SEQ ID NO 29
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 29
atccgaaccg tgaagatgac                                                   20

<210> SEQ ID NO 30
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 30
tcattagggg cattctcgtc                                                   20
```